(12) United States Patent
Phadke et al.

(10) Patent No.: US 9,133,115 B2
(45) Date of Patent: Sep. 15, 2015

(54) 4-AMINO-4-OXOBUTANOYL PEPTIDES AS INHIBITORS OF VIRAL REPLICATION

(71) Applicants: Avinash Phadke, Branford, CT (US); Cuixian Liu, Madison, CT (US)

(72) Inventors: Avinash Phadke, Branford, CT (US); Cuixian Liu, Madison, CT (US)

(73) Assignee: ACHILLION PHARMACEUTICALS, INC., New Haven, CT (US)

( * ) Notice: Subject to any disclaimer, the term of this patent is extended or adjusted under 35 U.S.C. 154(b) by 0 days.

(21) Appl. No.: 14/139,196

(22) Filed: Dec. 23, 2013

(65) Prior Publication Data

US 2014/0113890 A1    Apr. 24, 2014

Related U.S. Application Data

(63) Continuation of application No. 12/635,270, filed on Dec. 10, 2009, now Pat. No. 8,614,180.

(60) Provisional application No. 61/226,317, filed on Jul. 17, 2009, provisional application No. 61/121,378, filed on Dec. 10, 2008.

(51) Int. Cl.
| | |
|---|---|
| C07D 207/16 | (2006.01) |
| C07D 401/12 | (2006.01) |
| C07D 401/14 | (2006.01) |
| C07D 403/12 | (2006.01) |
| C07D 403/14 | (2006.01) |
| C07D 409/14 | (2006.01) |
| C07D 413/14 | (2006.01) |
| C07D 417/14 | (2006.01) |
| C07D 471/08 | (2006.01) |
| C07D 487/08 | (2006.01) |
| C07D 491/113 | (2006.01) |
| C07D 417/12 | (2006.01) |
| C07D 487/18 | (2006.01) |

(52) U.S. Cl.
CPC ............ *C07D 207/16* (2013.01); *C07D 401/12* (2013.01); *C07D 401/14* (2013.01); *C07D 403/12* (2013.01); *C07D 403/14* (2013.01); *C07D 409/14* (2013.01); *C07D 413/14* (2013.01); *C07D 417/12* (2013.01); *C07D 417/14* (2013.01); *C07D 471/08* (2013.01); *C07D 487/08* (2013.01); *C07D 487/18* (2013.01); *C07D 491/113* (2013.01)

(58) Field of Classification Search
CPC ......... A61K 38/05; A61K 38/12; C07K 5/02; C07K 5/06078; C07K 5/06191; C07K 5/0808
See application file for complete search history.

(56) References Cited

U.S. PATENT DOCUMENTS

| | | | |
|---|---|---|---|
| 6,867,185 B2 | 3/2005 | Campbell et al. | |
| 6,872,805 B2 | 3/2005 | Campbell et al. | |
| 6,908,901 B2 | 6/2005 | Bailey et al. | |
| 6,995,174 B2 | 2/2006 | Wang et al. | |
| 7,041,698 B2 | 5/2006 | Ripka et al. | |

(Continued)

FOREIGN PATENT DOCUMENTS

| | | |
|---|---|---|
| EP | 1881002 A1 | 1/2008 |
| WO | 9101327 A1 | 2/1991 |

(Continued)

OTHER PUBLICATIONS

Supplemental Search Report for European Patent Application No. 08834325.6; European Filing Date: Sep. 24, 2008; Date of Mailing: Jan. 16, 2013. 6 Pages.

(Continued)

*Primary Examiner* — Christina Bradley
*Assistant Examiner* — Randall L Beane
(74) *Attorney, Agent, or Firm* — Cantor Colburn LLP

(57) ABSTRACT

The invention provides 4-amino-4-oxobutanoyl peptides of Formula I (Formula I)

and the pharmaceutically salts and hydrates thereof. The variables R, $R_1$, $R_6$-$R_8$, $R_{16}$, $R_{18}$, $R_{19}$, M, n, T, Y, and Z are defined herein. Certain compounds of Formula I are useful as antiviral agents. The 4-amino-4-oxobutanoyl peptides disclosed herein are potent and/or selective inhibitors of viral replication, particularly Hepatitis C virus replication. The invention also provides pharmaceutical compositions containing one or more 4-amino-4-oxobutanoyl peptides and one or more pharmaceutically acceptable carriers. Such pharmaceutical compositions may contain a 4-amino-4-oxobutanoyl peptides as the only active agent or may contain a combination of a 4-amino-4-oxobutanoyl peptides and one or more other pharmaceutically active agents. The invention also provides methods for treating viral infections, including Hepatitis C infections.

4 Claims, No Drawings

(56) References Cited

U.S. PATENT DOCUMENTS

| | | | |
|---|---|---|---|
| 7,176,208 B2 | 2/2007 | Nakajima et al. | |
| 7,659,263 B2 | 2/2010 | Mizojiri et al. | |
| 7,906,619 B2 | 3/2011 | Phadke et al. | |
| 8,614,180 B2 * | 12/2013 | Phadke et al. | ............... 514/4.3 |
| 2003/0224977 A1 | 12/2003 | Llinas-Brunet et al. | |
| 2004/0002448 A1 | 1/2004 | Tsantrizos et al. | |
| 2004/0048802 A1 | 3/2004 | Ripka et al. | |
| 2004/0077551 A1 | 4/2004 | Campbell et al. | |
| 2004/0106559 A1 | 6/2004 | Wang et al. | |
| 2004/0224900 A1 | 11/2004 | Bailey et al. | |
| 2005/0020503 A1 | 1/2005 | Llinas-Brunet et al. | |
| 2005/0153877 A1 | 7/2005 | Miao et al. | |
| 2005/0267040 A1 | 12/2005 | Scola et al. | |
| 2006/0019905 A1 | 1/2006 | Bailey et al. | |
| 2006/0046965 A1 | 3/2006 | Bailey et al. | |
| 2006/0046983 A1 | 3/2006 | Hudyma et al. | |
| 2006/0142204 A1 | 6/2006 | Halfon et al. | |
| 2006/0199773 A1 | 9/2006 | Sausker et al. | |
| 2006/0281688 A1 | 12/2006 | Zhang et al. | |
| 2007/0010455 A1 | 1/2007 | Hewawasam et al. | |
| 2007/0093414 A1 | 4/2007 | Carini et al. | |
| 2007/0099825 A1 | 5/2007 | D'Andrea et al. | |
| 2009/0048297 A1 | 2/2009 | Phadke et al. | |
| 2010/0216725 A1 | 8/2010 | Phadke et al. | |

FOREIGN PATENT DOCUMENTS

| | | |
|---|---|---|
| WO | 9325574 A1 | 12/1993 |
| WO | 0059929 A1 | 10/2000 |
| WO | 02060926 A2 | 8/2002 |
| WO | 03099274 A1 | 12/2003 |
| WO | 03099316 A1 | 12/2003 |
| WO | 2004043339 A2 | 5/2004 |
| WO | 2004072243 A2 | 8/2004 |
| WO | 2004094452 A2 | 11/2004 |
| WO | 2004103996 A1 | 12/2004 |
| WO | 2004113365 A2 | 12/2004 |
| WO | 2005028501 A1 | 3/2005 |
| WO | 2005037214 A2 | 4/2005 |
| WO | 2005046712 A1 | 5/2005 |
| WO | 2005051410 A1 | 6/2005 |
| WO | 2005054430 A2 | 6/2005 |
| WO | 2005070955 A1 | 8/2005 |
| WO | 2005073216 A2 | 8/2005 |
| WO | 2005090383 A2 | 9/2005 |
| WO | 2005095403 A2 | 10/2005 |
| WO | 2006007700 A1 | 1/2006 |
| WO | 2006007708 A1 | 1/2006 |
| WO | 2006002076 A2 | 2/2006 |
| WO | 2006020276 A2 | 2/2006 |
| WO | 2006033878 A1 | 3/2006 |
| WO | 2006086381 A2 | 8/2006 |
| WO | 2006096652 A2 | 9/2006 |
| WO | 2006122188 A2 | 11/2006 |
| WO | 2005007681 A2 | 1/2007 |
| WO | 2007005838 A2 | 1/2007 |
| WO | 2007009109 A2 | 1/2007 |
| WO | 2007009227 A1 | 1/2007 |
| WO | 2007014919 A1 | 2/2007 |
| WO | 2007014927 A3 | 2/2007 |
| WO | 2007015824 A2 | 2/2007 |
| WO | 2007030656 A1 | 3/2007 |
| WO | 2007044893 A2 | 4/2007 |
| WO | 2008008502 A1 | 1/2008 |
| WO | 2008086161 A1 | 7/2008 |
| WO | 2008095058 A1 | 8/2008 |

OTHER PUBLICATIONS

Supplemental Search Report for European Application No. 08834325.6; European Filing Date: Sep. 24, 2008; Date of Mailing: Jan. 16, 2013; 6 Pages.

U.S. Appl. No. 61/116,526, filed Nov. 20, 2008.

Andrews, et al., "Pyrrolidine-5,5-trans-lactams. 2. The Use of X-ray Crystal Structure Data in the Optimization of P3 and P4 Substituents," Organic Letters, 4(25): 4479-4482 (2002).

Arasappan, et al., "Hepatitis C virus NS3-4A serine protease inhibitors: SAR of P2 moiety with improved potency," Bioorganic & Medicinal Chemistry Letters, 15: 4180-4184 (2005).

Barbato, et al., "Inhibitor binding induces active site stabilization of the HCV NS3 protein serine protease domain," The EMBO Journal, 19(6): 1195-1206 (2000).

Di Marco, et al., "Inhibition of the Hepatitis C Virus NS3/4A Protease," The Journal of Biological Chemistry, 275(10): 7152-7157 (2000).

International Search Report for Application No. PCT/US2007/016018 dated Dec. 12, 2007.

International Search Report for Application No. PCT/US2008/002524 mailed Aug. 26, 2008.

International Search Report for Application No. PCT/US2009/067506 dated Aug. 20, 2010.

Liu, et al., "Hepatitis C NS3 protease inhibition by peptidyl-alpha-ketoamide inhibitors: kinetic mechanism and structure," Archives of Biochemistry and Biophysics, 421: 207-216 (2004).

Llinas-Brunet, et al., "A Systematic Approach to the Optimization of Substrate-Based Inhibitors of the Hepatitis C Virus NS3 Protease: Discovery of Potent and Specific Tripeptide Inhibitors," J. Med. Chem., 47: 6584-6594 (2004).

Ontoria, et al., "The Design and Enzyme-Bound Crystal Structure of Indoline Based Peptidomimetic Inhibitors of Hepatitis C Virus NS3 Protease," J. Med. Chem., 47: 6443-6446 (2004).

Rakic, et al., "A Small-Molecule Probe for Hepatitis C Virus Replication that Blocks Protein Folding," Chemistry & Biology, 13: 1051-1060 (2006).

Slater, et al., "Pyrrolidine-5,5-trans-lactams. 4. Incorporation of a P3/P4 Urea Leads to Potent Intracellular Inhibitors of Hepatitis C Virus NS3/4A Protease," Organic Letters, 5(24): 4627-4630 (2003).

Venkatraman, et al., "Discovery of (1R,5S)-N-[3-Amino-1-(cyclobutylmethyl)-2,3-dioxopropyl]-3-[2(S)-[[[(1,1-dimethylethyl)amino}amino]-3,3-dimethyl-1-oxobutyl]-6,6-dimethyl-3-azabicyclo[3.1.0]hexan-2(S)-carboxamide (SCH 503034), a Selective, Potent, Orally Bioavailable Hepatitis C Virus NS3 Protease Inhibitor: A Potential Therapeutic Agent for the Treatment of Hepatitis C Infection," J. Med. Chem., 49: 6074-6086 (2006).

Written Opinion for International Application No. PCT/US2009/067506 dated Aug. 20, 2010.

Cregge et al., "Inhibition of Human Neutrophil Elastase. 4. Design, Synthesis, X-ray Crystallographic Analysis, and Structure- Activity Relationships for a Series of P2-Modified, Orally Active Peptidyl Pentafluoroethyl Ketones" Journal of Med. Chem.; 41, (1998), pp. 2461-2480.

European Search Report for EU Application No. 09832542.6, International Filing Date Dec. 10, 2009, Date of Mailing Apr. 16, 2012, 5 pages.

European Search Report for European Application No. 11169378, European Filing Date: Jul. 13, 2007; Date of Mailing: Apr. 2, 2012, 6 Pages.

Goudreau, Nathalie et al. "Potent Inhibitors of the Hepatitis C Virus NS3 Protease: Design and Synthesis of Macrocyclic Substrate-Based B-Strand Mimics", Journal Organic Chemistry, 2004, 69, pp. 6185-6201.

Lin, et al., "In Vitro Resistance Studies of Hepatitis C Virus Serine Protease Inhibitors, VX-950 and BILN 2061," The Journal of Biological Chemistry 279(17): 17508-17514 (2004).

Prongay, et al., "Discovery of the HCV NS3/4A Protease Inhibitor (1R,5S)-N-[43-Amino-1-(cyclobutylmethyl)-2,3-ioxopropyl]-3-[2(S)-[[[(1,1-dimethylethyl)amino]carbonyl]amino]-3,3-dimethyl-1-oxobutyl]- 6,6-dimethyl-3-azabicyclo [3.1.0]hexan-2(S)-carboxamide (Sch 503034) II. Key Steps in Structure-Based Optimization" J. Med. Chem., 50, (2007), pp. 2310-2318.

Search Report of the International Searching Authority for International Patent Application No. PCT/US2007/016018; International Filing Date: Jul. 13, 2007; Date of mailing: Dec. 12, 2007; 3 Pages.

Supplemental European Search Report for EU Application No. 09832541.8, International Filing Date: Jun. 17, 2010, Date of Mailing: Jul. 27, 2012; 6 Pages.

(56) References Cited

OTHER PUBLICATIONS

Tsantrizos, et al., "Macrocyclic Inhibitors of the NS3 Protease as Potential Therapeutic Agents of Hepatitis C Virus Infection," Agnew. Chem. Int. Ed., 42(12): 1355-1360 (2003).

Written Opinion of the International Searching Authority for International Patent Application No. PCT/US2009/067507; International Filing Date: Dec. 10, 2009; Date of Mailing: Aug. 24, 2010; 5 Pages.

* cited by examiner

4-AMINO-4-OXOBUTANOYL PEPTIDES AS INHIBITORS OF VIRAL REPLICATION

CROSS REFERENCE TO RELATED APPLICATIONS

This application is a continuation of U.S. application Ser. No. 12/635,270, filed Dec. 10, 2009, which claims priority to US Provisional Patent Application Nos. 61/121,378 filed Dec. 10, 2008 and 61/226,317 filed Jul. 17, 2009, all of which are hereby incorporated by reference in their entirety.

FIELD OF THE INVENTION

The present invention provides 4-amino-4-oxobutanoyl peptides, useful as antiviral agents. Certain 4-amino-4-oxobutanoyl peptides disclosed herein are potent and/or selective inhibitors of viral replication, particularly Hepatitis C virus replication. The invention also provides pharmaceutical compositions containing one or more provides 4-amino-4-oxobutanoyl peptides and one or more pharmaceutically acceptable carriers. Such pharmaceutical compositions may contain a 4-amino-4-oxobutanoyl peptide as the only active agent or may contain a combination of a 4-amino-4-oxobutanoyl peptide and one or more other pharmaceutically active agents. The invention also provides methods for treating viral infections, including Hepatitis C infections.

BACKGROUND

An estimated 3% of the world's population is infected with the hepatitis C virus. Of those exposed to HCV, 80% to 85% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained viro logic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-806, VX-950 and NM 283 (prodrug of NM 107) are in clinical development for treatment of chronic HCV. Due to lack of effective therapies for treatment for certain HCV strains and the high mutation rate of HCV, new therapies are needed.

The present invention fulfills this need and provides additional advantages, which are described herein.

SUMMARY OF THE INVENTION

The invention provides compounds of Formula I (shown below) and includes 4-amino-4-oxobutanoyl peptides. The 4-amino-4-oxobutanoyl peptides of Formula I disclosed herein possess antiviral activity. The invention provides compounds of Formula I that are potent and/or selective inhibitors of Hepatitis C virus replication. The invention also provides pharmaceutical compositions containing one or more compound of Formula I, or a salt, solvate, or acylated prodrug of such compounds, and one or more pharmaceutically acceptable carriers.

The invention further comprises methods of treating patients suffering from certain infectious diseases by providing to such patients an amount of a compound of Formula I effective to reduce signs or symptoms of the disease or disorder. These infectious diseases include viral infections, particularly HCV infections. The invention particularly includes methods of treating human patients suffering from an infectious disease, but also encompasses methods of treating other animals, including livestock and domesticated companion animals, suffering from an infectious disease.

Methods of treatment include providing a compound of Formula I as a single active agent or providing a compound of Formula I in combination with one or more other therapeutic agents.

Thus in a first aspect the invention includes compounds of Formula I pharmaceutically acceptable salts thereof:

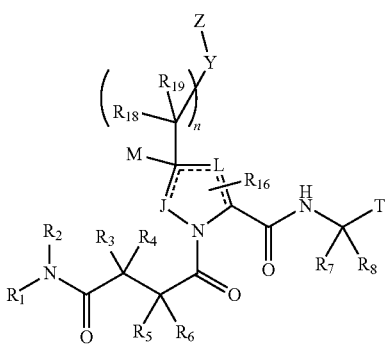

(Formula I)

Within Formula I
===== represents a double or single covalent bond, and the group

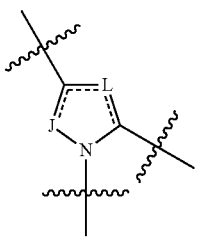

contains 0 or 1 double bonds.

$R_1$ and $R_2$ meet one of the following conditions:

(i) $R_1$ is —$NR_{10}R_{11}$, —(C=O)$NR_{10}R_{11}$, —(C=S)$NR_{10}R_{11}$, —(C=O)$R_{12}$, —$SO_2R_{12}$, —(C=O)$OR_{12}$, —O(C=O)$R_{12}$, —$OR_{12}$, or —N(C=O)$R_{12}$, and $R_2$ is hydrogen, $C_1$-$C_6$alkyl, $C_3$-$C_7$cycloalkyl, heterocycloalkyl, (aryl)$C_0$-$C_4$alkyl, or (ii) $R_1$ and $R_2$ are joined to form a 4- to 7-membered heterocyloalkyl ring containing 0 to 2 additional heteroatoms independently chosen from N, O, and S which ring is optionally fused to a 5- or 6-membered heterocyclic ring, containing 1 or 2 heteroatoms independently chosen from N, O, and S, or 5- or 6-membered carbocyclic ring to form a bicyclic ring system, each of which 5- to 7-membered heterocycloalkyl ring or bicyclic ring system is optionally substituted;

(iii) $R_1$ and $R_2$ are taken together to form a 5- to 6-membered partially unsaturated or aromatic group that is optionally fused to a phenyl or pyridyl group, which is optionally substituted; or (iv) $R_1$ and $R_2$ are taken together to form an optionally substituted 5- to 9-membered bridged heterocyclic ring containing 0, 1, or 2 additional N, S, or O atoms, or an optionally substituted 5- to 7-membered heterocyclic ring containing 0 or 1 additional N, S, or O atoms fused to an optionally substituted 5- to 7-membered carbocyclic or heterocyclic ring to form a bicyclic ring system which is bridged; or (v) $R_1$ and $R_2$ are taken together to form an optionally substituted 4- to 7-membered heterocyclic ring containing 0 or 1 additional N, S, or O atoms fused to an optionally substituted 5- to 9-membered bridged carbocyclic or heterocyclic ring; or (vi) $R_1$ and $R_2$ are taken together to form an optionally substituted bicyclic system with rings in spiro orientation having a total of 6 to 12 ring atoms with 0, 1 or 2 additional heteroatoms independently chosen from N, O, and S with remaining ring atoms being carbon.

$R_3$, $R_4$, $R_5$, $R_6$, $R_7$, and $R_8$ are independently
(a) hydrogen, halogen, or amino, or
(b) $C_1$-$C_6$alkyl, $C_2$-$C_6$alkenyl, ($C_3$-$C_7$cycloalkyl)$C_0$-$C_4$alkyl, (aryl)$C_0$-$C_4$alkyl, (heteroaryl)$C_0$-$C_4$alkyl, ($C_3$-$C_7$cycloalkenyl)$C_0$-$C_4$alkyl, (heterocycloalkyl)$C_0$-$C_4$alkyl, $C_2$-$C_6$alkanoyl, or mono- or di-$C_1$-$C_6$alkylamino, each of which is optionally substituted.

Or, $R_3$ and $R_4$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

$R_5$ and $R_6$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

$R_7$ and $R_8$ may be joined to form an optionally substituted 3- to 7-membered cycloalkyl ring or an optionally substituted 3- to 7-membered heterocycloalkyl ring containing 1 or 2 heteroatoms independently chosen from N, S, and O.

Or, $R_5$ is a $C_7$-$C_{11}$ saturated or unsaturated hydrocarbon chain that is (i) covalently bound to $R_7$, where $R_7$ is a methylene group or $R_5$ is a $C_7$-$C_{11}$ saturated or unsaturated hydrocarbon chain that is (ii) covalently bound to an optionally substituted cycloalkyl ring formed by $R_7$ and $R_8$ being joined to from a 3- to 7-membered optionally substituted cycloalkyl ring; and $R_6$ is hydrogen, $C_1$-$C_6$alkyl, or ($C_3$-$C_7$cycloalkyl)$C_0$-$C_2$alkyl.

T is a tetrazole group attached via its carbon atom.

Or, T is a group of the formula:

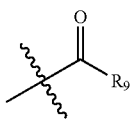

where $R_9$ is one of the following:

$R_9$ is hydroxyl, amino, —COOH, —$NR_{10}R_{11}$, —$OR_{12}$, —$SR_{12}$, —$NR_{10}(S=O)R_{11}$, —$NR_{10}SO_2R_{11}$, —$NR_{10}SONR_{11}R_{12}$, —$NR_{10}SO_2NR_{11}R_{12}$, —(C=O)$OR_{10}$, —$NR_{10}$(C=O)$OR_{11}$, or —CON$R_{10}R_{11}$;

$R_9$ is $C_1$-$C_6$alkyl, $C_2$-$C_6$alkenyl, $C_2$-$C_6$alkanoyl, ($C_3$-$C_7$cycloalkyl)$C_0$-$C_4$alkyl, ($C_3$-$C_7$cycloalkenyl)$C_0$-$C_4$alkyl, ($C_3$-$C_7$cycloalkyl)$CH_2SO_2$—, ($C_3$-$C_7$cycloalkyl)$CH_2SO_2NR_{10}$—, (hetero cycloalkyl)$C_0$-$C_4$alkyl, (aryl)$C_0$-$C_2$alkyl, or (5- to 10-membered heteroaryl)$C_0$-$C_2$alkyl, each of which is optionally substituted;

$R_9$ is a phosphonate of the formula

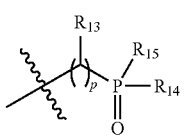

where p is 0, 1, or 2;

$R_9$ is $R_X XC_0$-$C_4$alkyl-, where X is —(C=O)NH—, —NH(C=O)— and $R_X$ is aryl or heteroaryl; or $R_9$ is —CH($R_Y$)($C_3$-$C_7$cycloalkyl), —$SO_2CH(R_Y)$($C_3$-$C_7$cycloalkyl), or —$NR_{10}SO_2CH(R_Y)$($C_3$-$C_7$cycloalkyl), where $R_Y$ is halogen or $R_Y$ is $C_1$-$C_6$alkyl, $C_2$-$C_6$alkanoyl, ($C_3$-$C_7$cycloalkyl)$C_0$-$C_4$alkyl, ($C_4$-$C_7$cycloalkenyl)$C_0$-$C_4$alkyl, (aryl)$C_0$-$C_4$alkyl, (aryl)$C_0$-$C_4$alkoxy, (heterocycloalkyl)$C_0$-$C_2$alkyl, or (5- to 10-membered heteroaryl)$C_0$-$C_4$alkyl, each of which is optionally substituted.

$R_{10}$, $R_{11}$, and $R_{12}$ are independently at each occurrence hydrogen or trifluoromethyl, or $C_1$-$C_6$alkyl, $C_2$-$C_6$alkenyl, $C_2$-$C_6$alkynyl, (aryl)$C_0$-$C_2$alkyl, ($C_3$-$C_7$cycloalkyl)$C_0$-$C_2$alkyl, ($C_3$-$C_7$cycloalkenyl)$C_0$-$C_2$alkyl, (heterocycloalkyl)$C_0$-$C_2$alkyl, or (5- to 10-membered heteroaryl)$C_0$-$C_2$alkyl, each of which is optionally substituted.

$R_{13}$ is hydrogen or $C_1$-$C_2$alkyl.

$R_{14}$ and $R_{15}$ are independently hydrogen, hydroxyl, or $C_1$-$C_2$alkyl.

n is 0, 1, or 2.

M is hydrogen, halogen, hydroxyl, $C_1$-$C_2$alkyl, or $C_1$-$C_2$alkoxy,

Y is absent, $CR_{18}R_{19}$, $NR_{20}$, S, O, —O(C=O)($NR_{20}$)—, NH(C=O)($NR_{20}$)—, —NH(S=O)($NR_{20}$)—, —($NR_{20}$)(C=O)—, or —O(C=O)—; or Y is taken together with one of J, L, or M to form a ring.

J is $CH_2$ or J is taken together with Y to form a 3- to 7-membered carbocyclic or heterocyclic ring, which ring is substituted with 0 or 1 or more substituents independently chosen from halogen, hydroxy, amino, cyano, $C_1$-$C_2$alkyl, $C_1$-$C_2$alkoxy, $C_1$-$C_2$alkoxy, trifluoromethyl, and trifluoromethoxy; when J is taken together with Y to form a ring Z may be absent.

L is $CH_2$ or L is taken together with Y to form a 3- to 7-membered carbocyclic or heterocyclic ring, which ring is substituted with 0 or 1 or more substituents independently chosen from halogen, hydroxy, amino, cyano, $C_1$-$C_2$alkyl, $C_1$-$C_2$alkoxy, $C_1$-$C_2$alkoxy, trifluoromethyl, and trifluoromethoxy; when L is taken together with Y to form a ring Z may be absent.

Z is (mono-, bi-, or tri-cyclic aryl)$C_0$-$C_2$alkyl or (mono-, bi-, or tri-cyclic heteroaryl)$C_0$-$C_2$alkyl, each of which Z is substituted with 0 or 1 or more substituents independently chosen from halogen, hydroxyl, amino, cyano, —$CONH_2$, —COOH, —$SO_2NR_{11}R_{12}$, —(C=O)$NR_{11}R_{12}$, —$NR_{11}$(C=O)$R_{12}$, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, and 0 or 1 ($C_3$-$C_7$cycloalkyl)$C_0C_2$alkyl, (phenyl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, naphthyl, indanyl, (5- or 6-membered heterocycloalkyl)$C_0$-$C_2$alkyl, or 9- or 10-membered bicyclic heteroaryl, each of which is substituted with 0, 1, or 2 substituents independently chosen from:

(c) halogen, hydroxyl, amino, cyano, nitro, —COOH, —$CONH_2$, $CH_3$(C=O)NH—, =NOH, $C_1$-$C_4$alkyl, $C_1$-$C_4$alkoxy, $C_1$-$C_4$hydroxyalkyl, mono- and di-$C_1$-$C_4$alkylamino, —$NR_8SO_2R_{11}$, —C(O)O$R_{11}$, —$NR_8COR_{11}$, —$NR_8C(O)OR_{11}$, trifluoromethyl, and trifluoromethoxy, and (d) phenyl and 5- or 6-membered heteroaryl, each of which is substituted with 0 or 1 or more of halogen, hydroxyl, $C_1$-$C_4$alkyl, and $C_1$-$C_2$alkoxy.

$R_{16}$ represents 0 to 4 substituents is independently chosen at from halogen, $C_1$-$C_2$alkyl, and $C_1$-$C_2$alkoxy.

$R_{18}$ and $R_{19}$ are independently hydrogen, hydroxyl, halogen, $C_1$-$C_2$alkyl, $C_1$-$C_2$alkoxy, $C_1$-$C_2$haloalkyl, or $C_1$-$C_2$haloalkoxy, $R_{20}$ is hydrogen, $C_1$-$C_2$alkyl, $C_1$-$C_2$haloalkyl, or $C_1$-$C_2$haloalkoxy.

The invention particularly includes compounds of Formula I in which one of the following conditions is met (1) $R_1$ and $R_2$ are joined to form a substituted 4-membered heterocyclic ring containing 0 or 1 additional N, S, or O atoms, or an optionally substituted 4-membered heterocyclic ring containing 0 or 1 additional N, S, or O atoms fused to an optionally substituted 5- to 7-membered carbocyclic or heterocyclic ring.

(2) At least one of $R_3$, $R_4$, $R_5$, $R_6$, $R_7$, and $R_8$ is (heteroaryl) $C_0$-$C_4$alkyl or (aryl)$C_0$-$C_4$alkyl.

(3) Z is a (tricyclic aryl)$C_0$-$C_2$alkyl or (tri cyclic heteroaryl) $C_0$-$C_2$alkyl.

(4) $R_1$ and $R_2$ are taken together to form an optionally substituted 5- to 9-membered bridged heterocyclic ring containing 0, 1, or 2 additional N, S, or O atoms, or an optionally substituted 5- to 7-membered heterocyclic ring containing 0 or 1 additional N, S, or O atoms fused to an optionally substituted 5- to 7-membered carbocyclic or heterocyclic ring; or $R_1$ and $R_2$ are taken together to form an optionally substituted 4- to 7-membered heterocyclic ring containing 0 or 1 additional N, S, or O atoms fused to an optionally substituted 5- to 9-membered bridged carbocyclic or heterocyclic ring; or $R_1$ and $R_2$ are taken together to form an optionally substituted bicyclic system with rings in spiro orientation having a total of 6 to 12 ring atoms with 0, 1 or 2 additional heteroatoms independently chosen from N, O, and S with remaining ring atoms being carbon.

(5) —($NR_{20}$)(C=O)—.

Certain compounds of Formula I disclosed herein exhibit good activity in an HCV replication assay, such as the HCV replicon assay set forth in Example 7, which follows. Preferred compounds of Formula I exhibit an $EC_{50}$ of about 10 micromolar or less, or more preferably an $EC_{50}$ of about 1 micromolar or less; or still more preferably an $EC_{50}$ of about 10 nanomolar or less in an HCV replicon replication assay

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well hydrates of the compound and all pharmaceutically acceptable salts of the compound.

The term "4-amino-4-oxobutanoyl peptides" encompasses all compounds that satisfy Formula I, including any enantiomers, racemates and stereoisomers, as well as all pharmaceutically acceptable salts of such compounds. The phrase "a compound of Formula I" includes all subgeneric groups of Formula I including Formula IA, and Formula II and III as well as all forms of such compounds, including salts and hydrates, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

A dash ("-") that is not between two letters or symbols is used to indicate a point of attachment for a substituent. For example, —(CH$_2$)C$_3$-C$_8$cycloalkyl is attached through carbon of the methylene (CH$_2$) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

A bond represented by a combination of a solid and dashed line, ie., ====, may be either a single or double bond.

"Alkyl" is a branched or straight chain saturated aliphatic hydrocarbon group, having the specified number of carbon atoms, generally from 1 to about 12 carbon atoms. The term C$_1$-C$_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. C$_1$-C$_8$alkyl, C$_1$-C$_4$alkyl, and C$_1$-C$_2$alkyl. When C$_0$-C$_n$ alkyl is used herein in conjunction with another group, for example, (aryl)C$_0$-C$_4$ alkyl, the indicated group, in this case aryl, is either directly bound by a single covalent bond (C$_0$), or attached by an alkyl chain having the specified number of carbon atoms, in this case 1, 2, 3, or 4 carbon atoms. C$_0$-C$_n$- alkyl is used in conjunction with heteroaryl, aryl, phenyl, cycloalkyl, and heterocycloalkyl, e.g, (5- to 10-membered heteroaryl)C$_0$-C$_2$alkyl, (aryl)C$_0$-C$_2$alkyl, (phenyl)C$_0$-C$_2$alkyl, (C$_3$-C$_7$cycloalkyl)C$_0$-C$_4$alkyl, and (heterocycloalkyl)C$_0$-C$_4$alkyl. Examples of alkyl include, but are not limited to, methyl, ethyl, n-propyl, isopropyl, n-butyl, 3-methylbutyl, t-butyl, n-pentyl, and sec-pentyl.

"Alkenyl" indicates a straight or branched hydrocarbon chain comprising one or more unsaturated carbon-carbon double bonds, which may occur in any stable point along the chain. Alkenyl groups described herein have the indicated number of carbon atoms. E.g. C$_2$-C$_6$alkenyl indicates an alkenyl group of from 2, 3, 4, 5, or 6 carbon atoms. When no number of carbon atoms is indicated, alkenyl groups described herein typically have from 2 to about 12 carbon atoms, though lower alkenyl groups, having 8 or fewer carbon atoms, are preferred. Examples of alkenyl groups include ethenyl, propenyl, and butenyl groups.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "C$_0$-C$_n$alkoxy" is used in with another group, for example, (heteroaryl)C$_0$-C$_4$ alkoxy, the indicated group, in this case heteroaryl, is either attached via a covalently bound oxygen bridge (C$_0$alkoxy), or attached by an alkoxy group having the specified number of carbon atoms, in this case from 1 to about 4 carbon atoms, that is covalently bound to the group it substitutes via the alkoxy oxygen atom.

The term "alkylester" indicates an alkyl group as defined herein attached through an ester linkage. The ester linkage may be in either orientation, e.g. a group of the formula —O(C=O)alkyl or a group of the formula —(C=O)Oalkyl.

"Alkylthio" means alkyl-S—, where the alkyl group is an alkyl group as defined herein having the indicated number of carbon atoms and the point of attachment of the alkylhio substituent is on the sulfur atom. An exemplary alkylthio group is methylthio.

"Aryl" indicates an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "(aryl)alkyl," aryl and alkyl are as defined above, and the point of attachment is on the alkyl group. "(Aryl)C$_0$-C$_4$alkyl" indicates an aryl group that is directly attached via a single covalent bond (aryl)C$_0$alkyl or attached through an alkyl group having from 1 to about 4 carbon atoms. Examples of (aryl)alkyl groups include piperonyl and (phenyl)alkyl groups such as benzyl and phenylethyl. Similarly, the term "(aryl)C$_0$-C$_4$alkoxy" indicates an aryl group that is directly attached to the molecule it substitutes via an oxygen bridge, e.g. (aryl)C$_0$alkoxy, or covalently bound to an alkoxy group having from 1 to 4 carbon atoms.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane. Likewise "cycloalkenyl" is a hydrocarbon ring group having the indicated number of carbon atoms and at least carbon-carbon double between ring carbon atoms.

The terms "(cycloalkyl)$C_0$-$C_n$alkyl" indicates a substituent in which the cycloalkyl and alkyl are as defined herein, and the point of attachment of the (cycloalkyl)alkyl group to the molecule it substitutes is either a single covalent bond, ($C_0$alkyl) or on the alkyl group. (Cycloalkyl)alkyl encompasses, but is not limited to, cyclopropylmethyl, cyclohexylmethyl, and cyclohexylmethyl.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d] oxazolyl, benzofuranyl, benzothiazolyl, benzothiophenyl, benzoxadiazolyl, dihydrobenzodioxynyl, furanyl, imidazolyl, indolyl, and isoxazolyl.

The term "heterocycloalkyl" indicates a saturated monocyclic group having the indicated number of ring atoms and containing from 1 to about 3 heteroatoms chosen from N, O, and S, with remaining ring atoms being carbon, or a saturated bicyclic ring system having at least one N, O, or S ring atom with the remaining atoms being carbon. Monocyclic heterocycloalkyl groups usually have from 4 to about 8 ring atoms. In some embodiments monocyclic heterocyloalkyl groups have from 5 to 7 ring atoms. Bicyclic heterocycloalkyl groups typically have from about five to about 12 ring atoms. Examples of heterocycloalkyl groups include morpholinyl, piperazinyl, piperidinyl, and pyrrolidinyl groups.

The term "(heterocycloalkyl)alkyl" indicates a saturated substituent in which the heterocycloalkyl and alkyl are as defined herein, and the point of attachment of the (heterocycloalkyl)alkyl group to the molecule it substitutes is on the alkyl group. This term encompasses, but is not limited to, piperidylmethyl, piperazinylmethyl, and pyrrolidinylmethyl.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarboxamide" indicates a monoalkylcarboxamide group of formula (alkyl1)-NH—(C=O)— or a dialkylcarboxamide group of the formula (alkyl1)(alkyl2)-N—(C=O)— in which the point of attachment of the mono- or dialkylcarboxamide substituent to the molecule it substitutes is on the carbon of the carbonyl group. The term "mono and/or di-alkylcarboxamide" also includes groups of the formula (alkyl1)(C=O)NH— and (alkyl1)(C=O)(alkyl2)N— in which the point of attachment is the nitrogen atom. The groups alkyl1 and alkyl2 are independently chosen alkyl groups having the indicated number of carbon atoms.

"Oxo," means a keto group (C=O). An oxo group that is a substituent of a nonaromatic carbon atom results in a conversion of —$CH_2$— to —C(=O)—. An oxo group that is a substituent of an aromatic carbon atom results in a conversion of —CH— to —C(=O)— and a loss of aromaticity.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions of the invention refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient having or susceptible to a hepatitis C infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where p<0.05.

Chemical Description

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. R, $R_1$-$R_8$, $R_{16}$, $R_{18}$, $R_{19}$, M, n, T, Y, and Z. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

In addition to compounds of Formula I as described above, the invention also includes compounds of Formula I in which one or more of the following conditions is met for the variables Formula I. The invention includes compounds of Formula I or Formula IA, Formula II (Formula IA, II and III are subgeneric groups Formula of I) that carry any combination of the variable definitions set forth below that results in a stable compound.

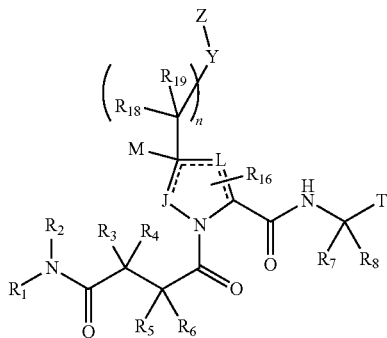

Formula I

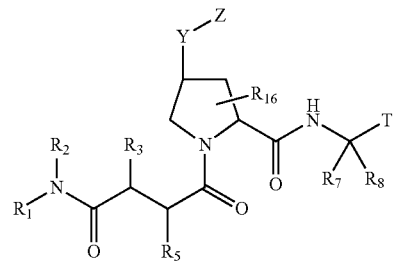

Formula IA

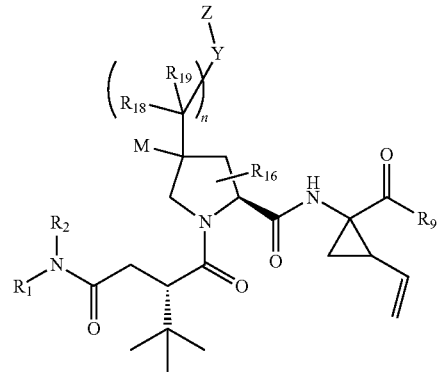

Formula II

For example, the invention includes embodiments in which any one or more of the following conditions are met, so long as a stable compound results.

The $R_1$ and $R_2$ Substituents

The invention includes embodiments in which $R_1$ and $R_2$ carry any of the following definitions.

(a) $R_1$ and $R_2$ form an optionally substituted azetidine ring.

(b) $R_1$ and $R_2$ for an azetidine ring that is unsubstituted, or substituted with 1 or 2 halogen atoms or phenyl substituted with 0 to 3 substituents independently chosen from halogen, methyl, and methoxy.

(c) $R_1$ and $R_2$ are joined to form a 5- to 7-membered heterocyloalkyl ring containing 1 or 2 heteroatoms independently chosen from N, O, and S which ring is optionally fused to a phenyl or 5- or 6-membered heteroaryl to form a bicyclic ring system, each of which 5- to 7-membered heterocycloalkyl ring or bicyclic ring system is optionally substituted.

(d) Any heterocycloalkyl ring formed by $R_1$ and $R_2$ may be substituted with 0 to 2 substituents independently chosen from chloro, fluoro, hydroxyl, COOH, —$CONH_2$, oxo, $C_1$-$C_4$alkyl, $C_1$-$C_4$alkoxy, mono- or di-$C_1$-$C_4$alkylamino, trifluoromethyl, (mono- or di-$C_1$-$C_4$alkylcarbamate)$C_0$-$C_2$alkyl-, $C_1$-$C_4$alkylester, mono- or di-$C_1$-$C_4$alkylcarboxamide phenyl, benzyl, pyridyl, 5-fluorobenzo[d]imidazol-2-yl, and a group of the formula

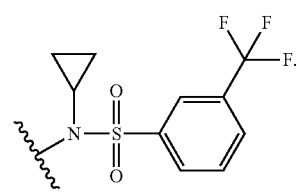 [SMILES: *N(C1CC1)S(=O)(=O)c1cccc(C(F)(F)F)c1]

(e) $R_1$ and $R_2$ are joined to form a pyrrolidine, piperidine, or piperazine ring, or a piperazine ring fused to a phenyl or cyclohexyl ring, each of which is optionally substituted with 0 to 2 substituents independently chosen from halogen, oxo hydroxyl, amino, $CONH_2$, —COOH, $C_1$-$C_2$alkyl, $C_1$-$C_2$alkoxy, trifluoromethyl, mono- and di-$C_1$-$C_4$alkylcarboxamide, and mono- and di-$C_1$-$C_4$alkylcarbamate.

(f) $R_1$ and $R_2$ are joined to form a 4- to 7-membered heterocyloalkyl ring containing 0 to 2 additional heteroatoms independently chosen from N, O, and S which ring is optionally fused to a 5- or 6-membered heterocyclic ring, containing 1 or 2 heteroatoms independently chosen from N, O, and S, or 5- or 6-membered carbocyclic ring to form a bicyclic ring system, each of which 5- to 7-membered heterocycloalkyl ring or bicyclic ring system is substituted with 0 to 3 substituents independently chosen from A- and AB-, where A is halogen, hydroxyl, amino, cyano, oxo, —$CONH_2$, —COOH, $C_1$-$C_4$alkyl, $C_2$-$C_4$alkanoyl, $C_1$-$C_4$alkoxy, $C_1$-$C_4$alkylthio, mono- or di-$C_1$-$C_4$alkylamino, $C_1$-$C_4$alkylester, mono- or di-$C_1$-$C_4$alkylcarbamate, mono- or di-$C_1$-$C_4$alkylcarboxamide, $C_1$-$C_4$alkylsulfonyl, $C_1$-$C_4$alkylsulfonamide, $C_1$-$C_2$haloalkyl, $C_1$-$C_2$haloalkoxy, pyridyl, pyrimidinyl, and phenyl, which pyridyl, pyrimidinyl and phenyl are substituted with 0 to 2 substituents independently chosen halogen, methyl and methoxy; and B is $C_1$-$C_4$alkyl;

each of which 5- to 7-membered heterocycloalkyl ring or bicyclic ring system is also substituted with 0 or 1 substituents chosen from N-cyclopropyl-3-(trifluoromethyl)phenylsulfonamido, thiazol-2-ylcarbamoyl, 5-phenyl-1H-pyrazol-3-yl, and benzimidazolyl optionally substituted with halogen; or $R_1$ and $R_2$ are taken together to form a 5- to 6-membered partially unsaturated or aromatic group that is optionally fused to a phenyl or pyridyl group, which is substituted with 0 to 3 substituents independently chosen from halogen, —$CONH_2$, $C_1$-$C_2$alkyl, $C_1$-$C_2$alkoxy, and trifluoromethyl.

(g) $R_1$ and $R_2$ are joined to form a pyrrolidine, piperidine, or piperazine ring, or a piperazine ring fused to a phenyl, each of which is optionally substituted with 0 to 2 substituents independently chosen from methyl, —$CONH_2$ and fluoro.

(h) $R_1$ is

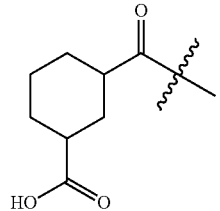

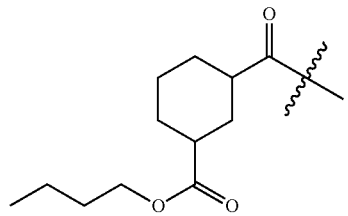

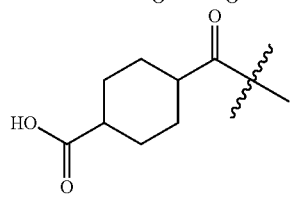

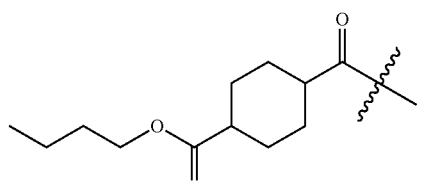

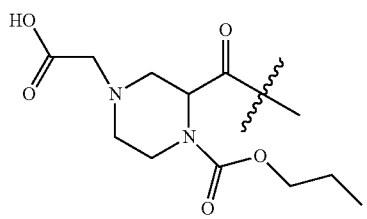

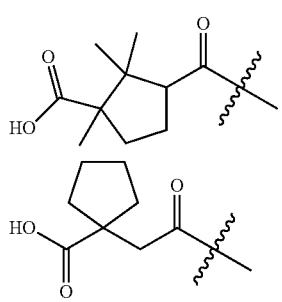

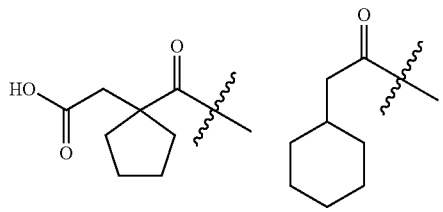

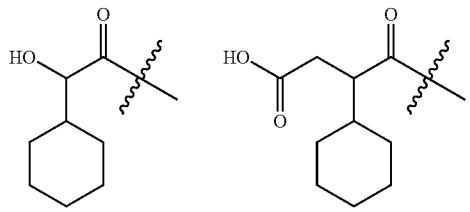

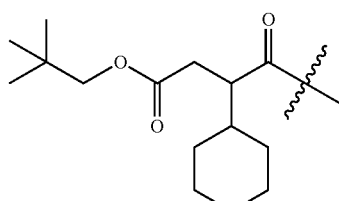

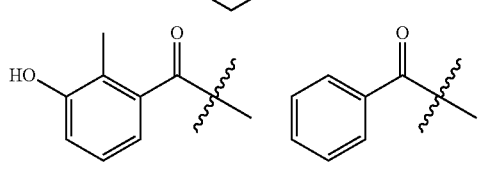

-continued

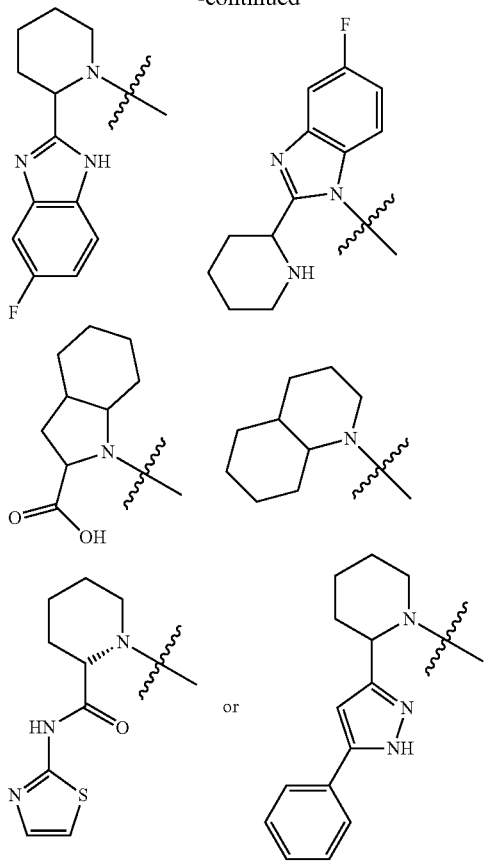

(i) $R_1$ and $R_2$ are taken together to form an azetidinyl ring substituted with 0 to 2 halogen substituents and 0 or 1 phenyl substituent.

(j) $R_1$ carries any of the definitions set forth in (e) above, and $R_2$ is $C_1$-$C_6$alkyl or $C_3$-$C_7$cycloalkyl.

(k) $R_1$ carries any of the definitions set forth in (e) above, and $R_2$ is hydrogen.

(l) $R_1$ and $R_2$ are taken together to form an azetidinyl, pyrrolidinyl, pyrazolidinyl, imidazolidinyl, oxazolidinyl, piperidinyl, piperazinyl, morpholinyl, azepanyl, octohydroquinolinyl, octohydroisoquinolinyl, dihydroquinolinyl, dihydroisoquinolinyl, octohydroindolyl, 1,4-dioxa-8-azaspiro[4.5]decan-8-yl, or octohydroisoindolyl, each of which is substituted with 0, 1, or 2 substituents independently chosen from chloro, fluoro, hydroxyl, COOH, —$CONH_2$, oxo, $C_1$-$C_4$alkyl, $C_1$-$C_4$alkoxy, mono- or di-$C_1$-$C_4$alkylamino, trifluoromethyl, (mono- or di-$C_1$-$C_4$alkylcarbamate)$C_0$-$C_2$alkyl-, $C_1$-$C_4$alkylester, mono- or di-$C_1$-$C_4$alkylcarboxamide phenyl, benzyl, pyridyl, 5-fluorobenzo[d]imidazol-2-yl, and a group of the formula

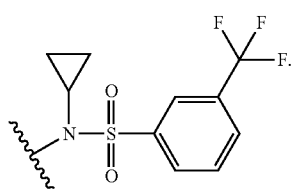 [SMILES: *N(C1CC1)S(=O)(=O)c1cccc(C(F)(F)F)c1]

(m) $R_1$ and $R_2$ are taken together to form a piperazinyl, morpholinyl, or piperidinyl group, each bridged with a methylene, ethylene, or oxygen bridge, or $R_1$ and $R_2$ are taken together to form a decahydroquinolinyl or decahydroisoquinolinyl group, each of which is bridged with a methylene, ethylene, or oxygen bridge; or $R_1$ and $R_2$ are taken together to form a 5- or 6-membered heterocycloalkyl group chosen from piperazinyl, morpholinyl, piperidinyl and pyrrolidinyl rings, each of which 5- or 6-membered heterocycloalkyl group is fused to a cyclohexyl group, which cyclohexyl group is bridged with a methylene, ethylene or oxygen bridge;

wherein each $R_1$ and $R_2$ group is substituted with 0 to 2 substituents independently chosen from oxo, halogen, —$CONH_2$, $C_1$-$C_2$alkyl, $C_1$-$C_2$alkoxy, and $C_1$-$C_4$alkyl carbamate.

(n) $R_1$ and $R_2$ are taken together to form a group of the formula:

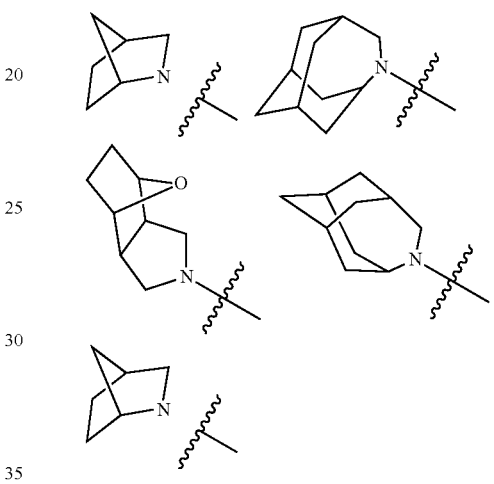

each of which is substituted with 0 to 2 substituents independently chosen from oxo, halogen, —$CONH_2$, $C_1$-$C_2$alkyl, $C_1$-$C_2$alkoxy, and $C_1$-$C_4$alkyl carbamate.

(o) $R_1$ and $R_2$ are taken together to form a bicyclic system with rings in spiro orientation having a total of 9 to 11 ring atoms with 0, 1 or 2 additional heteroatoms independently chosen from N, O, and S with remaining ring atoms being carbon, which spiro ring system is substituted with 0 to 2 substituents independently chosen from oxo, halogen, —$CONH_2$, $C_1$-$C_2$alkyl, and $C_1$-$C_2$alkoxy.

(p) R

The $R_3$ to $R_8$ Substituents (a) $R_3$ and $R_4$ are independently (1) hydrogen, or (2) $C_1$-$C_4$alkyl or ($C_3$-$C_7$cycloalkyl)$C_0$-$C_4$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

(b) $R_3$ is hydrogen or methyl and $R_4$ is hydrogen, $C_1$-$C_4$alkyl, or ($C_3$-$C_7$cycloalkyl)$C_0$-$C_4$alkyl.

(c) $R_3$ and $R_4$ are independently hydrogen or methyl.

(d) $R_3$ is hydrogen and $R_4$ is ($C_3$-$C_7$cycloalkyl)$C_0$-$C_2$alkyl or (heterocyloalkyl)$C_0$-$C_2$alkyl.

(e) $R_3$ is hydrogen or $C_1$-$C_4$alkyl, or ($C_3$-$C_6$cycloalkyl)$C_0$-$C_2$alkyl, and $R_4$ is hydrogen.

(f) $R_3$ and $R_4$ are both hydrogen.

(g) $R_5$ is (1) hydrogen, or (2) $C_1$-$C_6$alkyl, ($C_3$-$C_7$cycloalkyl)$C_0$-$C_2$alkyl, or (phenyl)$C_0$-$C_2$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy; and $R_6$ is hydrogen or methyl.

(h) $R_5$ is $C_1$-$C_6$alkyl, ($C_3$-$C_7$cycloalkyl)$C_0$-$C_2$alkyl, or (phenyl)$C_0$-$C_2$alkyl, each of which is unsubstituted; and $R_6$ is hydrogen or methyl.

(i) $R_5$ is hydrogen, $C_1$-$C_6$alkyl, ($C_3$-$C_6$cycloalkyl)$C_0$-$C_2$alkyl, phenyl, or benzyl, and $R_6$ is hydrogen.

(j) $R_5$ and $R_6$ are both hydrogen.

(k) $R_7$ is hydrogen or methyl; and $R_8$ is $C_1$-$C_4$alkyl, ($C_3$-$C_7$cycloalkyl)$C_0$-$C_4$alkyl, or (phenyl)$C_0$-$C_2$alkyl, each of which is substituted with 0 to 3 substituents independently chosen from halogen, hydroxyl, amino, cyano, —$CONH_2$, —COOH, $C_1$-$C_4$alkyl, $C_2$-$C_4$alkenyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

(l) $R_7$ is hydrogen or methyl, and $R_8$ is $C_1$-$C_4$alkyl, ($C_3$-$C_7$cycloalkyl)$C_0$-$C_2$alkyl, or (phenyl)$C_0$-$C_2$alkyl, each of which is unsubstituted; or $R_7$ and $R_8$ are joined to form a 3- to 7-membered cycloalkyl ring or 3- to 7-membered heterocycloalkyl ring containing 1 or 2 heteroatoms independently chosen from N, S, and O, each of which cyclolalkyl or heterocycloalkyl ring is substituted with 0 to 2 substituents independently chosen from halogen, hydroxyl, amino, cyano, vinyl, $C_1$-$C_2$alkyl, $C_2$-$C_4$alkenyl, $C_1$-$C_2$alkoxy, trifluoromethyl, and trifluoromethoxy.

(m) $R_7$ and $R_8$ are joined to form a vinyl-substituted cycloproyl group or a 4- to 6-membered cycloalkyl ring, substituted with 0 to 2 substituents independently chosen from halogen, hydroxyl, $C_1$-$C_2$alkyl, and $C_1$-$C_2$alkoxy.

(n) In certain embodiments $R_3$, $R_4$, and $R_6$, are independently hydrogen or methyl;

$R_5$ is $C_1$-$C_6$alkyl, ($C_3$-$C_7$cycloalkyl)$C_0$-$C_2$alkyl, or (phenyl)$C_0$-$C_2$alkyl, each of which is unsubstituted; and $R_7$ is hydrogen and $R_8$ is $C_1$-$C_4$alkyl or phenyl; or $R_7$ and $R_8$ are joined to form a vinyl-substituted cycloproyl group or a 4- to 6-membered cycloalkyl ring, substituted with 0 to 2 substituents independently chosen from halogen, hydroxyl, $C_1$-$C_2$alkyl, and $C_1$-$C_2$alkoxy.

(o) In certain other embodiments $R_3$, $R_4$, and $R_6$, are independently hydrogen or methyl;

$R_5$ is $C_1$-$C_6$alkyl, ($C_3$-$C_7$cycloalkyl)$C_0$-$C_2$alkyl, or (phenyl)$C_0$-$C_2$alkyl, each of which is unsubstituted; and $R_7$ is hydrogen and $R_8$ is $C_1$-$C_4$alkyl or phenyl; or $R_7$ and $R_8$ are joined to form a vinyl-substituted cycloproyl group or a 4- to 6-membered cycloalkyl ring, substituted with 0 to 2 substituents independently chosen from halogen, hydroxyl, $C_1$-$C_2$alkyl, and $C_1$-$C_2$alkoxy.

T and $R_9$ Substituents

The invention includes compounds and salts of Formula I in which T is a group of the formula

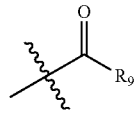

and $R_9$ carries any of the definitions which follow.

(a) $R_9$ is hydroxyl, amino, —COOH, —$NR_{10}R_{11}$, —$OR_{12}$, —$SR_{12}$, —$NR_{10}(S=O)R_{11}$, —$NR_{10}SO_2R_{11}$, —$NR_{10}SONR_{11}R_{12}$, —$NR_{10}SO_2NR_{11}R_{12}$, —(C=O)$OR_{10}$, —$NR_{10}$(C=O)$OR_{11}$, or —$CONR_{10}R_{11}$.

$R_9$ is hydroxyl, —$OR_{12}$, —$NR_{10}SO_2R_{11}$, or —$NR_{10}SO_2NR_{11}R_{12}$.

(b) $R_9$ is —$NR_{19}SO_2R_{11}$; in which $R_{10}$ is hydrogen or methyl; and $R_{11}$ is $C_1$-$C_6$alkyl, phenyl, $C_3$-$C_7$cycloalkyl, thienyl, or imidazolyl, each of which is substituted with 0 to 3 substituents independently chosen from halogen, $C_1$-$C_4$alkyl, $C_1$-$C_4$alkoxy, $C_2$-$C_4$alkenyl, phenyl, or benzyl.

(c) $R_9$ is —$NR_{10}SO_2R_{11}$; wherein $R_{10}$ is hydrogen and $R_{11}$ is $C_1$-$C_4$alkyl or cyclopropyl, which is unsubstituted or substituted with one substituent chosen from chloro, $C_1$-$C_4$alkyl, $C_2$-$C_4$alkenyl, or benzyl.

(d) The invention includes compounds of Formula I including compounds in which $R_9$ carries the definitions (a) and (b) set forth immediately above in which $R_{10}$ and $R_{12}$ are independently hydrogen or methyl and $R_{11}$ is trifluormethyl or $C_1$-$C_6$alkyl or $R_{11}$ is $C_3$-$C_6$cycloalkyl, phenyl, or benzyl, each of which is substituted with 0 to 2 substituents independently chosen from halogen, $C_1$-$C_4$alkyl, $C_1$-$C_4$alkoxy, $C_2$-$C_4$alkenyl, and (phenyl)$C_0$-$C_2$alkyl.

(e) In certain embodiments $R_{10}$ is hydrogen or methyl and $R_{11}$ is cyclopropyl.

The Y, n, J, and L Variables and M Substituent

The invention includes compounds and salts of Formula I in which any of the following conditions are met for Y, n, J, L, and M.

(a) In certain embodiments n is 0; and Y is absent, O, S, —O(C=O)—, or —O(C=O)($NR_{20}$)—, where $R_{20}$ is hydrogen or methyl.

(b) In certain other embodiments n is 0 and Y is O.

(c) The invention includes embodiments in which n is 0; and Y is —($NR_{20}$)(C=O)—, where $R_{20}$ is hydrogen or methyl.

(d) M is hydrogen (e) J and L are both $CH_2$.

The Z Substituent

The Z Substituent may have any of the following definitions.

(a) Z is 1-naphthyl, 2-napthyl,

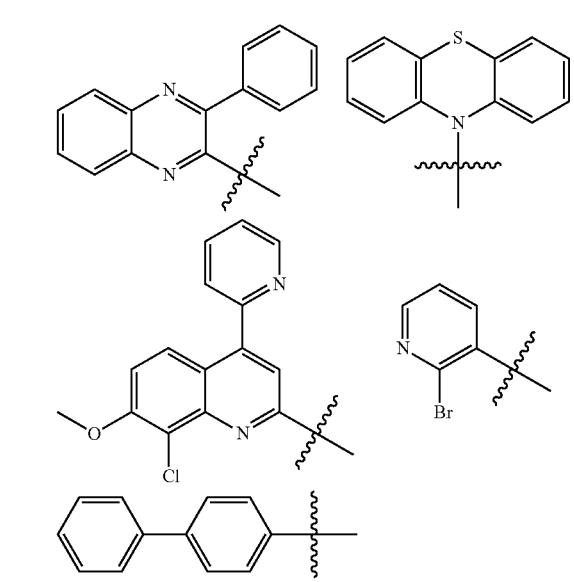

-continued
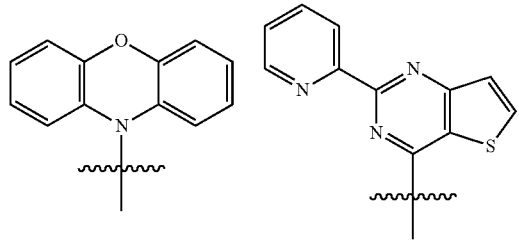
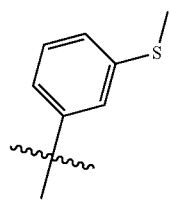
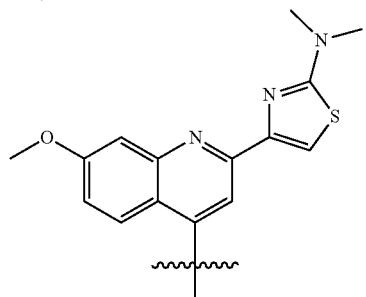
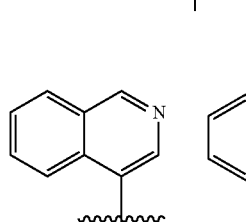
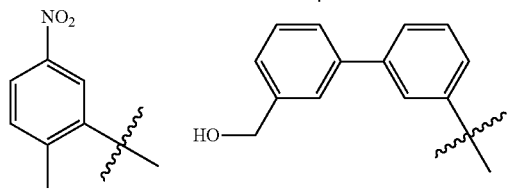
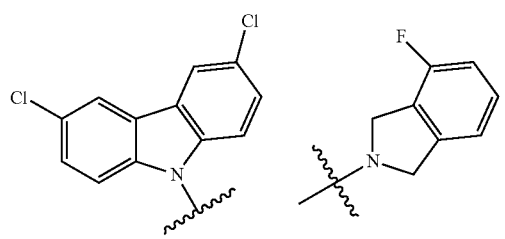
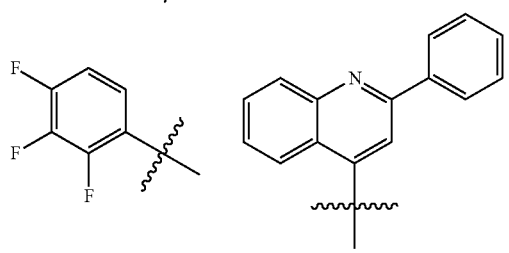
-continued
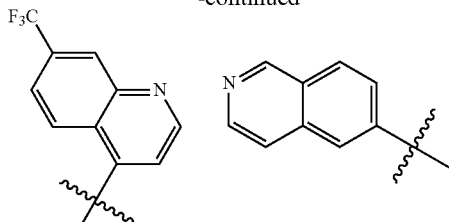
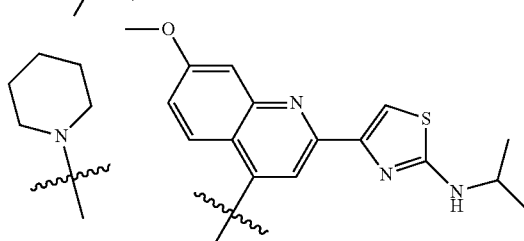
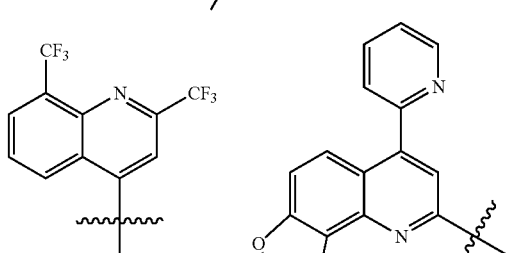
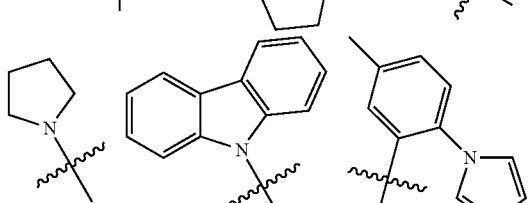
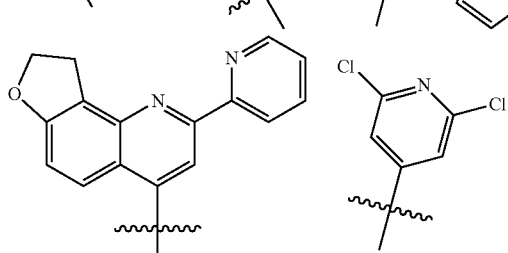
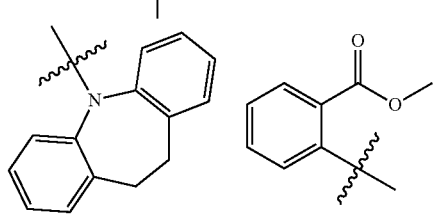
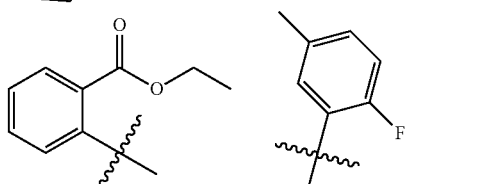
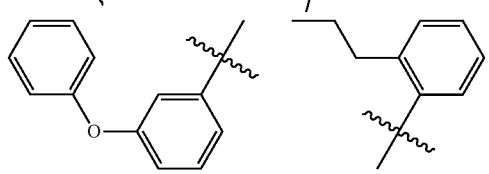

-continued
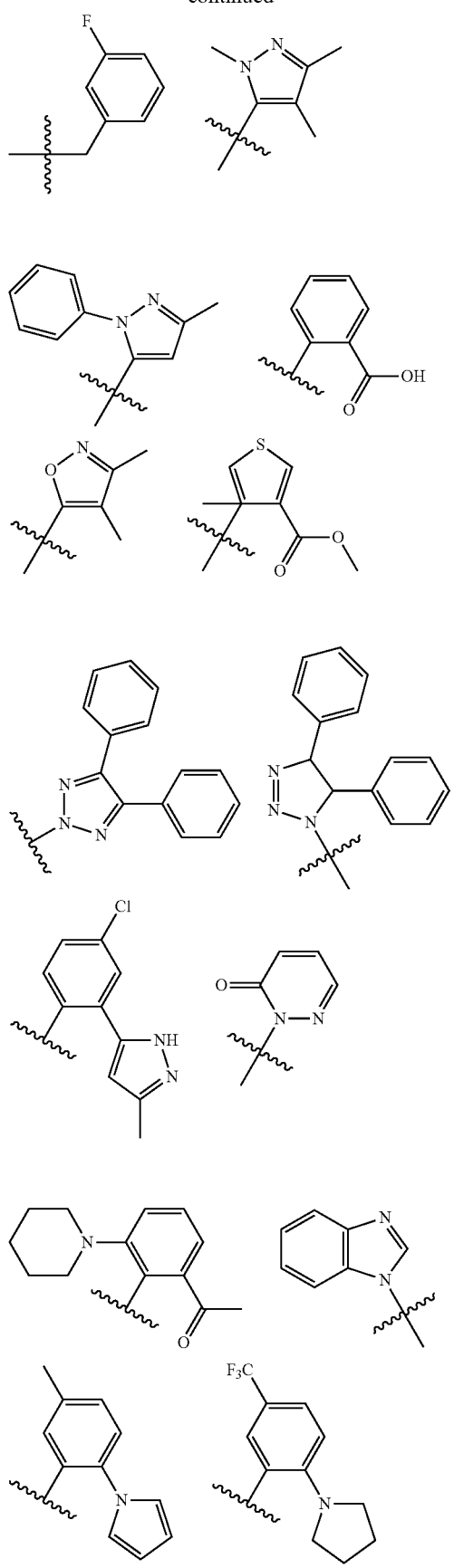
-continued
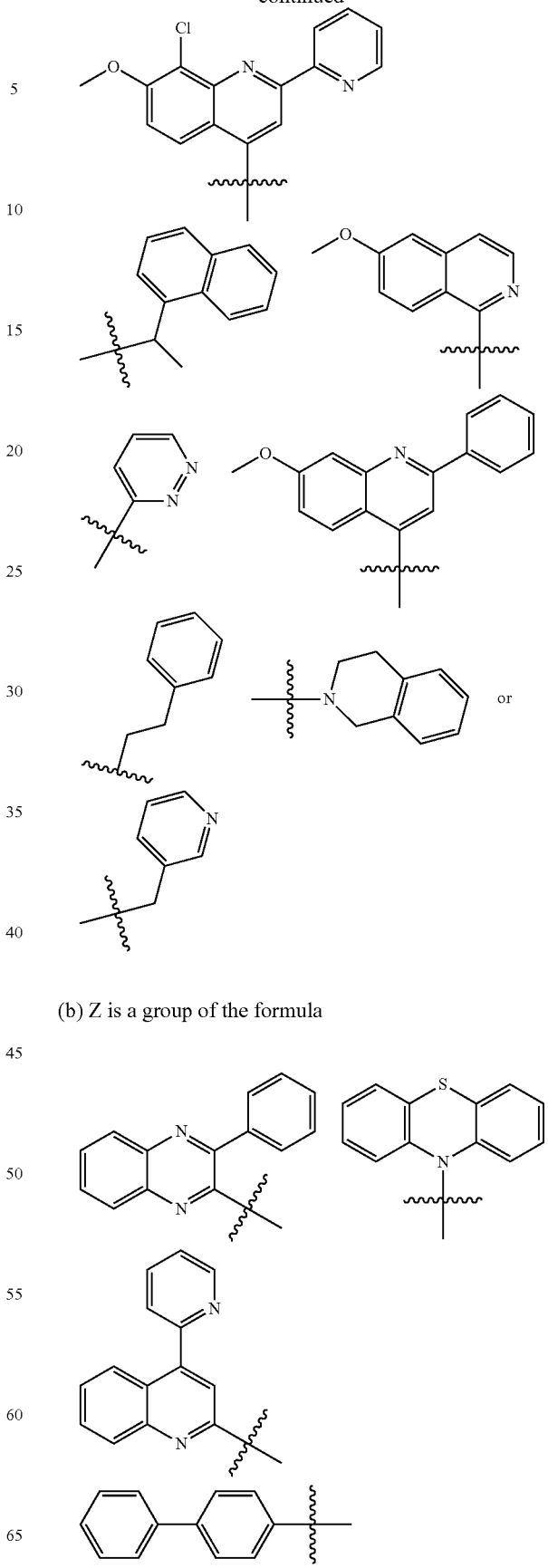
(b) Z is a group of the formula

-continued
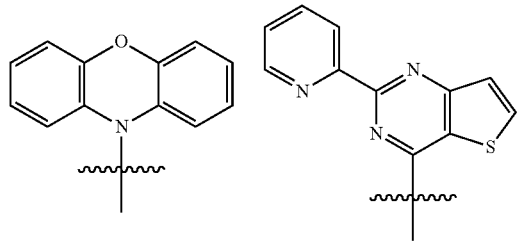
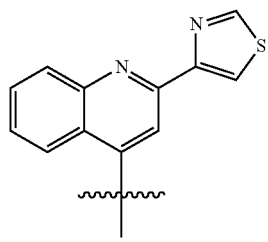
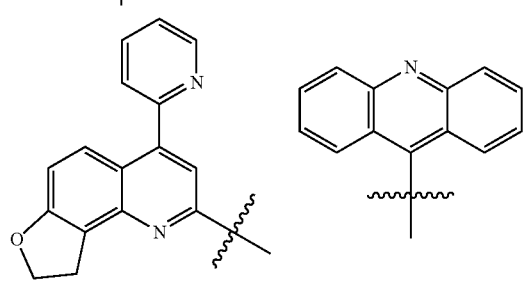
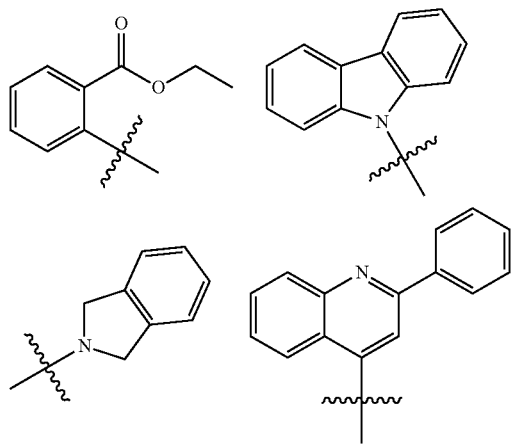
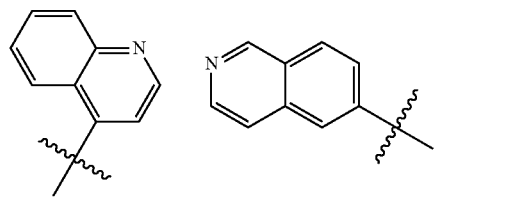
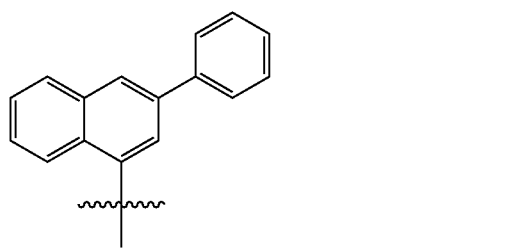
-continued
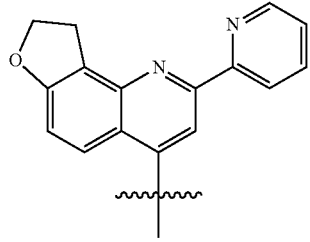
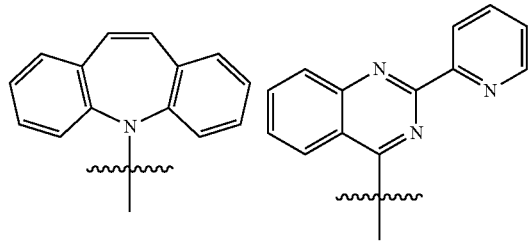
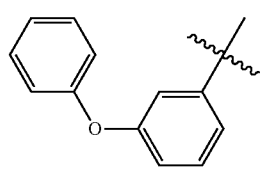
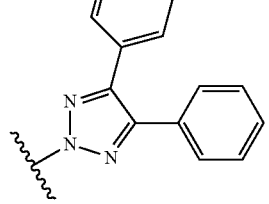
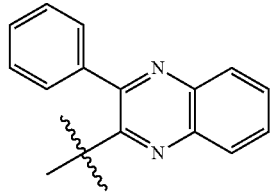
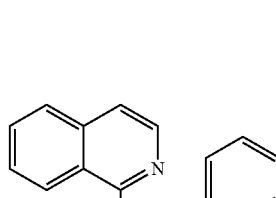
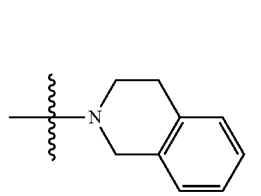
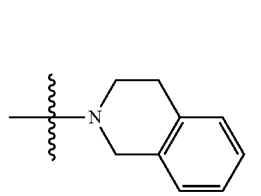
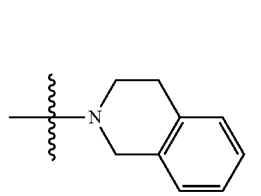

-continued

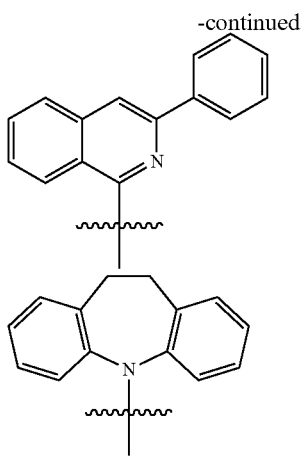

or

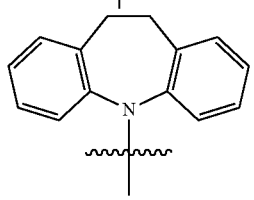

each of which is substituted by 0, 1, 2, or 3 substituents independently chosen from halogen, $C_1$-$C_4$alkyl, $C_1$-$C_4$alkoxy, and mono- and di-$C_1$-$C_4$alkylamino.

(c) Z is a group of the formula

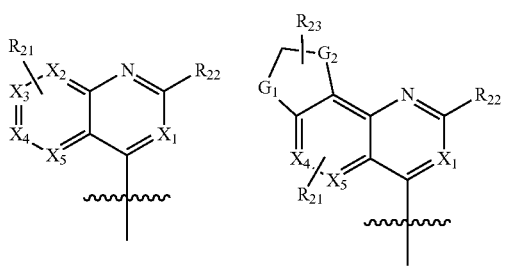

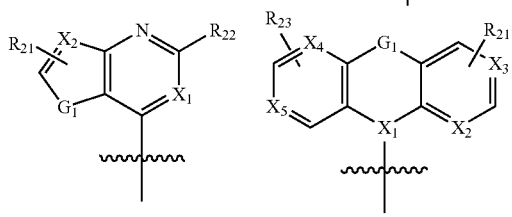

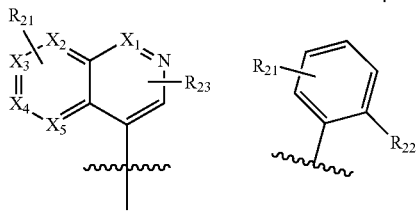

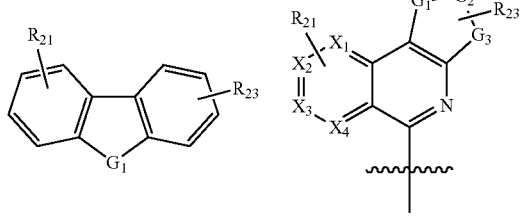

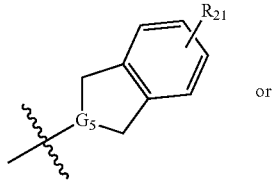 or

-continued

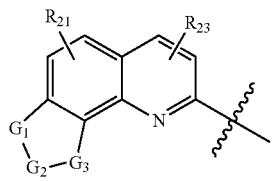

wherein $X_1$, $X_2$, $X_3$, $X_4$, and $X_5$ are independently N or CH and no more than two of $X_1$-$X_5$ are N.

$G_1$, $G_2$, $G_3$, and $G_4$ are independently $CH_2$, O, S, or $NR_{26}$, wherein no more than two of $G_1$ to $G_4$ are other than hydrogen; and $G_5$ is N or CH.

$R_{21}$ represents from 0 to 3 groups independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy, or $R_{22}$ is ($C_3$-$C_7$cycloalkyl)$C_0$-$C_2$alkyl, (phenyl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, naphthyl, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from:

(1) halogen, hydroxyl, amino, cyano, nitro, —COOH, —$CONH_2$, $CH_3$(C=O)NH—, $C_1$-$C_4$alkyl, $C_1$-$C_4$alkoxy, $C_1$-$C_4$hydroxyalkyl, mono- and di-$C_1$-$C_4$alkylamino, —$NR_8SO_2R_{11}$, —C(O)$OR_{11}$, —$NR_8COR_{11}$, —$NR_8C(O)OR_{11}$, trifluoromethyl, trifluoromethoxy, and (2) phenyl and 5- or 6-membered heteroaryl, each of which is substituted with 0 or 1 or more of halogen, hydroxyl, $C_1$-$C_4$alkyl, $C_1$-$C_2$alkoxy;

$R_{23}$ is 0 to 2 substituents independently chosen from halogen, hydroxyl, $C_1$-$C_2$alkyl, and $C_1$-$C_2$alkoxy.

$R_{24}$ is independently chosen at each occurrence from hydrogen and $C_1$-$C_2$alkyl.

(d) Z is a group of the formula

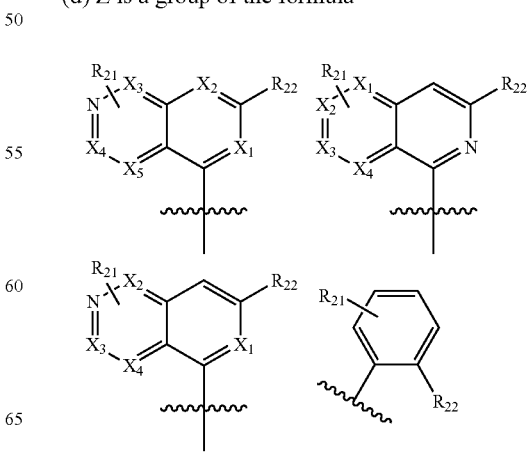

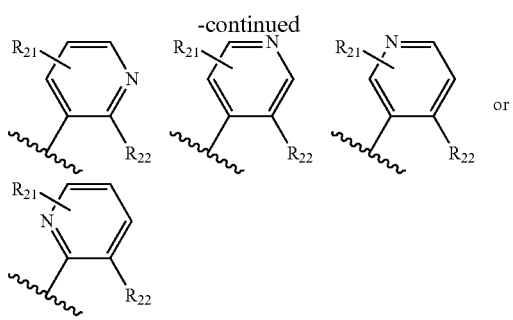

wherein $X_1$, $X_2$, $X_3$, and $X_4$, are independently N or CH and no more than two of $X_1$-$X_4$ are N.

$R_{21}$ represents from 0 to 3 groups independently chosen from halogen, hydroxyl, amino, cyano, —CONH$_2$, —COOH, C$_1$-C$_4$alkyl, C$_2$-C$_4$alkanoyl, C$_1$-C$_4$alkoxy, C$_1$-C$_4$alkylthio, mono- and di-C$_1$-C$_4$alkylamino, C$_1$-C$_2$haloalkyl, and C$_1$-C$_2$haloalkoxy.

$R_{22}$ is hydrogen, halogen, hydroxyl, amino, cyano, —CONH$_2$, —COOH, C$_1$-C$_4$alkyl, C$_2$-C$_4$alkanoyl, C$_1$-C$_4$alkoxy, C$_1$-C$_4$alkylthio, mono- and di-C$_1$-C$_4$alkylamino, C$_1$-C$_4$alkylester, C$_1$-C$_2$haloalkyl, and C$_1$-C$_2$haloalkoxy, or $R_{22}$ is (C$_3$-C$_7$cycloalkyl)C$_0$C$_2$alkyl, (phenyl)C$_0$-C$_2$alkyl, (phenyl)C$_0$-C$_2$alkoxy, (5- or 6-membered heteroaryl)C$_0$-C$_2$alkyl, (5- or 6-membered heteroaryl)C$_0$-C$_2$alkoxy, naphthyl, indanyl, (5- or 6-membered heterocycloalkyl)C$_0$C$_2$alkyl, or 9- or 10 membered bicyclic heteroaryl, each of which is substituted with 0, 1, or 2 substituents independently chosen from (1) halogen, hydroxyl, amino, cyano, nitro, —COOH, —CONH$_2$, CH$_3$(C═O)NH—, C$_1$-C$_4$alkyl, C$_1$-C$_4$alkoxy, C$_1$-C$_4$hydroxyalkyl, mono- and di-C$_1$-C$_4$alkylamino, —NR$_8$SO$_2$R$_{11}$, —C(O)OR$_{11}$, —NR$_8$COR$_{11}$, —NR$_8$C(O)OR$_{11}$, trifluoromethyl, and trifluoromethoxy, and (2) phenyl and 5- or 6-membered heteroaryl, each of which is substituted with 0 or 1 or more of halogen, hydroxyl, C$_1$-C$_4$alkyl, C$_1$-C$_2$alkoxy.

(e) Z is a group of the formula

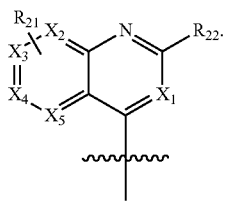

(f) Z is a quinoline of the formula

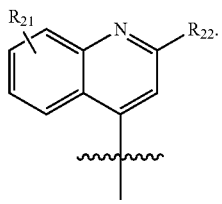

(g) In certain embodiments Z is a quinoline of the formula given in (f) and the variables $R_{21}$ and $R_{22}$ in Z carry the following definitions:

$R_{21}$ represents a substituent at the 7-position of the quinoline, and 0 to 2 additional substituents independently chosen from halogen, hydroxyl, amino, cyano, —CONH$_2$, —COOH, C$_1$-C$_4$alkyl, C$_2$-C$_4$alkanoyl, C$_1$-C$_4$alkoxy, mono- and di-C$_1$-C$_4$alkylamino, C$_1$-C$_2$haloalkyl, and C$_1$-C$_2$haloalkoxy; and $R_{22}$ is (phenyl)C$_0$-C$_2$alkyl or (pyridyl)C$_0$-C$_2$alkyl, each of which is substituted with 0, 1, or 2 substituents independently chosen from halogen, hydroxyl, amino, cyano, —COOH, —CONH$_2$, C$_1$-C$_4$alkyl, C$_1$-C$_4$alkoxy, mono- and di-C$_1$-C$_4$alkylamino, trifluoromethyl, and trifluoromethoxy.

(h) In other embodiments $R_{21}$ is a methoxy or ethoxy substituent at the 7-position of the quinoline and $R_{22}$ is phenyl or pyridyl.

(i) Z is

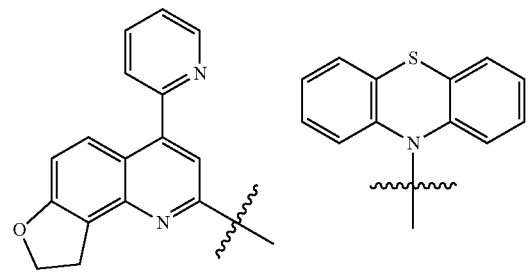

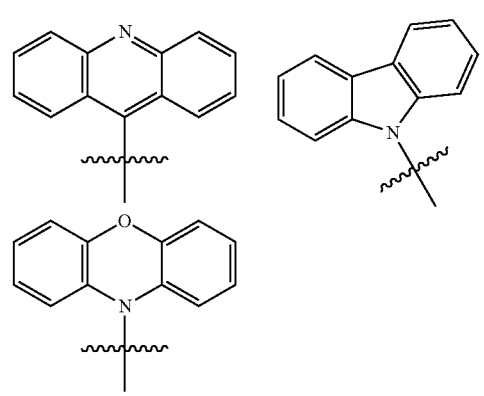

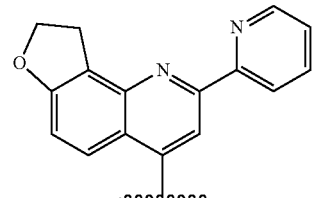

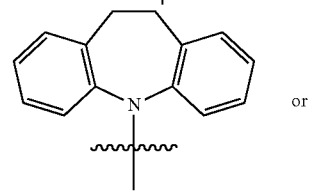 or

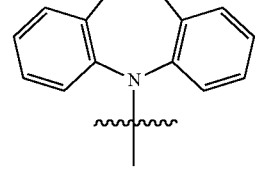

each of which is substituted by 0, 1, 2, or 3 substituents independently chosen from halogen, $C_1$-$C_4$alkyl, $C_1$-$C_4$alkoxy, and mono- and di-$C_1$-$C_4$alkylamino.

The invention includes compounds of Formula III (which is a subgeneric group of Formula I)

Formula III

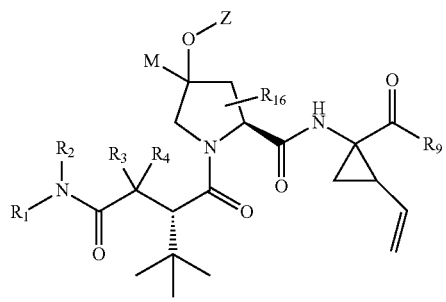

Within Formula III the following conditions are met.

$R_1$ and $R_2$ are joined to form an azetidine, pyrrolidine, piperidine, or piperazine ring or a piperazine ring fused to a phenyl, each of which is optionally substituted with 0 to 2 substituents independently chosen from halogen, hydroxyl, amino, $CONH_2$, $C_1$-$C_4$alkyl(C=O)—COOH, $C_1$-$C_2$alkyl, and $C_1$-$C_2$alkoxy.

$R_3$, $R_4$, $R_6$, and $R_8$ are independently chosen from hydrogen, $C_1$-$C_4$alkyl, and ($C_3$-$C_7$cycloalkyl)$C_0$-$C_2$alkyl.

$R_9$ is hydroxyl, amino, —COOH, —$NR_{10}R_{11}$, —$OR_{12}$, —$NR_{10}SO_2R_{11}$, —(C=O)$OR_{10}$, or —$CONR_{10}R_{11}$; where $R_{10}$, $R_{11}$, and $R_{12}$ are independently hydrogen, or $C_1$-$C_6$alkyl, $C_2$-$C_6$alkenyl, $C_2$-$C_6$alkynyl, ($C_3$-$C_7$cycloalkyl)$C_0$-$C_2$alkyl, (heterocycloalkyl)$C_0$-$C_2$alkyl, (phenyl)$C_0$-$C_2$alkyl, or (5- to 6-membered monocyclic heteroaryl)$C_0$-$C_2$alkyl, each of which is substituted with 0 to 3 substituents independently chosen from halogen, hydroxyl, oxo, $C_1$-$C_2$alkyl, $C_1$-$C_2$alkoxy, trifluoromethyl, and trifluoromethoxy.

$R_{16}$ is 0 to 2 substituents independently chosen from halogen, $C_1$-$C_2$alkyl, and $C_1$-$C_2$alkoxy.

M is hydrogen or methyl.

Z is a quinoline of the formula

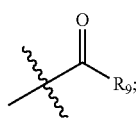

Wherein $R_{21}$ represents a substituent at the 7-position of the quinoline, and 0 to 2 additional substituents independently chosen from halogen, hydroxyl, amino, cyano,
—$CONH_2$, —COOH, $C_1$-$C_4$alkyl, $C_2$-$C_4$alkanoyl, $C_1$-$C_4$alkoxy, mono- and di-$C_1$-$C_4$alkylamino, $C_1$-$C_2$haloalkyl, and $C_1$-$C_2$haloalkoxy; and $R_{22}$ is (phenyl)$C_0$-$C_2$alkyl or (pyridyl)$C_0$-$C_2$alkyl, each of which is substituted with 0, 1, or 2 substituents independently chosen from halogen, hydroxyl, amino, cyano, —COOH, —$CONH_2$, $C_1$-$C_4$alkyl, $C_1$-$C_4$alkoxy, mono- and di-$C_1$-$C_4$alkylamino, trifluoromethyl, and trifluoromethoxy.

The invention includes compounds and salts of Formula IA

Formula IA

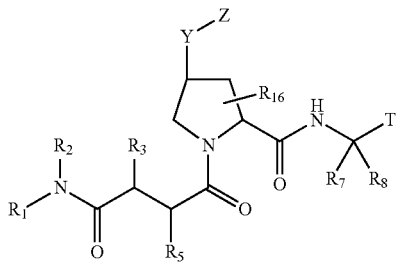

Within Formula IA, $R_1$ and $R_2$ are taken together to form a piperazinyl, morpholinyl, or piperidinyl group, each bridged with a methylene, ethylene, or oxygen bridge, or $R_1$ and $R_2$ are taken together to form a decahydroquinolinyl or decahydroisoquinolinyl group, each of which is bridged with a methylene, ethylene, or oxygen bridge; or $R_1$ and $R_2$ are taken together to form a 5- or 6-membered heterocycloalkyl group chosen from piperazinyl, morpholinyl, piperidinyl and pyrrolidinyl rings, each of which 5- or 6-membered heterocycloalkyl group is fused to a cyclohexyl group, which cyclohexyl group is bridged with a methylene, ethylene or oxygen bridge; wherein each $R_1$ and $R_2$ group is substituted with 0 to 2 substituents independently chosen from oxo, halogen, —$CONH_2$, $C_1$-$C_2$alkyl, $C_1$-$C_2$alkoxy, and $C_1$-$C_4$alkyl carbamate; $R_3$, $R_4$, and $R_6$, are independently hydrogen or methyl.

$R_5$ is $C_1$-$C_6$alkyl, ($C_3$-$C_7$cycloalkyl)$C_0$-$C_2$alkyl, or (phenyl)$C_0$-$C_2$alkyl, each of which is unsubstituted.

$R_7$ is hydrogen and $R_8$ is $C_1$-$C_4$alkyl or phenyl; or $R_7$ and $R_8$ are joined to form a vinyl-substituted cyproyl group or a 4- to 6-membered cycloalkyl ring, substituted with 0 to 2 substituents independently chosen from halogen.

Y is absent, O, S, —O(C=O)—, or —O(C=O)($NR_{20}$)—, where $R_{20}$ is hydrogen or methyl.

T is a group of the formula and $R_9$ is $NR_{10}SO_2R_{11}$, where $R_{10}$ is hydrogen or methyl; and $R_{11}$ is $C_1$-$C_6$alkyl, phenyl, $C_3$-$C_7$cycloalkyl, thienyl, or imidazolyl, each of which is substituted with 0 to 3 substituents independently chosen from halogen, $C_1$-$C_4$alkyl, $C_1$-$C_4$alkoxy, $C_2$-$C_4$alkenyl, phenyl, or benzyl.

$R_{16}$ represents 0 to 2 substituents is independently chosen at from halogen, $C_1$-$C_2$alkyl, and $C_1$-$C_2$alkoxy.

$R_{20}$ is hydrogen, $C_1$-$C_2$alkyl, $C_1$-$C_2$haloalkyl, or $C_1$-$C_2$haloalkoxy.

Z is a group of the formula

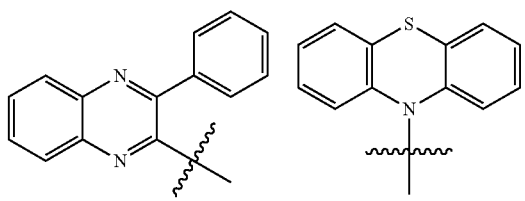

-continued
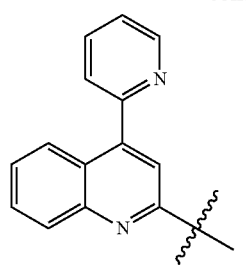
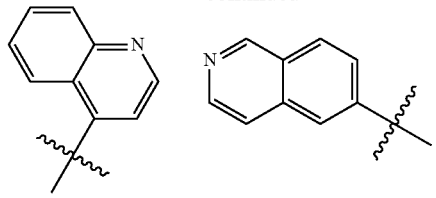
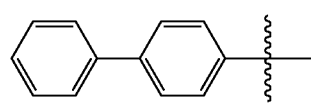
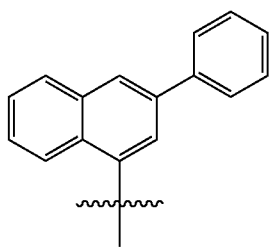
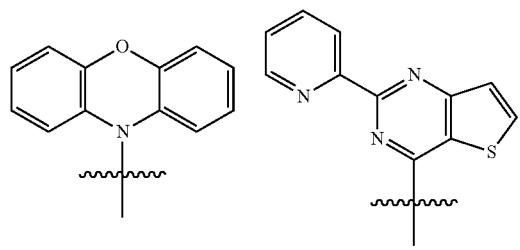
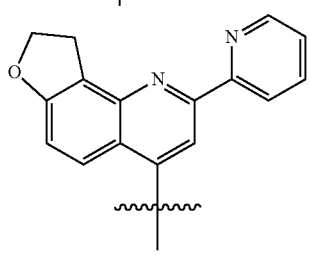
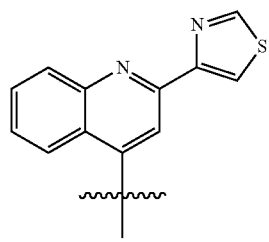
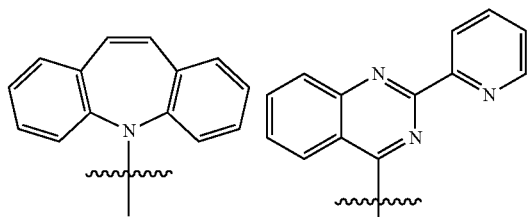
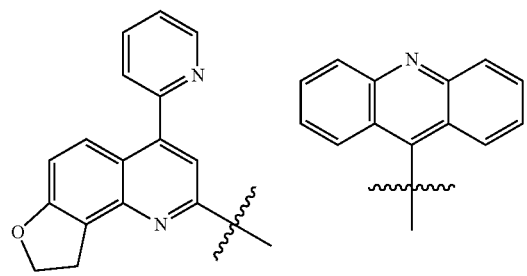
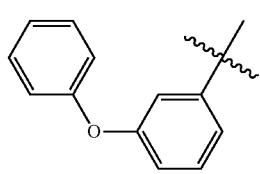
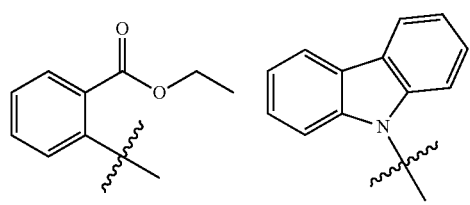
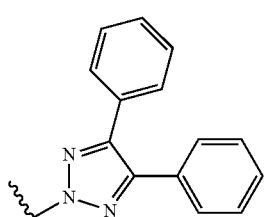
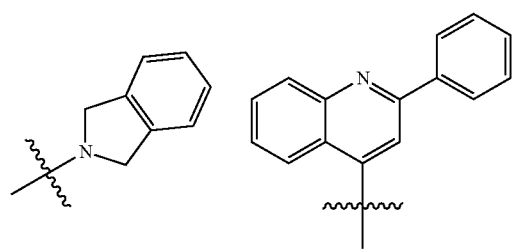
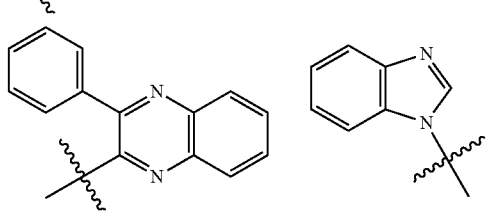

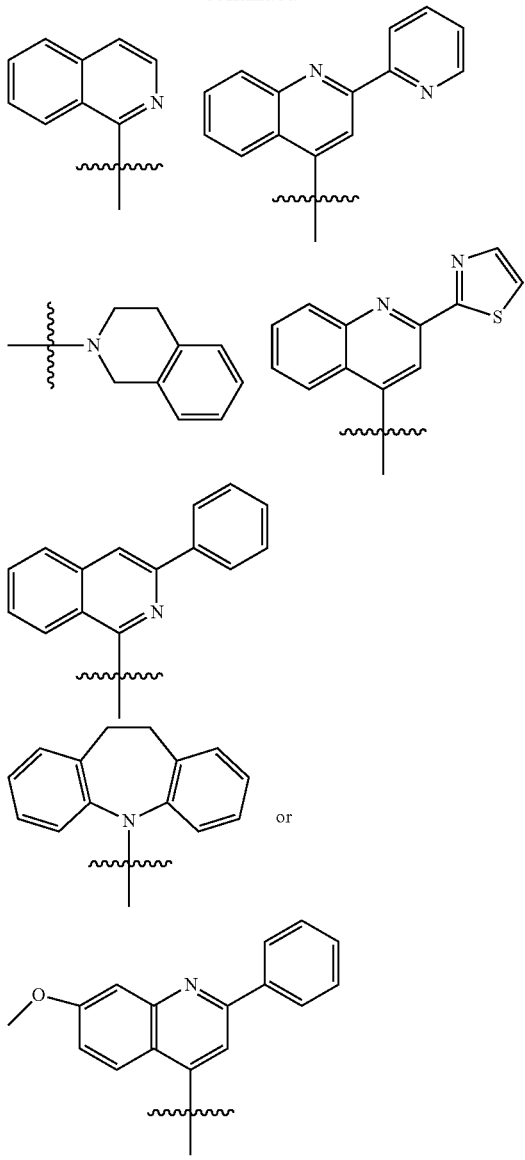

each of which is substituted by 0, 1, 2, or 3 substituents independently chosen from halogen, $C_1$-$C_4$alkyl, $C_1$-$C_4$alkoxy, and mono- and di-$C_1$-$C_4$alkylamino.

Also included herein are compounds and salts of Formula I or any of the subformulae thereof in which at least one of the following conditions is met: (1) $R_1$ and $R_2$ are joined to form a heterocycloalkyl ring which is not piperidine or pyrrolidine; (2) Y is not oxygen; and/or (3) Z is not

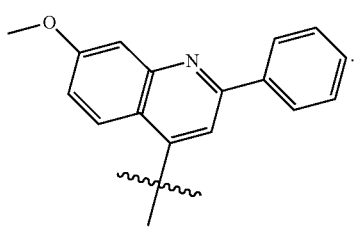 [SMILES: *c1cc(-c2ccccc2)nc2cc(OC)ccc12]

Any of the definitions for the variables $R_1$, $R_2$, $R_3$, $R_7$, $R_8$, $R_{16}$, Y, Z, and T used for Formula IA may be used for Formula I or other subgeneric formulae of Formula I so long as a stable compound results.

Pharmaceutical Preparations

Compounds of the invention can be administered as the neat chemical, but are preferably administered as a pharmaceutical composition. Accordingly, the invention provides pharmaceutical compositions comprising a compound or pharmaceutically acceptable salt of the Formula I, together with at least one pharmaceutically acceptable carrier. The pharmaceutical composition may contain a compound or salt of Formula I as the only active agent, or may contain one or more additional active agents.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions can be formulated for oral administration. These compositions contain between 0.1 and 99 weight % (wt. %) of a hydrazone or a diacyl hydrazine compound and usually at least about 5 wt. % of a hydrazone or a diacyl hydrazine compound. Some embodiments contain from about 25 wt. % to about 50 wt. % or from about 5 wt. % to about 75 wt. % of the hydrazone or diacyl hydrazine compound.

Methods of Treatment

The invention includes methods of preventing and treating hepatitis C infections, by providing an effective amount of a compound of the invention to patient at risk for hepatitis C infection or infected with a hepatitis C virus. A compound of the invention may be provided as the only active agent or may be provided together with one or more additional active agents.

The pharmaceutical combinations disclosed herein are useful for preventing and treating hepatitis C infections in patients.

An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

The invention also includes using pharmaceutical combinations comprising a compound of the invention in prophylactic therapies. In the context of prophylactic or preventative treatment an effective amount of a compound of the invention is an amount sufficient to significantly decrease the patient's risk of contracting a hepatitis C infection.

The invention includes a method of inhibiting HCV replication in vivo comprising providing a compound or salt of the invention to a patient infected with HCV a concentration of the compound or salt sufficient to inhibit HCV replicon replication in vitro. In this instance the concentration includes an in vivo concentration, such as a blood or plasma concentration. The concentration of compound sufficient to inhibit HCV replicon replication in vitro includes may be determined from an assay of replicon replication such as the assay provided in Example 3, herein.

Methods of treatment include providing certain dosage amounts of a compound of the invention to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit a compound of the invention. In certain embodiments 25 mg to 500 mg, or 25 mg to 200 mg of a compound of the invention are provided daily to a patient. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

The invention comprises providing a compound or salt of Formula I in a container together with instructions for using the composition to treat a patient suffering from Hepatitis C infection.

The invention includes packaged pharmaceutical combinations. Such packaged combinations include a compound of Formula I in a container. The container may additionally include instructions for using the combination to treat or prevent a viral infection, such as a hepatitis C infection, in a patient.

The packaged pharmaceutical combination may include one or more additional active agents.

Combination Methods

The invention includes pharmaceutical compositions and methods of treatment in which a compound or salt of the invention is provided together with one or more additional active agents. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo. In certain embodiments the second active agent is ribavirin, interferon, or Peg-interferon alpha conjugate.

According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon.

The invention methods of treatment and pharmaceutical combinations including compounds of the invention any one or combination of the following compounds and substances as an additional active agent:

Caspase inhibitors: IDN 6556 (Idun Pharmaceuticals)

Cyclophilin Inhibitors: NIM811 (Novartis) and DEBIO-025 (Debiopharm)

Cytochrome P450 monooxygenase inhibitors: ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole Glucocorticoids: hydrocortisone, cortisone, prednisone, prednisolone, methylprednisolone, triamcinolone, paramethasone, betamethasone, and dexamethasone Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), unpegylated interferon alpha, alpha interferon, and its analogs, and synthetic thymosin alpha 1 (ZADAXIN, SciClone Pharmaceuticals Inc.)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmaceuticals)

Nucleoside analogues: Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), delaviridine (RESCRIPTOR, Pfizer), and HCV-796 (Viropharm)

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101(Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

EXAMPLES

This invention is further illustrated by the following examples that should not be construed as limiting.

Compounds provided herein may generally be prepared using standard synthetic methods. Starting materials are generally readily available from commercial sources, such as Sigma-Aldrich Corp. (St. Louis, Mo.). For example, a synthetic route similar to that shown in Example 1 or 2 may be used. It will be apparent that the final product and any intermediate(s) shown in the following schemes may be extracted, dried, filtered and/or concentrated, and may be further purified (e.g., by chromatography). Each variable (e.g., "R") in the following Schemes, refers to any group consistent with the description of the compounds provided herein. An individual skilled in the art may find modifications of one or several of the synthetic steps described herein without diverting significantly from the overall synthetic scheme. Further experimental details for synthesis of representative compounds via these schemes are provided in Examples 1-5, herein.

Abbreviations

The following chemical abbreviations are used in Example 1. Additional abbreviations used in these examples will be familiar to those of skill in the art of organic chemical synthesis.

CDI 1,1'-Carbonyldiimidazole

DBU Diazabicyclo[5.4.0]undec-7-ene

DCM Dichloromethane

DIEA N,N-Diisopropylethyl amine

DMF Dimethyl formamide

HATU O-(7-azabenotriazol-1-yl)-1,1,3,3-tetramethyluronium

HBTU O-(1H-Benzotriazol-1-yl)N,N,N',N'-tetramethyluronium hexafluorophosphate

NMM N-methylmorpholine

RCM Ring-closing metathesis

TEA Triethylacetate

TFA Trifluoroacetic acid

Example 1

Synthesis of 1-((2S,4R)-1-(S)-2-tert-butyl-4-oxo-4-(piperidin-1-yl)butanoyl)-4-(7-methoxy-2-phenylquinolin-4-yloxy)pyrrolidine-2-carboxamido)-2-vinylcyclopropanecarboxylic acid Step 1. Preparation of N-(cyclopropylsulfonyl)-1-(BOC-amino)-2-vinylcyclopropanecarboxamide CDI (2.98 g, 18.4 mm, 1.1 eq) is dissolved in ethyl acetate. N-Boc-cyclopropylvinyl acid (3.8 g, 16.7 mm, 1.0 eq), prepared via the procedure given by Beaulieu, P. L. et al. (J. Org. Chem. 70: 5869-79 (2005)) is added to the CDI/ethyl acetate mixture and stirred at RT until the starting material is consumed. Cyclopropyl sulfonamine (2.2 g, 18.4 mm, 1.1 eq) is added to this mixture followed by DBU (2.1 ml, 20.5 mm, 1.23 eq) and the mixture is stirred at RT for 2 h. Workup and purification by silica gel chromatography provides 2 g of compound 2.

Step 2. Preparation of (2S,4R)-tert-butyl 2-(1-(cyclopropylsulfonylcarbamoyl)-2-vinylcyclopropylcarbamoyl)-4-(7-methoxy-2-phenylquinolin-4-yloxy)pyrrolidine-1-carboxylate and (2S,4R)—N-(1-(cyclopropylsulfonylcarbamoyl)-2-vinylcyclopropyl)-4-(7-methoxy-2-phenylquinolin-4-yloxy)pyrrolidine-2-carboxamide

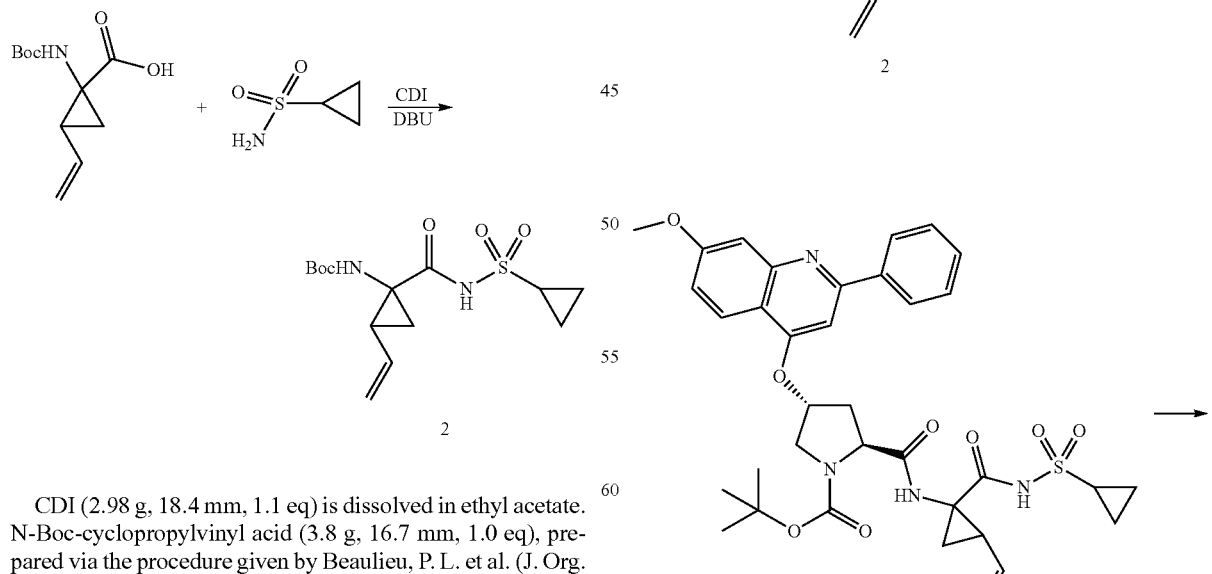

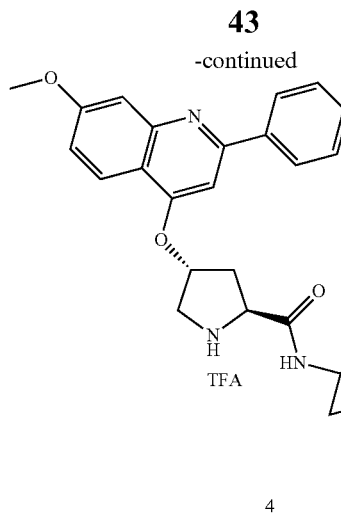

4

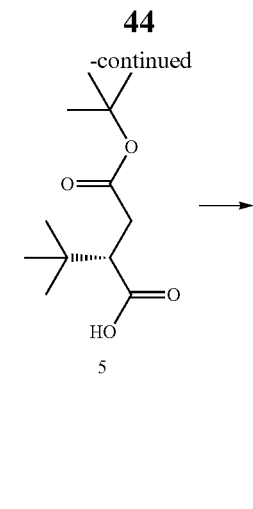

5

Compound 1 (4.3 g, 9.3 mmol, 1.1 eq), prepared according to the method given ins WO 02/060926, in DMF is stirred with O-(Benzotriazol-1yl)-N,N,N',N'-Tetramethyluronium hexafluorophosphate (4.1 g, 10.5 mmol, 1.3 eq) for 30 minutes, followed by addition of cyclopropylamine 2 (1.92 g, 8.3 mmol, 1.0 eq) and N-methylmorpholine (2.52 g, 25.0 mmol, 3.0 eq). The mixture is stirred over night and the solvent removed under reduced pressure. The resulting residue is diluted with ethyl acetate and washed with saturated aqueous NaHCO$_3$. The organic solvent is dried over MgSO$_4$ and concentrated under reduced pressure to afford crude 3, which is used for next step without further purification.

Compound 3 in 10 ml dry CH$_2$Cl$_2$ is treated with 5 mL TFA and stirred over night. The solvent is removed and the residue recrystallized from ethyl acetate to afford 4.12 g Compound 4 (61% yield two steps).

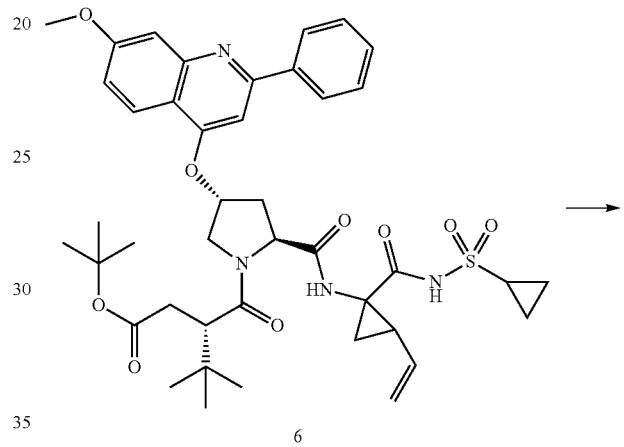

6

Step 3. Preparation of (3S)-3-((2S,4R)-2-(1-(cyclo-propylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoic acid

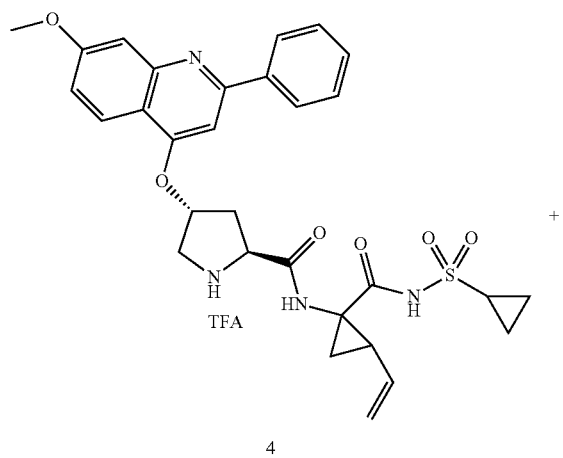

4

+

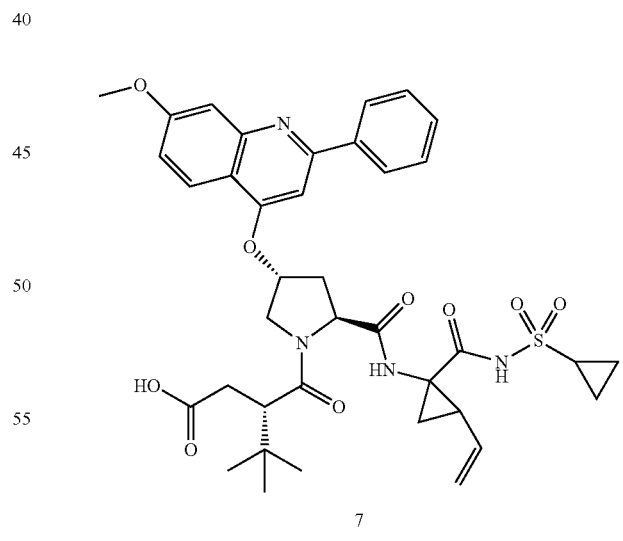

7

The Acid 5 (58 mg, 0.25 mmol, 1.2 eq), prepared via the procedure given by Evans, D. A., et al. (J. Org. Chem. 64: 6411-6417 (1999)) in 1.2 mL DMF is stirred with 4 (138 mg, 0.21 mmol), HATU (160 mg, 0.42 mmol, 2.0 eq), and DIEA (0.63 mmol, 3.0 eq) overnight. The mixture is subjected to HPLC purification to afford 121 mg 6 (77% yield), which is further treated with 0.5 mL TFA in 1.0 mL DCM overnight. The solvent was removed to provide Compound 7 in 100% yield.

Step 4. Preparation of (2S,4R)-1-(S)-2-tert-butyl-4-oxo-4-(piperidin-1-yl)butanoyl)-N-(1-(cyclopropylsulfonylcarbamoyl)-2-vinylcyclopropyl)-4-(7-methoxy-2-phenylquinolin-4-yloxy)pyrrolidine-2-carboxamide Step 5. Preparation of (3S)-3-((2S,4R)-2-(1-(ethoxycarbonyl)-2-vinylcyclopropylcarbamoyl)-4-(7-methoxy-2-phenylquinolin-4-yloxy)pyrrolidine-1-carbonyl)-4,4-dimethylpentanoic acid

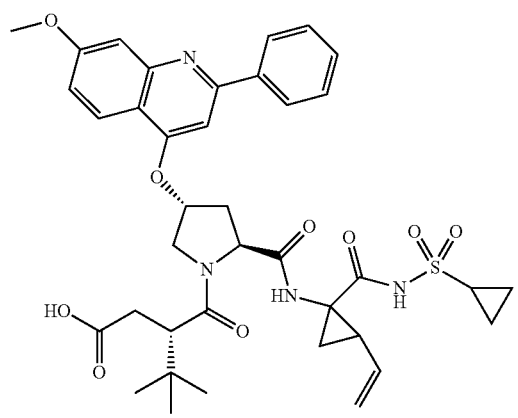

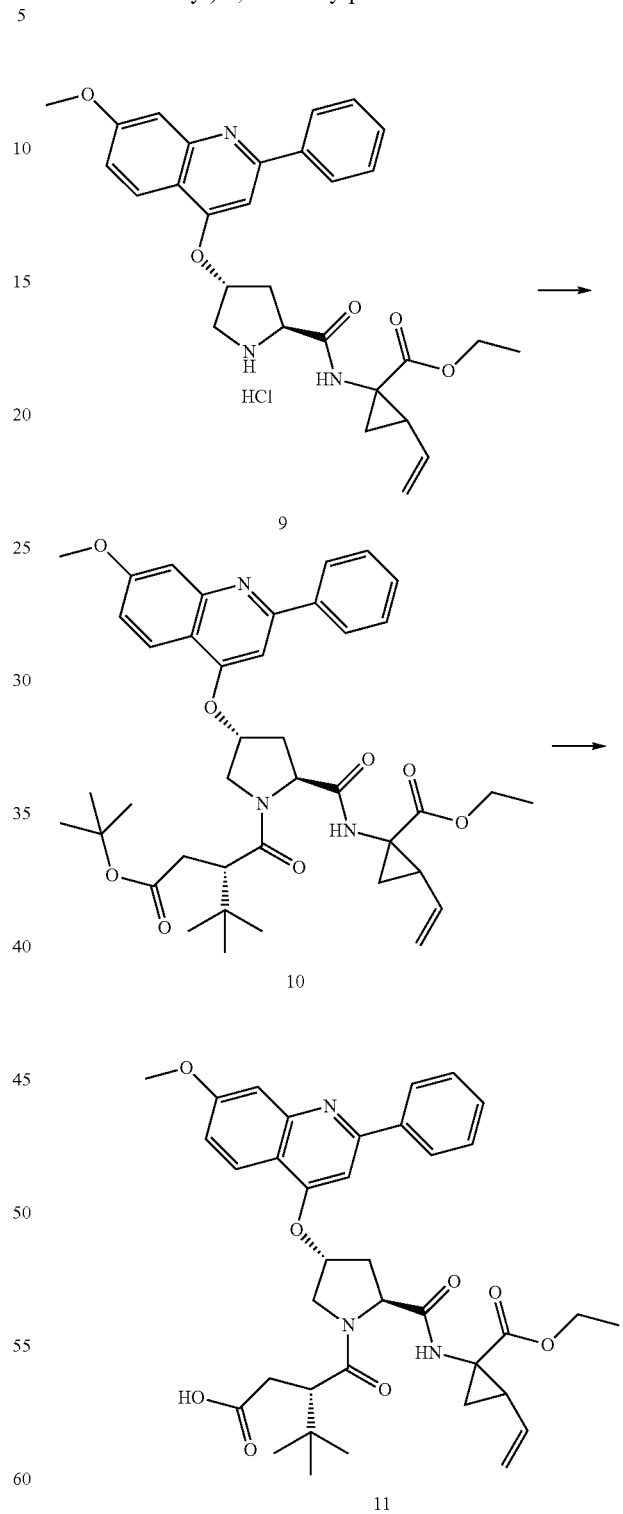

The Acid 7 (0.15 mmol) in 1.0 mL DMF is stirred with pepridine (excess, 0.6 mmol, 4 eq), HATU (115 mg, 0.3 mmol, 2.0 eq), and DIEA (0.45 mmol, 3.0 eq) for 4 hrs. The mixture is subjected to HPLC purification to afford 77.1 mg 8.

The Acid 5 (105 mg, 0.46 mmol, 1.2 eq) in 1.2 mL DMF is stirred with 9 (202 mg, 0.38 mmol), HATU (290 mg, 0.76 mmol, 2.0 eq), and DIEA (1.2 mmol, 3.0 eq) overnight. The mixture is subjected to HPLC purification to afford 204.3 mg 10 (75% yield), which is further treated with 0.5 mL TFA in 1.0 mL DCM overnight. The solvent is removed to provide 11 in 100% yield.

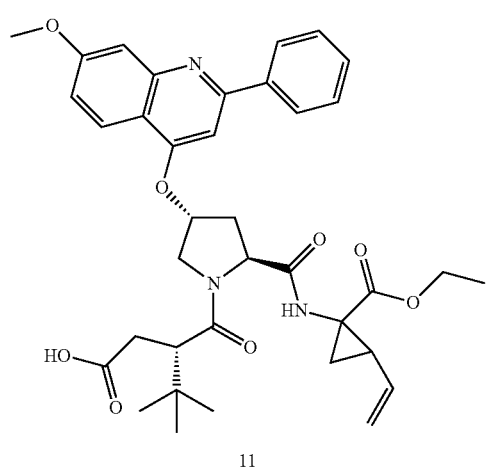

11

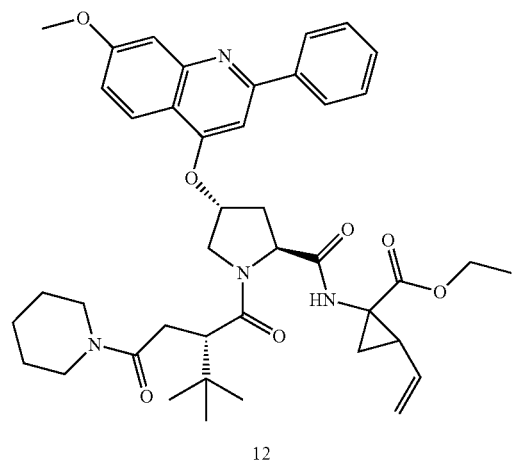

12

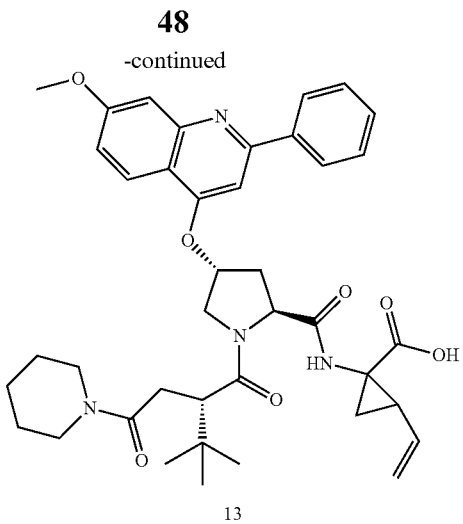

13

Step 6. Preparation of Final Product

The Acid 11 (30 mg, 0.045 mmol) in 1.0 mL DMF is stirred with pepridine (0.27 mmol, 6 eq), HATU (34 mg, 0.09 mmol, 2.0 eq), and DIEA (0.14 mmol, 3.0 eq) for 2 hrs. The mixture is subjected to HPLC purification to afford 21.2 mg 12 (65% yield), which is hydrolyzed in methanol with 2N NaOH for 6 hrs. The mixture is acidified with 6N HCl and subjected to HPLC purification to afford 7.6 mg 13.

Example 2

Additional Compounds

The compounds disclosed in Table I below are prepared by the methods set forth in Example 1 above.

TABLE I

| Cpd. | STRUCTURE | Name | EC50 | rt | MS + 1 |
|---|---|---|---|---|---|
| 38. | 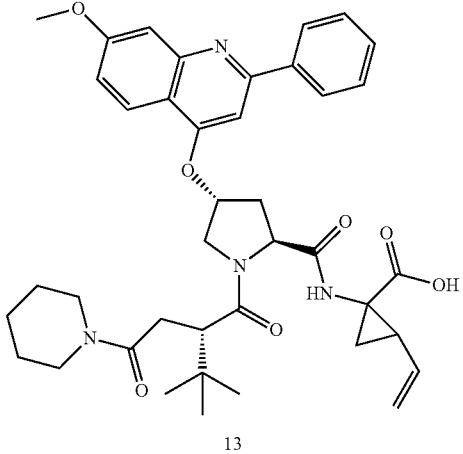 | (2S,4R)-1-((S)-2-tert-butyl-4-oxo-4-(piperidin-1-yl)butanoyl)-N-((1S,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 3.12 | 800.5 |

TABLE I-continued

| Cpd. | STRUCTURE | Name | EC50 | rt | MS + 1 |
|---|---|---|---|---|---|
| 39. | 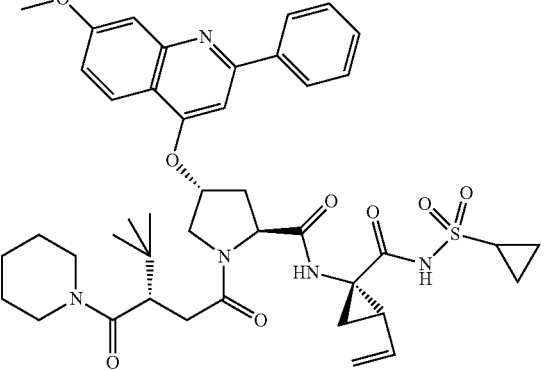 | (2S,4R)-N-(1-(cyclo-propylsulfonyl-carbamoyl)-2-vinylcyclopropyl)-1-((S)-4,4-dimethyl-3-(piperidine-1-carbonyl)pentano-yl)-4-(7-methoxy-2-phenylquinolin-4-yloxy)pyrrolidine-2-carboxamide | *** | 3.11 | 800.1 |
| 40. | 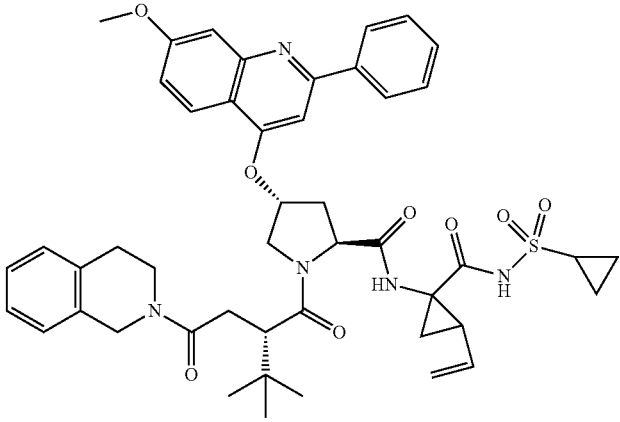 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCc2ccccc2C1)C(C)(C)C)C(=O)NS(=O)(=O)C1CC1] | (2S,4R)-1-((S)-2-tert-butyl-4-(3,4-dihydro-isoquinolin-2(1H)-yl)-4-oxobutanoyl)-N-(1-(cyclopropyl-sulfonyl-carbamoyl)-2-vinylcyclopropyl)-4-(7-methoxy-2-phenylquinolin-4-yloxy)pyrrolidine-2-carboxamide | *** | 3.27 | 848.4 |
| 41. | 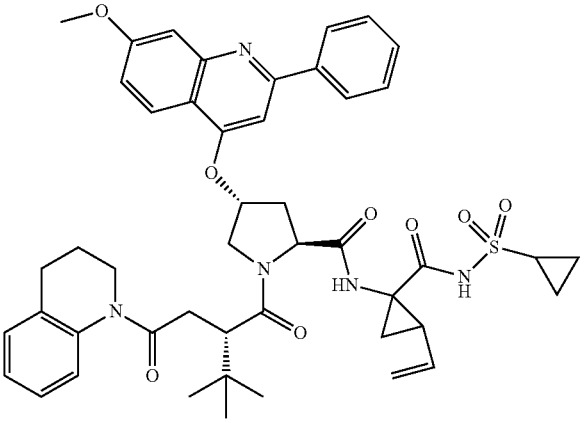 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCc2ccccc21)C(C)(C)C)C(=O)NS(=O)(=O)C1CC1] | (2S,4R)-1-((S)-2-tert-butyl-4-(3,4-dihydroquinolin-1(2H)-yl)-4-oxobutanoyl)-N-(1-(cyclopropyl-sulfonyl-carbamoyl)-2-vinylcyclopropyl)-4-(7-methoxy-2-phenylquinolin-4-yloxy)pyrrolidine-2-carboxamide | *** | 3.27 | 848.4 |

TABLE I-continued

| Cpd. | STRUCTURE | Name | EC50 | rt | MS + 1 |
|---|---|---|---|---|---|
| 42. | 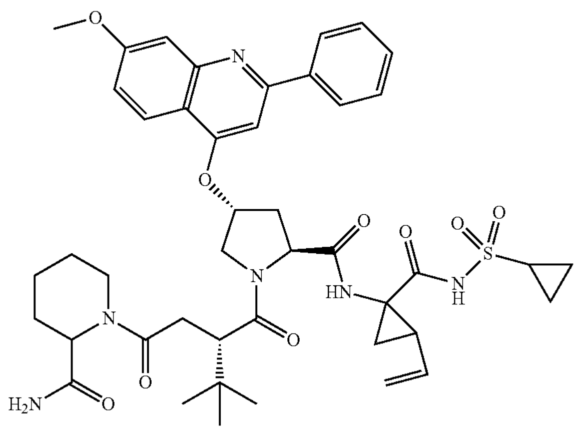 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCCC1C(N)=O)C(C)(C)C)C(=O)NS(=O)(=O)C1CC1] | 1-((3S)-3-((2S,4R)-2-(1-(cyclopropyl-sulfonyl-carbamoyl)-2-vinylcyclopropyl-carbamoyl)-4-(7-methoxy-2-phenylquinolin-4-yloxy)pyrrolidine-1-carbonyl)-4,4-dimethylpentano-yl)piperidine-2-carboxamide | *** | 2.75 | 843.4 |
| 43. | 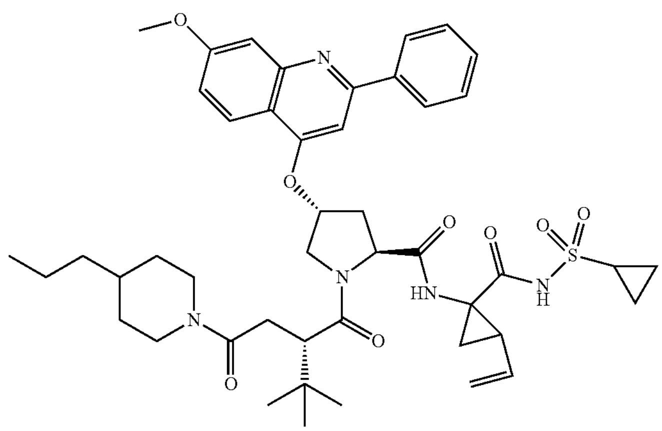 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCC(CCC)CC1)C(C)(C)C)C(=O)NS(=O)(=O)C1CC1] | (2S,4R)-1-((S)-2-tert-butyl-4-oxo-4-(4-propylpiperidin-1-yl)butanoyl)-N-(1-(cyclopropyl-sulfonyl-carbamoyl)-2-vinylcyclopropyl)-4-(7-methoxy-2-phenylquinolin-4-yloxy)pyrrolidine-2-carboxamide | ** | 3.52 | 842.5 |
| 44. | 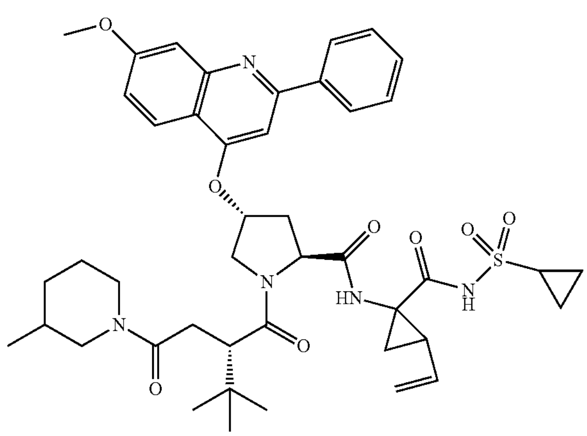 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCC(C)C1)C(C)(C)C)C(=O)NS(=O)(=O)C1CC1] | (2S,4R)-1-((2S)-2-tert-butyl-4-(3-methylpiperidin-1-yl)-4-oxobutanoyl)-N-(1-(cyclopropyl-sulfonyl-carbamoyl)-2-vinylcyclopropyl)-4-(7-methoxy-2-phenylquinolin-4-yloxy)pyrrolidine-2-carboxamide | ** | 3.15 | 814.5 |

TABLE I-continued

| Cpd. | STRUCTURE | Name | EC50 | rt | MS + 1 |
|---|---|---|---|---|---|
| 45. | 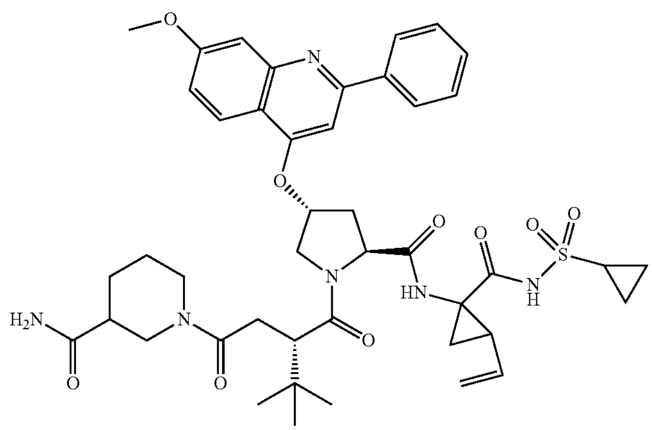 [SMILES: C=CC1CC1(NC(=O)[C@@H]1C[C@@H](Oc2cc(-c3ccccc3)nc3cc(OC)ccc23)CN1C(=O)[C@@H](CC(=O)N1CCCC(C(N)=O)C1)C(C)(C)C)C(=O)NS(=O)(=O)C1CC1] | 1-((3S)-3-((2S,4R)-2-(1-(cyclopropyl-sulfonylcarbamoyl)-2-vinylcyclopropyl-carbamoyl)-4-(7-methoxy-2-phenylquinolin-4-yloxy)pyrrolidine-1-carbonyl)-4,4-dimethylpentano-yl)piperidine-3-carboxamide | ** | 2.59 | 843.4 |
| 46. | 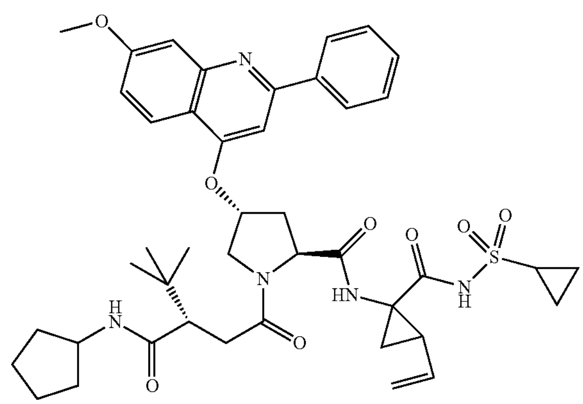 [SMILES: C=CC1CC1(NC(=O)[C@@H]1C[C@@H](Oc2cc(-c3ccccc3)nc3cc(OC)ccc23)CN1C(=O)C[C@H](C(=O)NC1CCCC1)C(C)(C)C)C(=O)NS(=O)(=O)C1CC1] | (2S,4R)-1-((S)-3-(cyclopentyl-carbamoyl)-4,4-(dimethyl-pentanoyl)-N-(1-(cyclopropylsulfonyl-carbamoyl)-2-vinylcyclopropyl)-4-(7-methoxy-2-phenylquinolin-4-yloxy)pyrrolidine-2-carboxamide | *** | 3.09 | 800.4 |
| 47. | 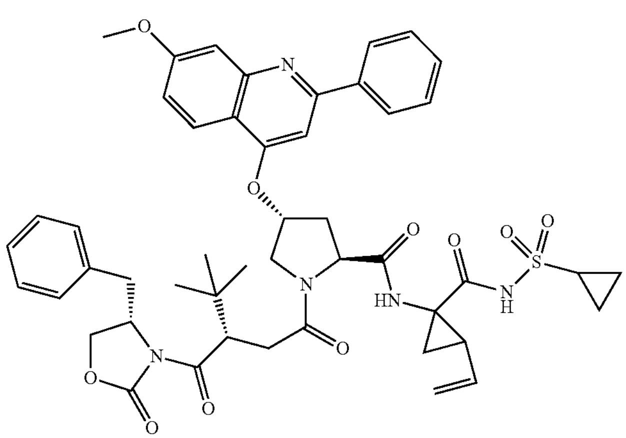 [SMILES: C=CC1CC1(NC(=O)[C@@H]1C[C@@H](Oc2cc(-c3ccccc3)nc3cc(OC)ccc23)CN1C(=O)C[C@H](C(=O)N1C(=O)OC[C@@H]1Cc1ccccc1)C(C)(C)C)C(=O)NS(=O)(=O)C1CC1] | (2S,4R)-1-((S)-3-((S)-4-benzyl-2-oxooxazolidine-3-carbonyl)-4,4-dimethyl-pentanoyl)-N-(1-(cyclopropyl-sulfonylcarbamoyl)-2-vinylcyclopropyl)-4-(7-methoxy-2-phenylquinolin-4-yloxy)pyrrolidine-2-carboxamide | ** | 3.31 | 891.6 |

| Cpd. | STRUCTURE | Name | EC50 | rt | MS + 1 |
|---|---|---|---|---|---|
| 48. | 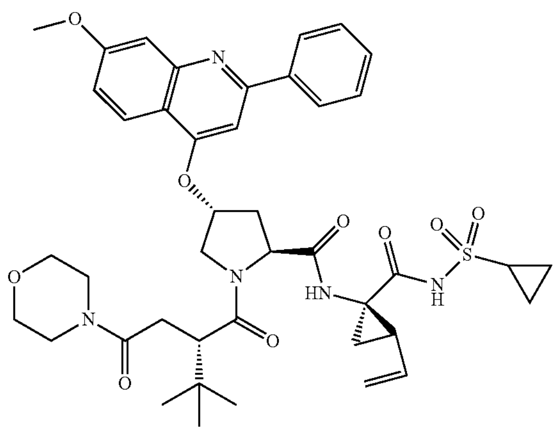 | (2S,4R)-1-((S)-2-tert-butyl-4-morpholino-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 3.03 | 802.5 |
| 49. | 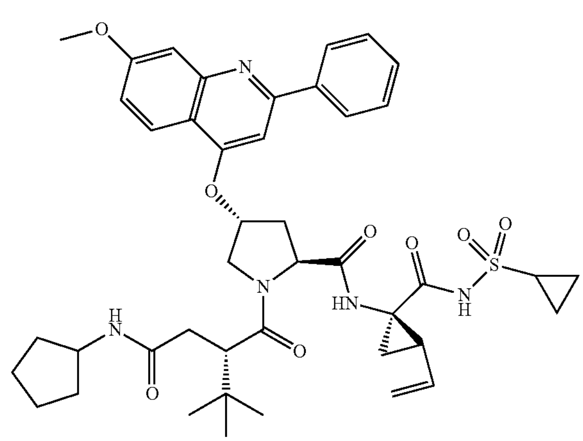 | (2S,4R)-1-((S)-2-tert-butyl-4-(cyclopentylamino)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 3.12 | 801.2 |

TABLE I-continued

| Cpd. | STRUCTURE | Name | EC50 | rt | MS + 1 |
|---|---|---|---|---|---|
| 50. | 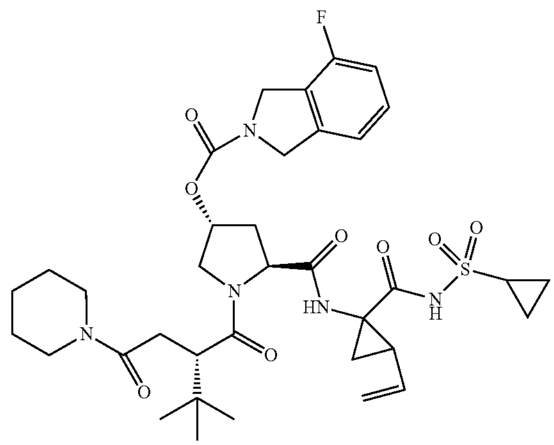 [SMILES: C=CC1CC1(NC(=O)[C@@H]1C[C@@H](OC(=O)N2Cc3cccc(F)c3C2)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-(1-(cyclopropyl-sulfonylcarbamoyl)-2-vinylcyclopropyl-carbamoyl)pyr-rolidin-3-yl 4-fluoroisoindoline-2-carboxylate | *** | 2.47 | 730.3 |
| 51. | 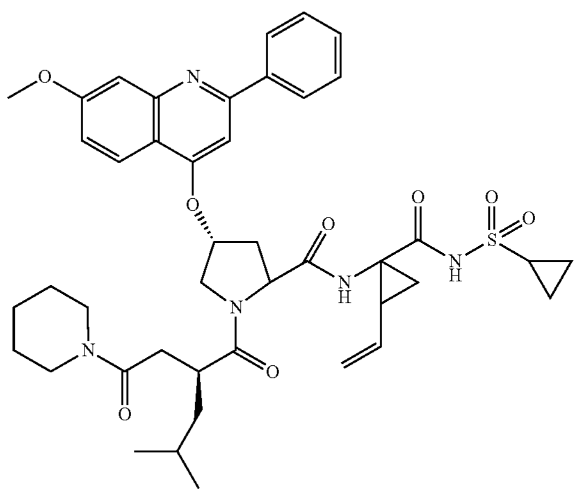 [SMILES: C=CC1CC1(NC(=O)C1C[C@@H](Oc2cc(-c3ccccc3)nc3cc(OC)ccc23)CN1C(=O)[C@H](CC(=O)N1CCCCC1)CC(C)C)C(=O)NS(=O)(=O)C1CC1] | (4R)-N-(1-(cyclopropyl-sulfonylcarbamoyl)-2-vinylcyclopropyl)-4-(7-methoxy-2-phenylquinolin-4-yloxy)-1-((S)-4-methyl-2-(2-oxo-2-(piperidin-1-yl)ethyl)pentano-yl)pyrrolidine-2-carboxamide | ** | 3.06 | 800 |
| 52. | 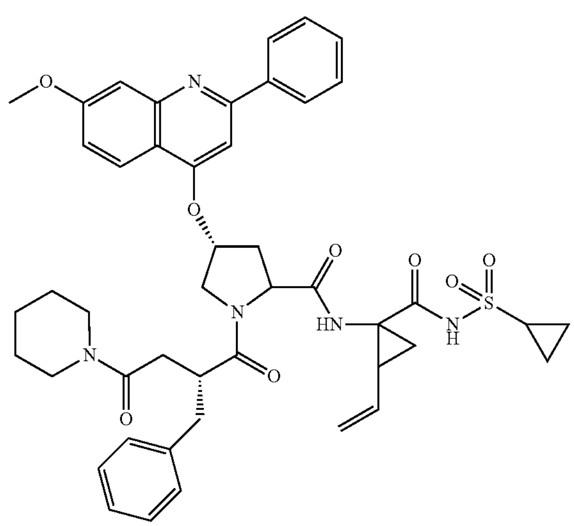 [SMILES: C=CC1CC1(NC(=O)C1C[C@@H](Oc2cc(-c3ccccc3)nc3cc(OC)ccc23)CN1C(=O)[C@@H](CC(=O)N1CCCCC1)Cc1ccccc1)C(=O)NS(=O)(=O)C1CC1] | (4R)-1-((R)-2-benzyl-4-oxo-4-(piperidin-1-yl)butanoyl)-N-(1-(cyclopropyl-sulfonylcarbamoyl)-2-vinylcyclopropyl)-4-(7-methoxy-2-phenylquinolin-4-yloxy)pyrrolidine-2-carboxamide | *** | 3.14 | 834 |

TABLE I-continued

| Cpd. | STRUCTURE | Name | EC50 | rt | MS + 1 |
|---|---|---|---|---|---|
| 53. | 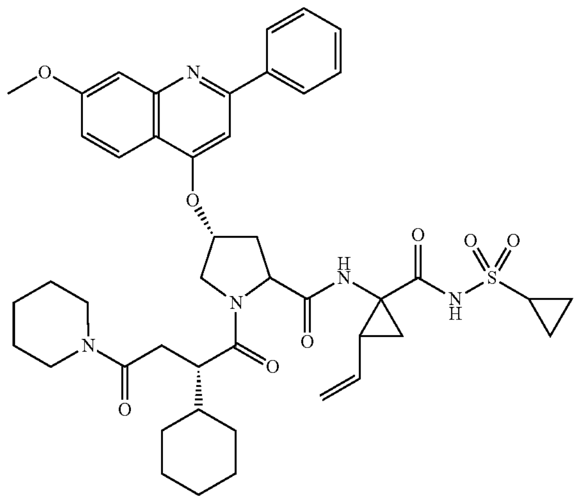 [SMILES: C=CC1CC1(NC(=O)C1C[C@@H](Oc2cc(-c3ccccc3)nc3cc(OC)ccc23)CN1C(=O)[C@@H](CC(=O)N1CCCCC1)C1CCCCC1)C(=O)NS(=O)(=O)C1CC1] | (4R)-1-((S)-2-cyclohexyl-4-oxo-4-(piperidin-1-yl)butanoyl)-N-(1-(cyclopropyl-sulfonylcarbamoyl)-2-vinylcyclopropyl)-4-(7-methoxy-2-phenylquinolin-4-yloxy)pyrrolidine-2-carboxamide | *** | 3.3 | 826 |
| 54. | 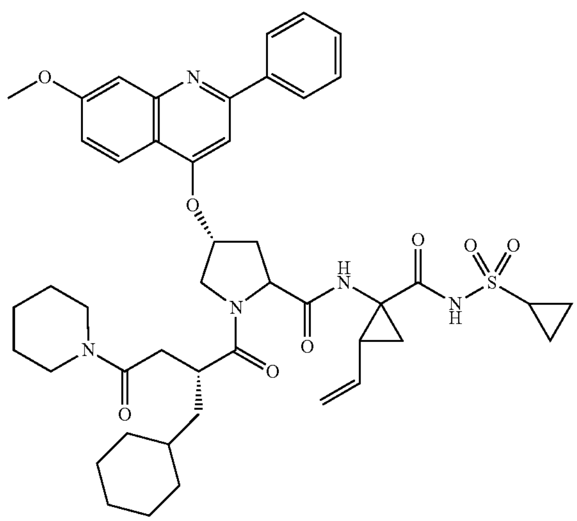 [SMILES: C=CC1CC1(NC(=O)C1C[C@@H](Oc2cc(-c3ccccc3)nc3cc(OC)ccc23)CN1C(=O)[C@@H](CC(=O)N1CCCCC1)CC1CCCCC1)C(=O)NS(=O)(=O)C1CC1] | (4R)-1-((R)-2-(cyclohexylmethyl)-4-oxo-4-(piperidin-1-yl)butanoyl)-N-(1-(cyclopropyl-sulfonylcarbamoyl)-2-vinylcyclopropyl)-4-(7-methoxy-2-phenylquinolin-4-yloxy)pyrrolidine-2-carboxamide | *** | 3.36 | 840 |
| 55. | 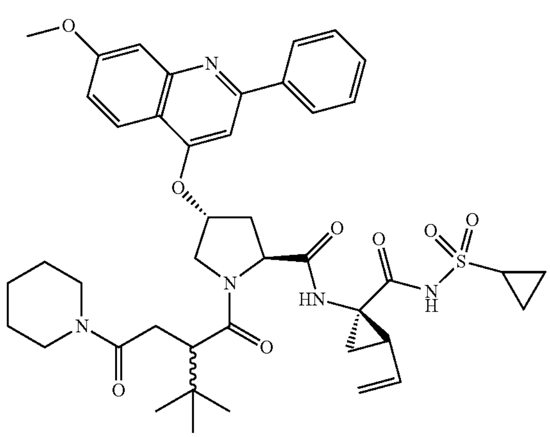 | (2S,4R)-1-(2-tert-butyl-4-oxo-4-(piperidin-1-yl)butanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 3.18 | 800.4 |

TABLE I-continued

| Cpd. | STRUCTURE | Name | EC50 | rt | MS + 1 |
|---|---|---|---|---|---|
| 56. | 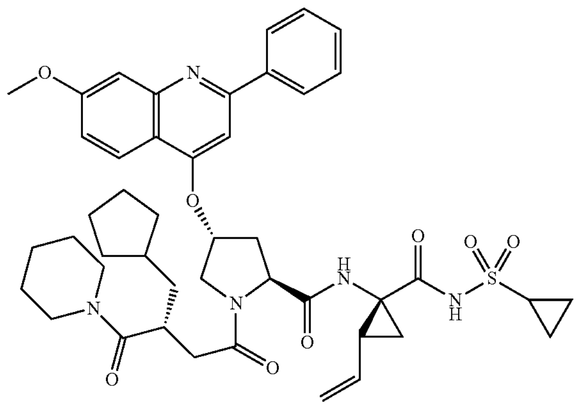 | (2S,4R)-1-((R)-3-(cyclopentyl-methyl)-4-oxo-4-(piperidin-1-yl)butanoyl)-N-((1R,2R)-1-(cyclopropyl-sulfonylcarbamoyl)-2-vinylcyclopropyl)-4-(7-methoxy-2-phenylquinolin-4-yloxy)pyrrolidine-2-carboxamide | ** | 3.19 | 826 |
| 57. | 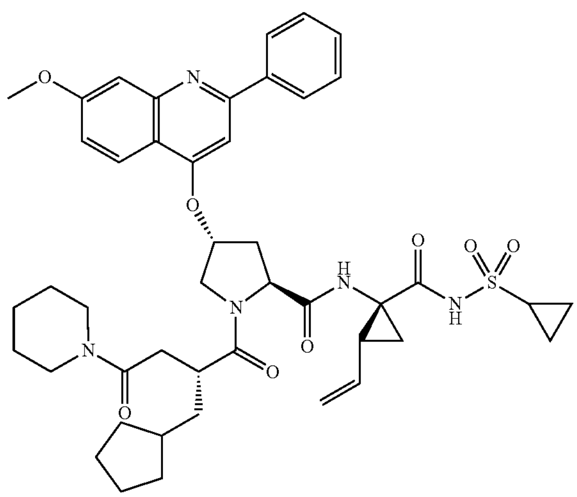 | (2S,4R)-1-((R)-2-(cyclopentylmethyl)-4-oxo-4-(piperidin-1-yl)butanoyl)-N-((1R,2R)-1-(cyclopropyl-sulfonylcarbamoyl)-2-vinylcyclopropyl)-4-(7-methoxy-2-phenylquinolin-4-yloxy)pyrrolidine-2-carboxamide | *** | 3.3 | 826 |
| 58. | 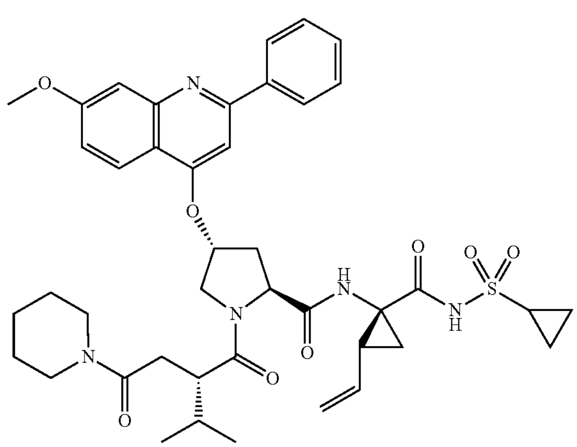 | (2S,4R)-N-((1R,2R)-1-(cyclopropyl-sulfonylcarbamoyl)-2-vinylcyclopropyl)-1-((S)-2-isopropyl-4-oxo-4-(piperidin-1-yl)butanoyl)-4-(7-methoxy-2-phenylquinolin-4-yloxy)pyrrolidine-2-carboxamide | *** | 3.01 | 786 |

TABLE I-continued

| Cpd. | STRUCTURE | Name | EC50 | rt | MS + 1 |
|---|---|---|---|---|---|
| 59. | 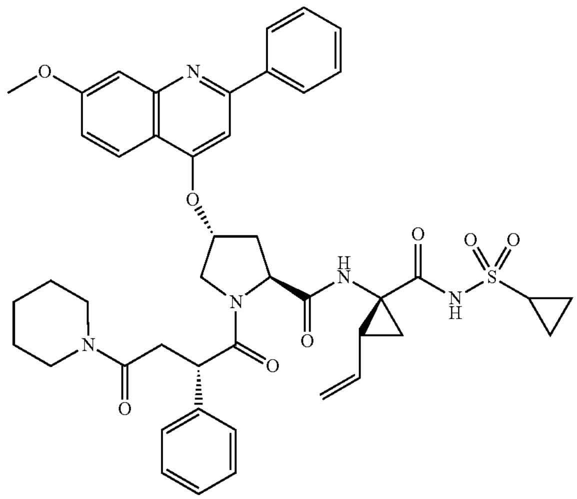 | (2S,4R)-N-((1R,2R)-1-(cyclopropyl-sulfonylcarbamoyl)-2-vinylcyclopropyl)-4-(7-methoxy-2-phenylquinolin-4-yloxy)-1-((S)-4-oxo-2-phenyl-4-(piperidin-1-yl)butanoyl)pyr-rolidine-2-carboxamide | *** | 3.13 | 820 |
| 60. | 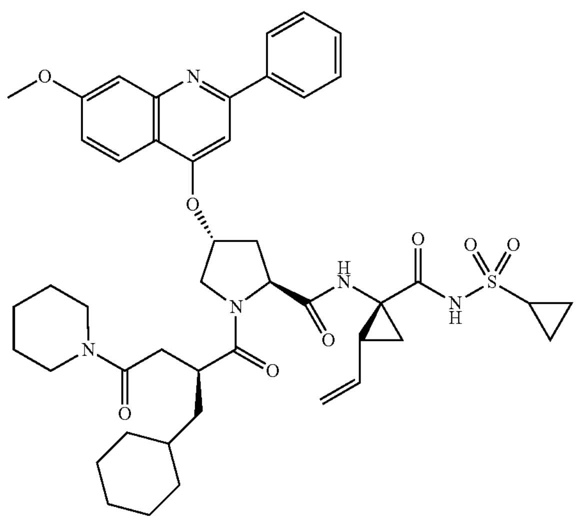 | (2S,4R)-1-((S)-2-(cyclohexylmethyl)-4-oxo-4-(piperidin-1-yl)butanoyl)-N-((1R,2R)-1-(cyclopropyl-sulfonylcarbamoyl)-2-vinylcyclopropyl)-4-(7-methoxy-2-phenylquinolin-4-yloxy)pyrrolidine-2-carboxamide | ** | 3.45 | 840 |
| 61. | 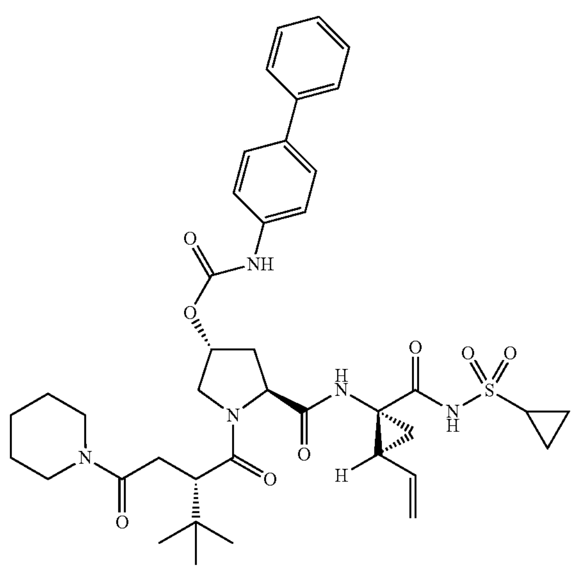 [SMILES: C=C[C@@H]1C[C@]1(NC(=O)[C@@H]1C[C@@H](OC(=O)Nc2ccc(-c3ccccc3)cc2)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropyl-sulfonylcarbamoyl)-2-vinylcyclopropyl-carbamoyl)pyrrolidin-3-yl biphenyl-4-ylcarbamate | ** | 4.34 | 763 |

TABLE I-continued

| Cpd. | STRUCTURE | Name | EC50 | rt | MS + 1 |
|---|---|---|---|---|---|
| 62. | 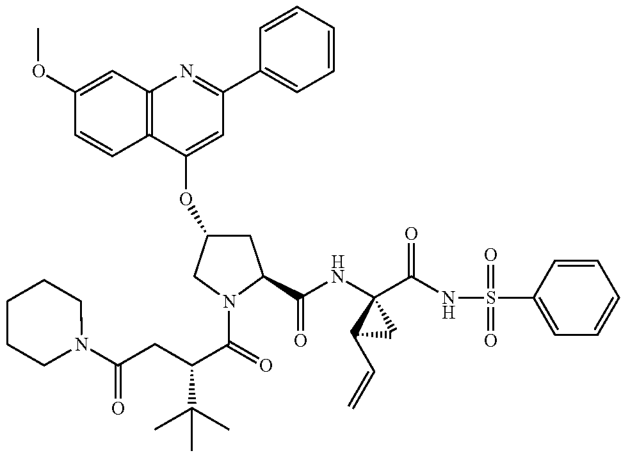 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)c1ccccc1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(phenylsulfonylcarbamoyl)-2-vinylcyclopropyl)pyrrolidine-2-carboxamide | *** | 1.75 | 836 |
| 63. | 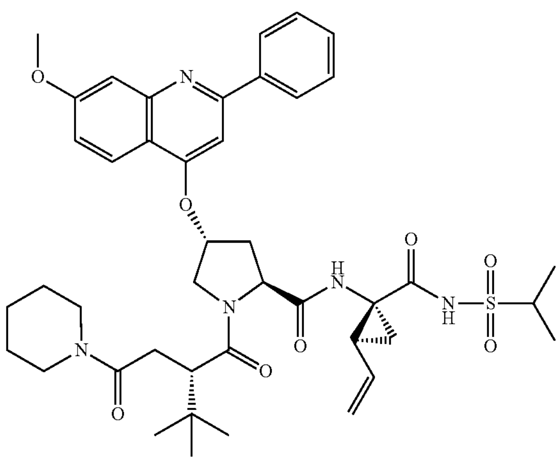 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C(C)C] | (2S,4R)-1-((S)-2-tert-butyl-4-oxo-4-(piperidin-1-yl)butanoyl)-N-((1R,2S)-1-(isopropylsulfonylcarbamoyl)-2-vinylcyclopropyl)-4-(7-methoxy-2-phenylquinolin-4-yloxy)pyrrolidine-2-carboxamide | *** | 1.63 | 802 |
| 64. | 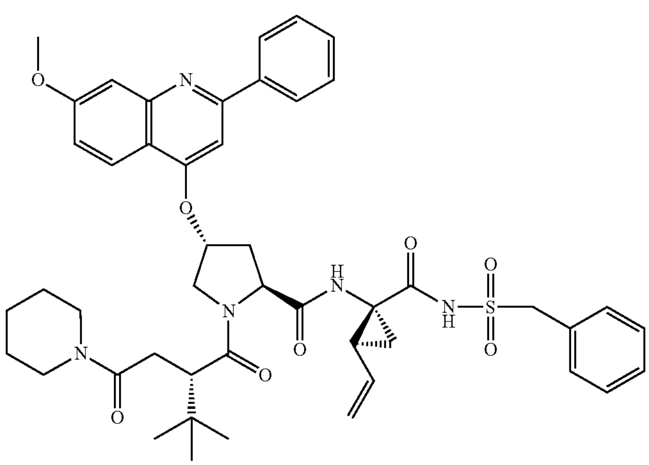 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)Cc1ccccc1] | (2S,4R)-N-((1R,2S)-1-(benzylsulfonylcarbamoyl)-2-vinylcyclopropyl)-1-((S)-2-tert-butyl-4-oxo-4-(piperidin-1-yl)butanoyl)-4-(7-methoxy-2-phenylquinolin-4-yloxy)pyrrolidine-2-carboxamide | ** | 1.79 | 850 |

| Cpd. | STRUCTURE | Name | EC50 | rt | MS + 1 |
|---|---|---|---|---|---|
| 65. | 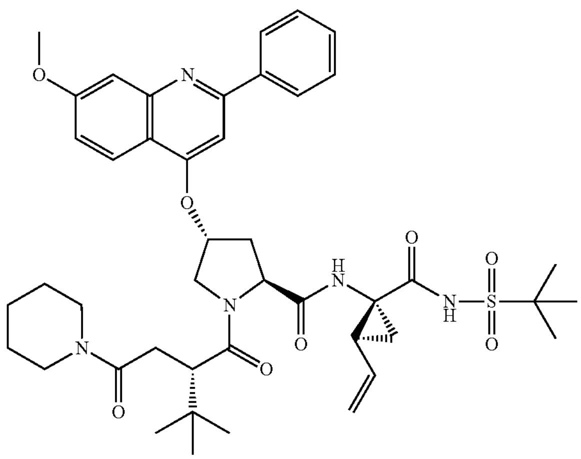 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C(C)(C)C] | (2S,4R)-1-((S)-2-tert-butyl-4-oxo-4-(piperidin-1-yl)butanoyl)-N-((1R,2S)-1-(tert-butylsulfonyl-carbamoyl)-2-vinylcyclopropyl)-4-(7-methoxy-2-phenylquinolin-4-yloxy)pyrrolidine-2-carboxamide | ** | 1.74 | 816 |
| 66. | 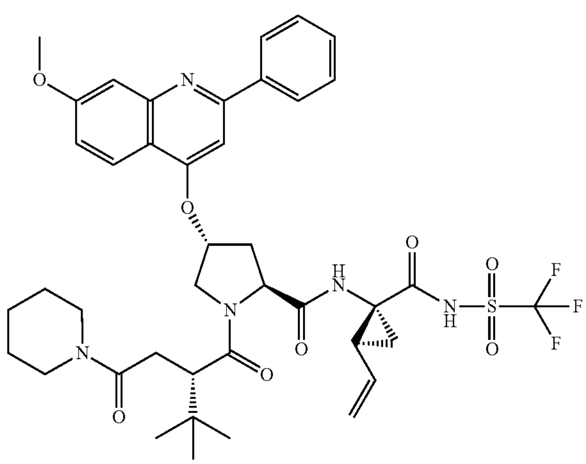 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C(F)(F)F] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(trifluoromethyl-sulfonylcarbamoyl)-2-vinylcyclo-propyl)pyrrolidine-2-carboxamide | ** | 1.81 | 828 |
| 67. | 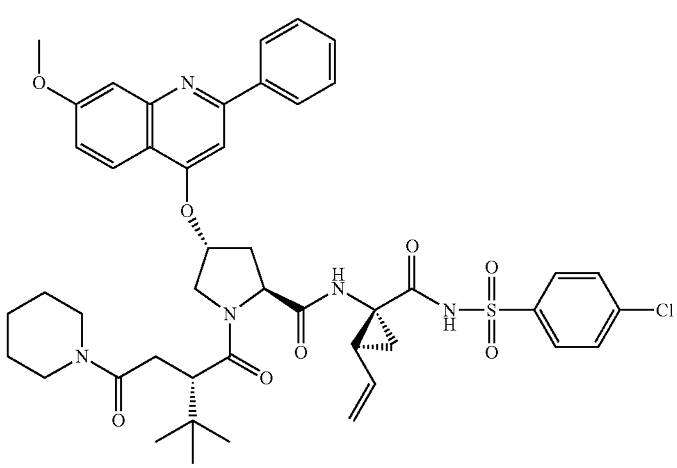 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)c1ccc(Cl)cc1] | (2S,4R)-1-((S)-2-tert-butyl-4-oxo-4-(piperidin-1-yl)butanoyl)-N-((1R,2S)-1-(4-chlorophenyl-sulfonylcarbamoyl)-2-vinylcyclopropyl)-4-(7-methoxy-2-phenylquinolin-4-yloxy)pyrrolidine-2-carboxamide | *** | 1.94 | 870 |

| Cpd. | STRUCTURE | Name | EC50 | rt | MS + 1 |
|---|---|---|---|---|---|
| 68. | 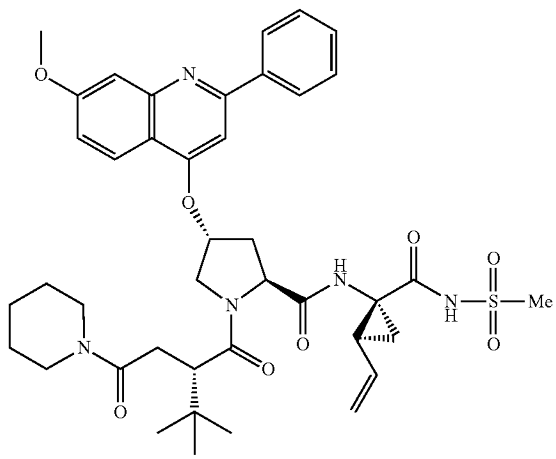 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(C)(=O)=O] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(methylsulfonyl-carbamoyl)-2-vinyl-cyclopropyl)pyrrolidine-2-carboxamide | *** | 1.64 | 774 |
| 69. | 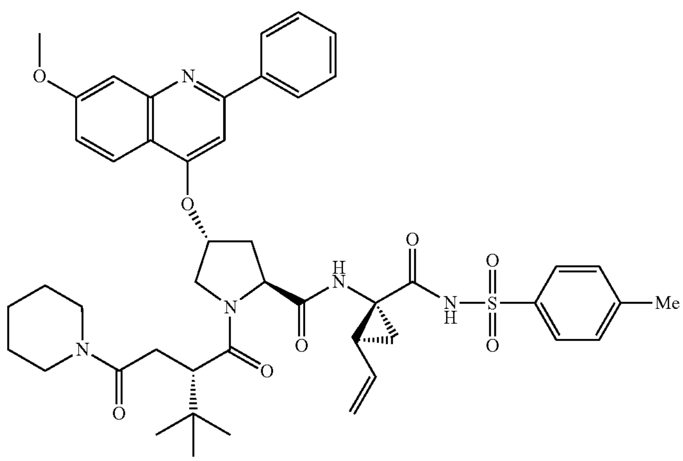 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)c1ccc(C)cc1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(p-tolylsulfonyl-carbamoyl)-2-vinyl-cyclopropyl)pyrrolidine-2-carboxamide | *** | 1.95 | 850 |
| 70. | 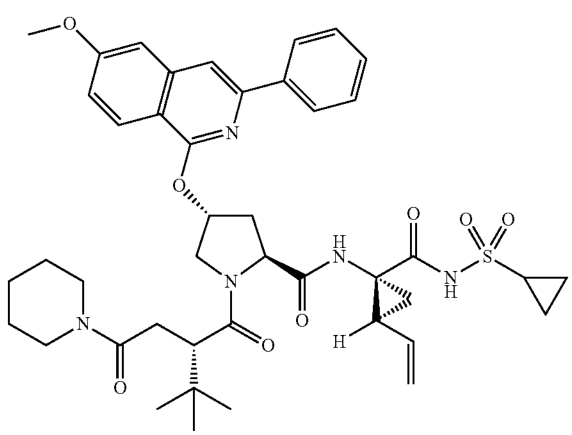 [SMILES: C=C[C@@H]1C[C@]1(NC(=O)[C@@H]1C[C@@H](Oc2nc(-c3ccccc3)cc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(6-methoxy-3-phenylisoquinolin-1-yloxy)pyrrolidine-2-carboxamide | *** | 2.69 | 800.5 |

TABLE I-continued

| Cpd. | STRUCTURE | Name | EC50 | rt | MS + 1 |
|---|---|---|---|---|---|
| 71. | 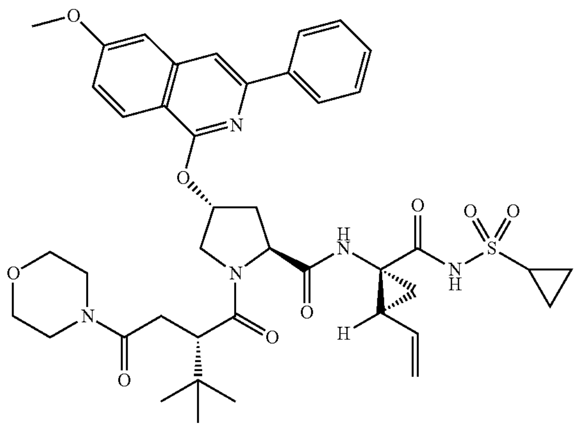 [SMILES: C=C[C@@H]1C[C@]1(NC(=O)[C@@H]1C[C@@H](Oc2nc(-c3ccccc3)cc3cc(OC)ccc23)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-N-((1R,2S)-1-(cyclopropylsulfonyl-carbamoyl)-2-vinylcyclopropyl)-4-(6-methoxy-3-phenylisoquinolin-1-yloxy)pyrrolidine-2-carboxamide | *** | 2.5 | 802.5 |
| 72. | 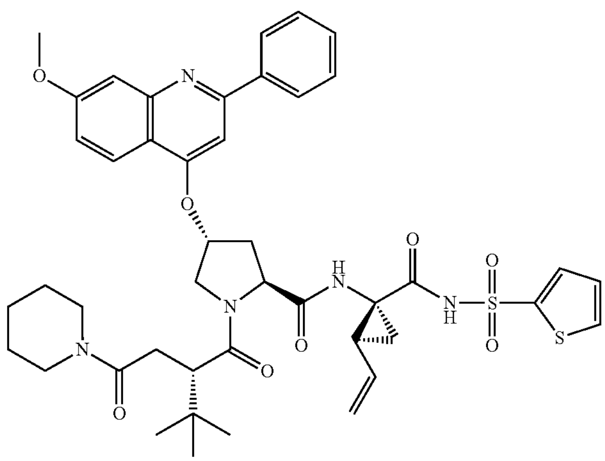 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)c1cccs1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(thiophen-2-ylsulfonylcarbamoyl)-2-vinylcyclopropyl)pyrrolidine-2-carboxamide | *** | 1.83 | 842 |
| 73. | 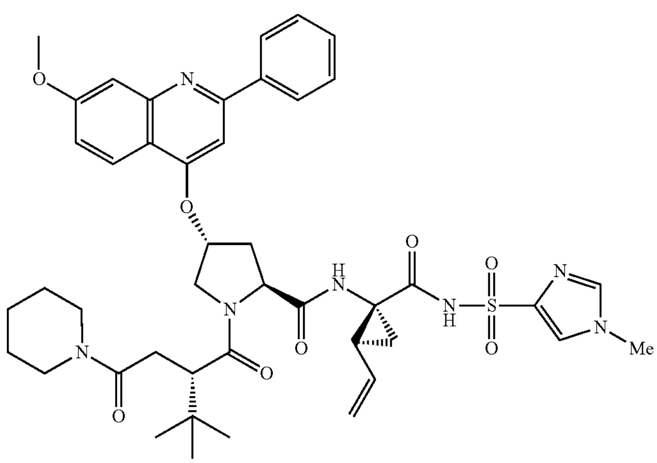 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)c1cn(C)cn1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(1-methyl-1H-imidazol-4-ylsulfonylcarbamoyl)-2-vinylcyclopropyl)pyrrolidine-2-carboxamide | ** | 1.65 | 840 |

TABLE I-continued

| Cpd. | STRUCTURE | Name | EC50 | rt | MS + 1 |
|---|---|---|---|---|---|
| 74. | 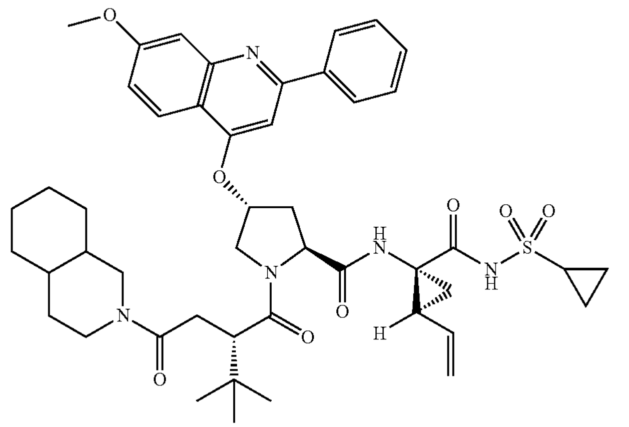 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC2CCCCC2C1)C(C)(C)C)C(=O)NS(=O)(=O)C1CC1] | (2S,4R)-1-((2S)-2-tert-butyl-4-(octahydroisoquinolin-2(1H)-yl)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 2.13 | 855 |
| 75. | 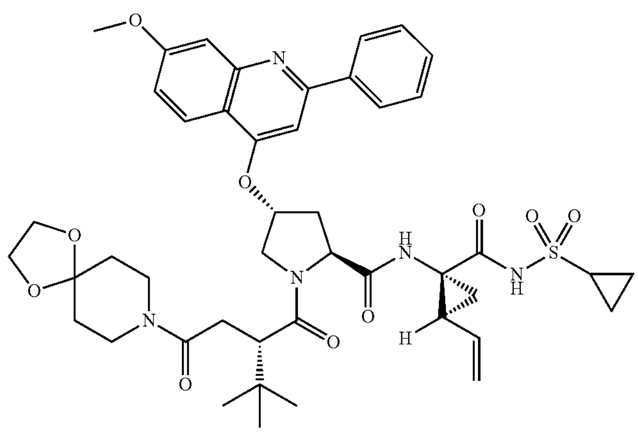 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC2(CC1)OCCO2)C(C)(C)C)C(=O)NS(=O)(=O)C1CC1] | (2S,4R)-1-((2S)-2-tert-butyl-4-oxo-4-(1,4-dioxa-8-azaspiro[4.5]decan-8-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.95 | 859 |
| 76. | 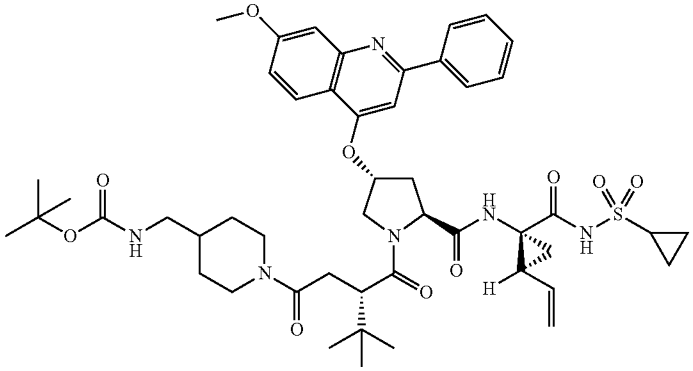 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(CNC(=O)OC(C)(C)C)CC1)C(C)(C)C)C(=O)NS(=O)(=O)C1CC1] | tert-butyl (1-((S)-3-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoyl)piperidin-4-yl)methylcarbamate | *** | 2.09 | 930 |

TABLE I-continued

| Cpd. | STRUCTURE | Name | EC50 | rt | MS + 1 |
|---|---|---|---|---|---|
| 77. | 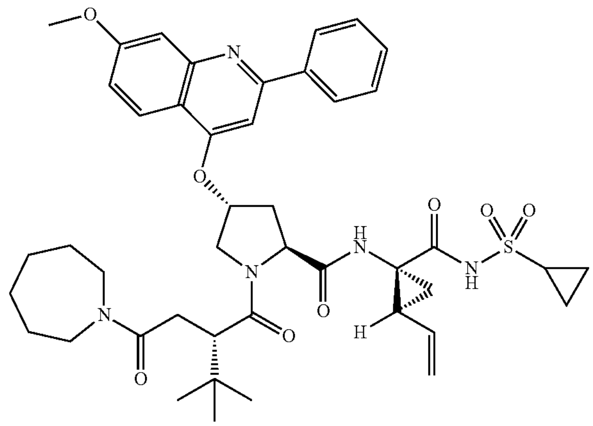 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCCC1)C(C)(C)C)C(=O)NS(=O)(=O)C1CC1] | (2S,4R)-1-((S)-4-(azepan-1-yl)-2-tert-butyl-4-oxobutanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 2.11 | 815 |
| 78. | 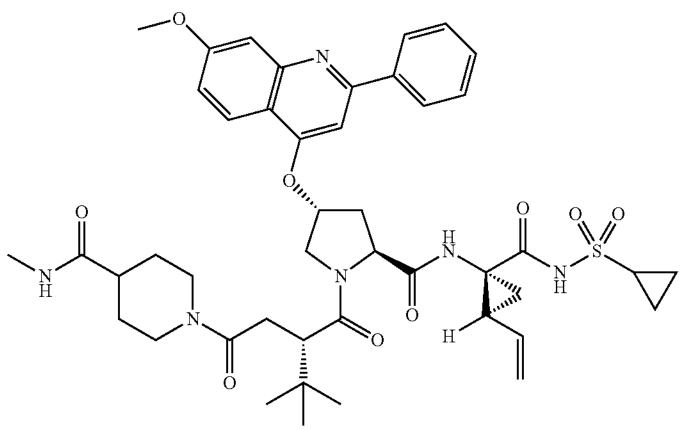 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(C(=O)NC)CC1)C(C)(C)C)C(=O)NS(=O)(=O)C1CC1] | 1-((S)-3-((2S,4R)-2-((1R,2S)-1-(cyclopropyl-sulfonylcarbamoyl)-2-vinylcyclopropyl-carbamoyl)-4-(7-methoxy-2-phenylquinolin-4-yloxy)pyrrolidine-1-carbonyl)-4,4-dimethylpentanoyl)-N-methylpiperidine-4-carboxamide | *** | 1.94 | 858 |
| 79. | 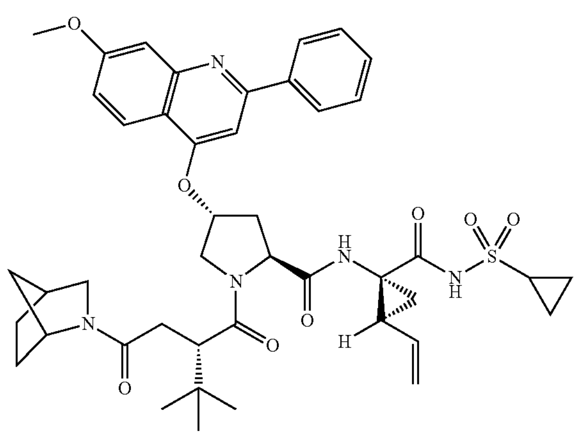 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC2CCC1C2)C(C)(C)C)C(=O)NS(=O)(=O)C1CC1] | (2S,4R)-1-((2S)-2-(2-(2-azabi-cyclo[2.2.1]heptan-2-yl)-2-oxoethyl)-3,3-dimethylbutanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 1.62 | 812 |

TABLE I-continued

| Cpd. | STRUCTURE | Name | EC50 | rt | MS + 1 |
|---|---|---|---|---|---|
| 80. | 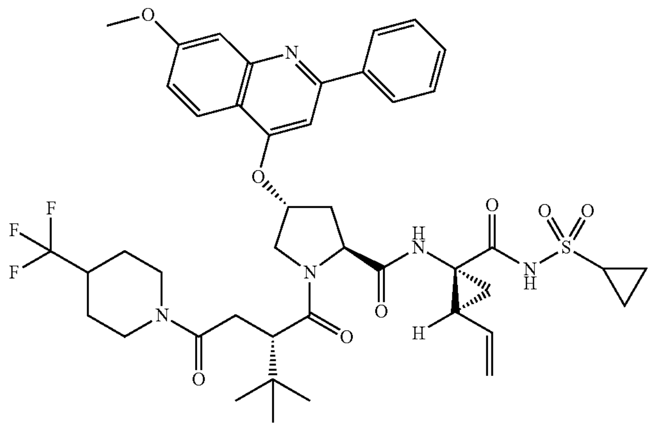 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoromethyl)piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 2.12 | 868 |
| 81. | 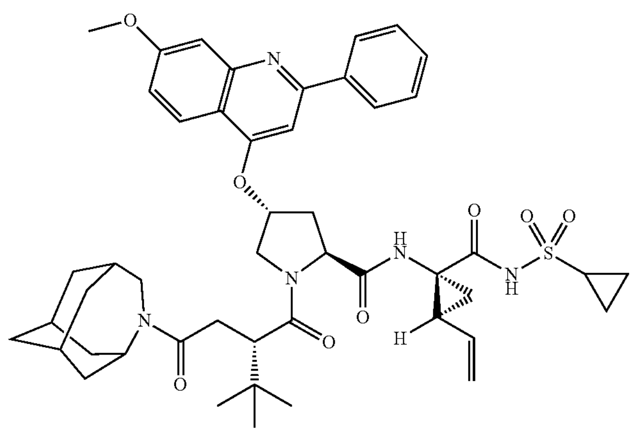 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC2CC3CC(C2)CC1C3)C(C)(C)C)C(=O)NS(=O)(=O)C1CC1] | | *** | 1.73 | 867 |
| 82. | 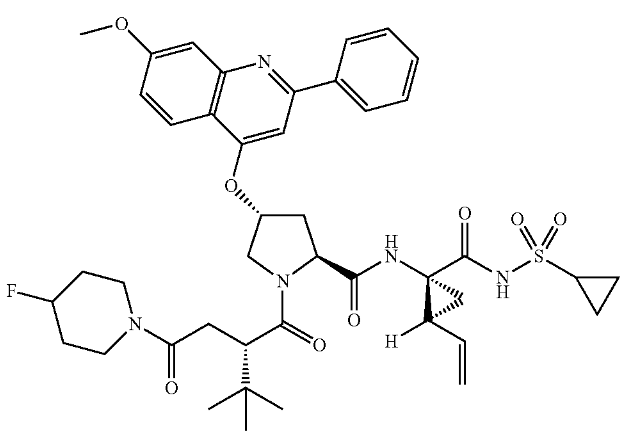 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(F)CC1)C(C)(C)C)C(=O)NS(=O)(=O)C1CC1] | (2S,4R)-1-((S)-2-tert-butyl-4-(4-fluoropiperidin-1-yl)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.49 | 818 |

TABLE I-continued

| Cpd. | STRUCTURE | Name | EC50 | rt | MS + 1 |
|---|---|---|---|---|---|
| 83. | 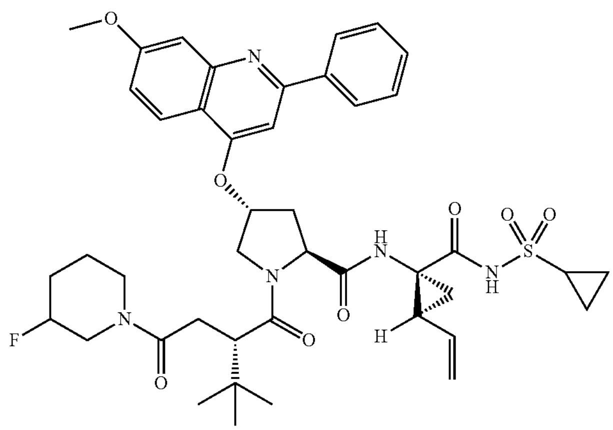 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC(F)C1)C(C)(C)C)C(=O)NS(=O)(=O)C1CC1] | (2S,4R)-1-((2S)-2-tert-butyl-4-(3-fluoropiperidin-1-yl)-4-oxobutanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 1.51 | 818 |
| 84. | 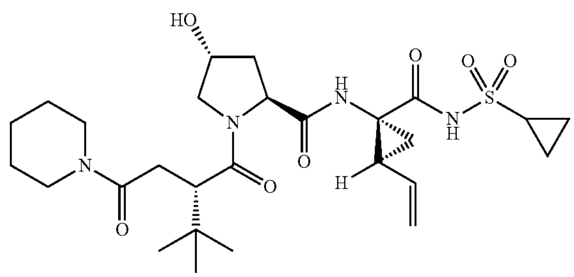 [SMILES: C=C[C@@H]1C[C@]1(NC(=O)[C@@H]1C[C@@H](O)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclo-propylsulfonyl-carbamoyl)-2-vinylcyclopropyl)-4-hydroxypyrrolidine-2-carboxamide | ** | 3.63 | 567 |
| 85. | 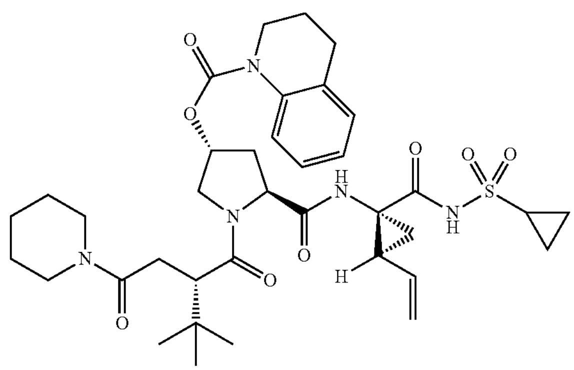 [SMILES: C=C[C@@H]1C[C@]1(NC(=O)[C@@H]1C[C@@H](OC(=O)N2CCCc3ccccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclo-propylsulfonyl-carbamoyl)-2-vinylcyclopropyl-carbamoyl)pyrrolidin-3-yl 3,4-dihydroisoquinoline-2(1H)-carboxylate | *** | 3.79 | 727 |
| 86. | 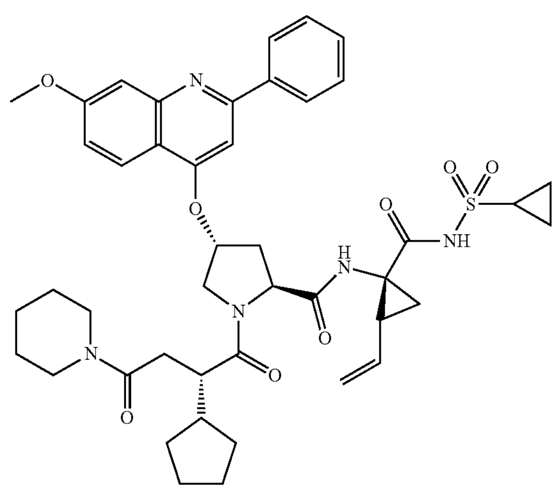 | (2S,4R)-1-((S)-2-cyclopentyl-4-oxo-4-(piperidin-1-yl)butanoyl)-N-((1R,2R)-1-(cyclo-propylsulfonyl-carbamoyl)-2-vinylcyclopropyl)-4-(7-methoxy-2-phenylquinolin-4-yloxy)pyrrolidine-2-carboxamide | *** | 3.11 | 812 |

TABLE I-continued

| Cpd. | STRUCTURE | Name | EC50 | rt | MS + 1 |
|---|---|---|---|---|---|
| 87. | 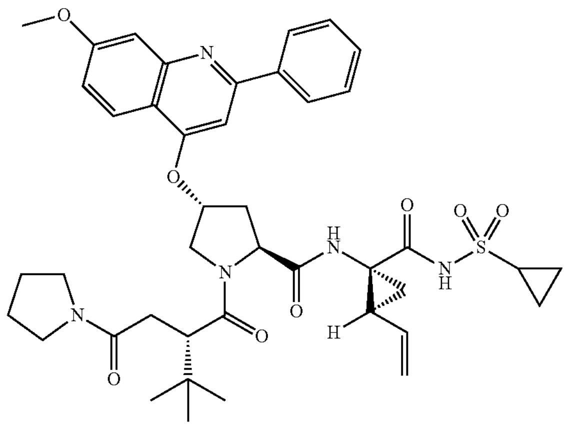 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC1)C(C)(C)C)C(=O)NS(=O)(=O)C1CC1] | (2S,4R)-1-((S)-2-tert-butyl-4-oxo-4-(pyrrolidin-1-yl)butanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.43 | 786 |
| 88. | 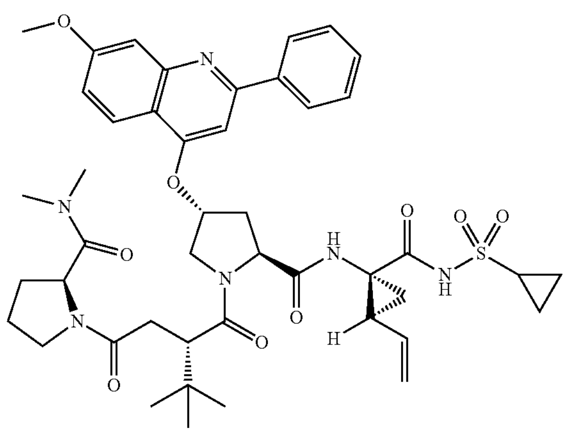 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC[C@H]1C(=O)N(C)C)C(C)(C)C)C(=O)NS(=O)(=O)C1CC1] | (2S,4R)-1-((S)-2-tert-butyl-4-((S)-2-(dimethylcarbamoyl)pyrrolidin-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.25 | 858 |
| 89. | 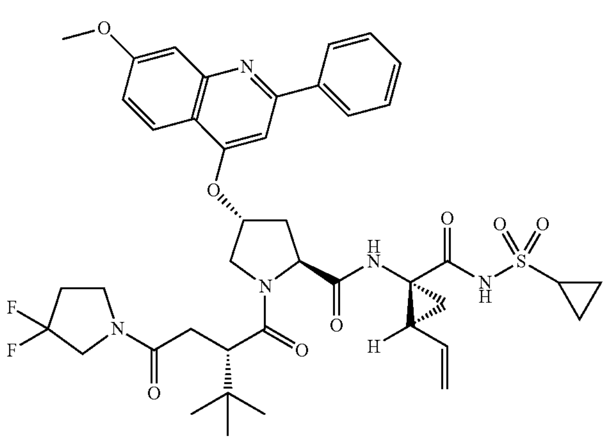 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(F)(F)C1)C(C)(C)C)C(=O)NS(=O)(=O)C1CC1] | (2S,4R)-1-((S)-2-tert-butyl-4-(3,3-difluoropyrrolidin-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.48 | 822 |

| Cpd. | STRUCTURE | Name | EC50 | rt | MS + 1 |
|---|---|---|---|---|---|
| 90. | 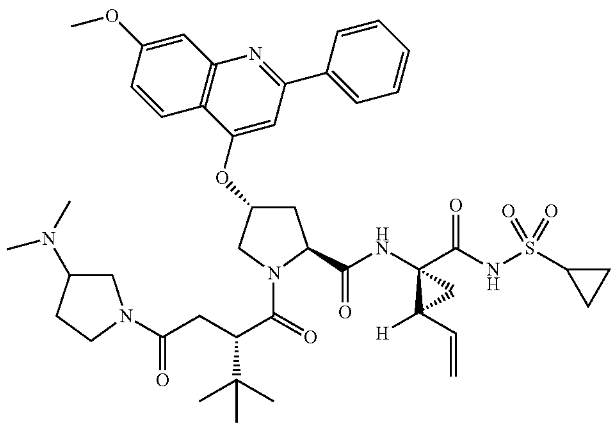 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(N(C)C)C1)C(C)(C)C)C(=O)NS(=O)(=O)C1CC1] | (2S,4R)-1-((2S)-2-tert-butyl-4-(3-(dimethylamino)pyrrolidin-1-yl)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | ** | 1.65 | 830 |
| 91. | 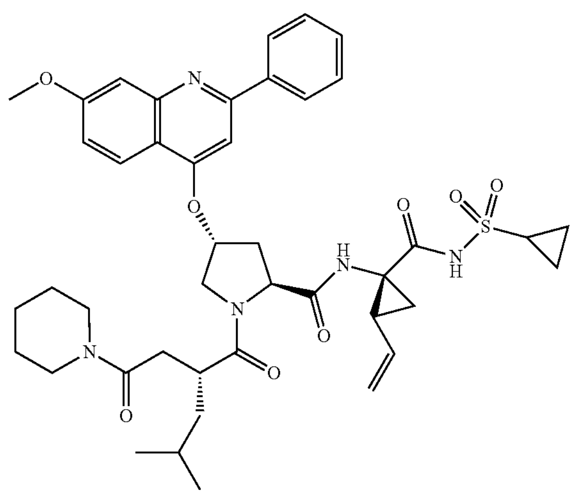 | (2S,4R)-N-((1R,2R)-1-(cyclopropylsulfonylcarbamoyl)-2-vinylcyclopropyl)-4-(7-methoxy-2-phenylquinolin-4-yloxy)-1-((R)-4-methyl-2-(2-oxo-2-(piperidin-1-yl)ethyl)pentanoyl)pyrrolidine-2-carboxamide | *** | 3.1 | 800 |
| 92. | 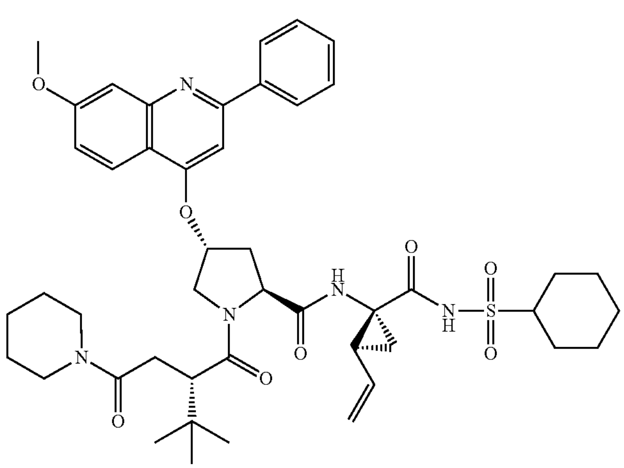 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CCCCC1] | (2S,4R)-1-((S)-2-tert-butyl-4-oxo-4-(piperidin-1-yl)butanoyl)-N-((1R,2S)-1-(cyclohexylsulfonylcarbamoyl)-2-vinylcyclopropyl)-4-(7-methoxy-2-phenylquinolin-4-yloxy)pyrrolidine-2-carboxamide | *** | 1.72 | 842 |

TABLE I-continued

| Cpd. | STRUCTURE | Name | EC50 | rt | MS + 1 |
|---|---|---|---|---|---|
| 93. | 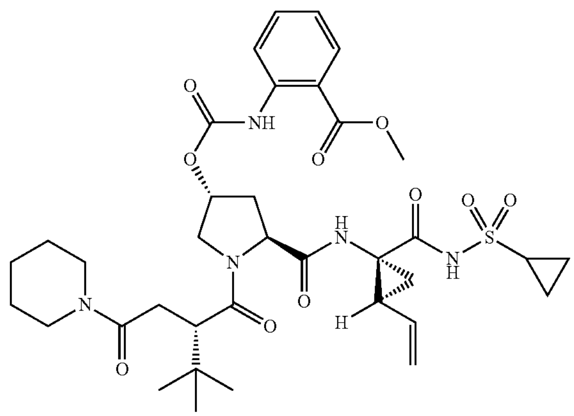 [SMILES: C=C[C@@H]1C[C@]1(NC(=O)[C@@H]1C[C@@H](OC(=O)Nc2ccccc2C(=O)OC)CN1C(=O)[C@@H](CC(=O)N1CCCCC1)C(C)(C)C)C(=O)NS(=O)(=O)C1CC1] | methyl 2-(((3R,5S)-1-((S)-2-tert-butyl-4-oxo-4-(piperidin-1-yl)butanoyl)-5-((1R,2S)-1-(cyclopropylsulfonyl-carbamoyl)-2-vinylcyclopropyl-carbamoyl)pyrrolidin-3-yloxy)carbonyl-amino)benzoate | *** | 2.81 | 745 |
| 94. | 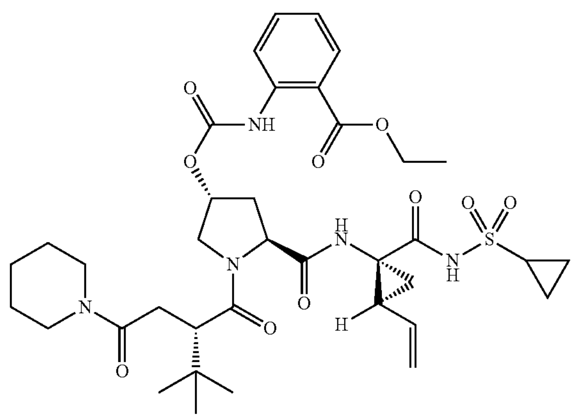 [SMILES: C=C[C@@H]1C[C@]1(NC(=O)[C@@H]1C[C@@H](OC(=O)Nc2ccccc2C(=O)OCC)CN1C(=O)[C@@H](CC(=O)N1CCCCC1)C(C)(C)C)C(=O)NS(=O)(=O)C1CC1] | ethyl 2-(((3R,5S)-1-((S)-2-tert-butyl-4-oxo-4-(piperidin-1-yl)butanoyl)-5-((1R,2S)-1-(cyclopropylsulfonyl-carbamoyl)-2-vinylcyclopropyl-carbamoyl)pyrrolidin-3-yloxy(carbonyl-amino)benzoate | *** | 4.2 | 759 |
| 95. | 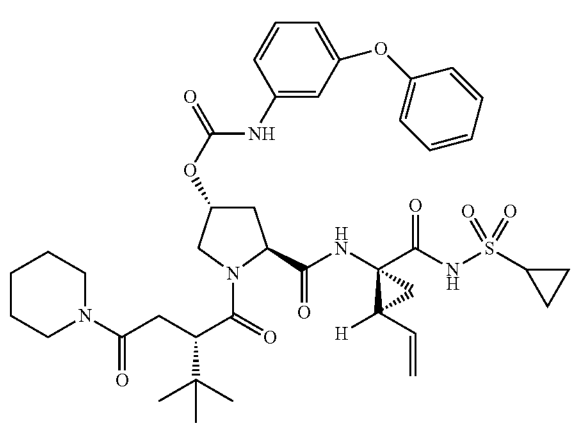 [SMILES: C=C[C@@H]1C[C@]1(NC(=O)[C@@H]1C[C@@H](OC(=O)Nc2cccc(Oc3ccccc3)c2)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonyl-carbamoyl)-2-vinylcyclopropyl-carbamoyl)pyrrolidin-3-yl 3-phenoxyphenyl-carbamate | ** | 4.25 | 778 |

TABLE I-continued

| Cpd. | STRUCTURE | Name | EC50 | rt | MS + 1 |
|---|---|---|---|---|---|
| 96. | 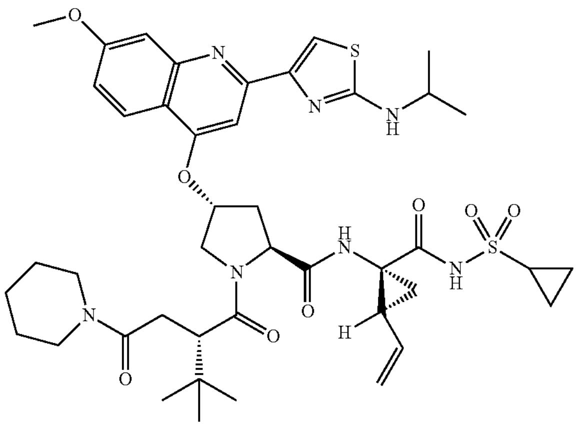 [SMILES: C=C[C@@H]1C[C@]1(NC(=O)[C@@H]1C[C@@H](Oc2cc(-c3csc(NC(C)C)n3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(2-(2-(isopropyl-amino)thiazol-4-yl)-7-methoxyquinolin-4-yloxy)pyrrolidine-2-carboxamide | *** | 3.45 | 864 |
| 97. | 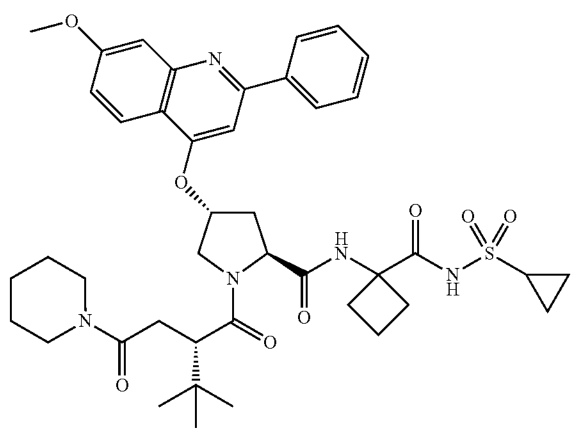 [SMILES: COc1ccc2c(O[C@@H]3C[C@@H](C(=O)NC4(C(=O)NS(=O)(=O)C5CC5)CCC4)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-(1-(cyclopropylsulfonyl-carbamoyl)cyclo-butyl)-4-(7-methoxy-2-phenylquinolin-4-yloxy)pyrrolidine-2-carboxamide | ** | 1.51 | 788 |
| 98. | 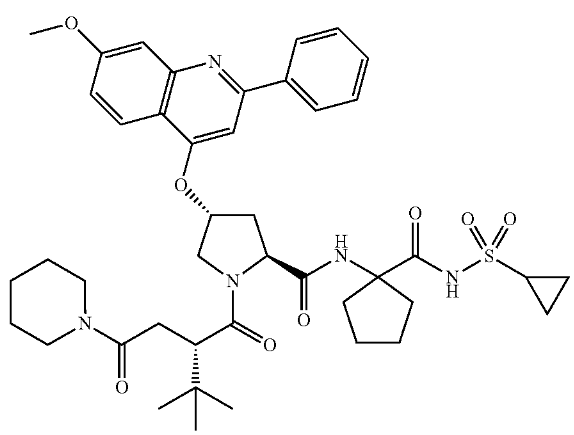 [SMILES: COc1ccc2c(O[C@@H]3C[C@@H](C(=O)NC4(C(=O)NS(=O)(=O)C5CC5)CCCC4)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-(1-(cyclopropylsulfonyl-carbamoyl)cyclo-pentyl)-4-(7-methoxy-2-phenylquinolin-4-yloxy)pyrrolidine-2-carboxamide | ** | 1.54 | 802 |

TABLE I-continued

| Cpd. | STRUCTURE | Name | EC50 | rt | MS + 1 |
|---|---|---|---|---|---|
| 99. | 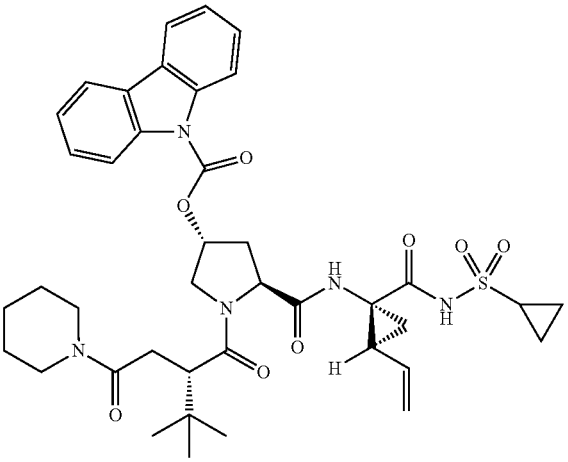 [SMILES: C=C[C@@H]1C[C@]1(NC(=O)[C@@H]1C[C@@H](OC(=O)n2c3ccccc3c3ccccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonyl-carbamoyl)-2-vinyl-cyclopropyl-carbamoyl)pyrrolidin-3-yl 9H-carbazole-9-carboxylate | *** | 3.25 | 761 |
| 100. | 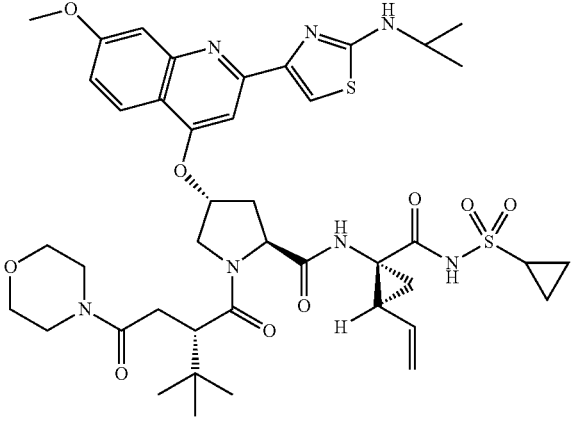 [SMILES: C=C[C@@H]1C[C@]1(NC(=O)[C@@H]1C[C@@H](Oc2cc(-c3csc(NC(C)C)n3)nc3cc(OC)ccc23)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-N-((1R,2S)-1-(cyclopropylsulfonyl-carbamoyl)-2-vinylcyclopropyl)-4-(2-(2-(isopropyl-amino)thiazol-4-yl)-7-methoxyquinolin-4-yloxy)pyrrolidine-2-carboxamide | *** | 2.97 | 866.5 |
| 101. | 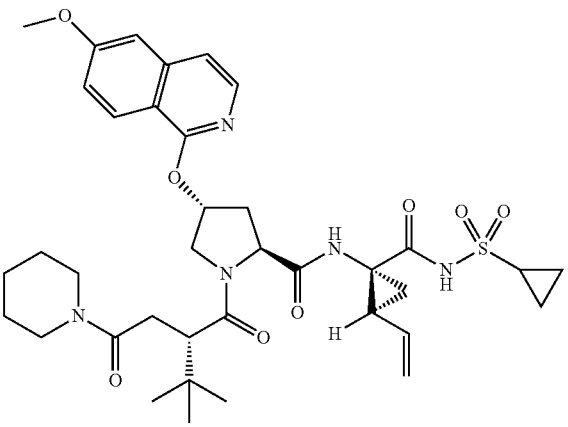 [SMILES: C=C[C@@H]1C[C@]1(NC(=O)[C@@H]1C[C@@H](Oc2nccc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(6-methoxyisoquinolin-1-yloxy)pyrrolidine-2-carboxamide | *** | 1.93 | |

TABLE I-continued

| Cpd. | STRUCTURE | Name | EC50 | rt | MS + 1 |
|---|---|---|---|---|---|
| 102. | 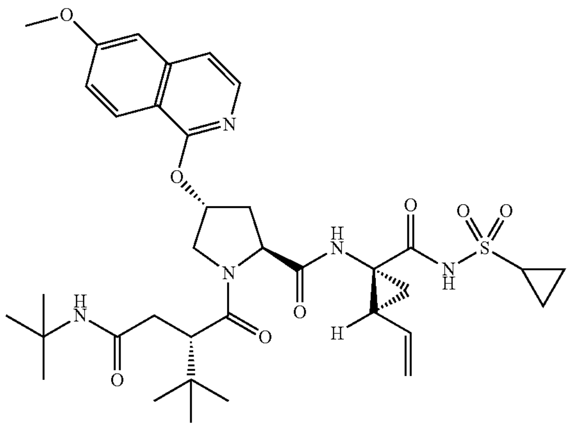 [SMILES: C=C[C@@H]1C[C@]1(NC(=O)[C@@H]1C[C@@H](Oc2nccc3cc(OC)ccc23)CN1C(=O)[C@@H](CC(=O)NC(C)(C)C)C(C)(C)C)C(=O)NS(=O)(=O)C1CC1] | (2S,4R)-1-((S)-2-tert-butyl-4-(tert-butylamino)-4-oxobutanoyl)-N-((1R,2S)-1-(cyclopropylsulfonyl-carbamoyl)-2-vinylcyclopropyl)-4-(6-methoxyisoquinolin-1-yloxy)pyrrolidine-2-carboxamide | | | |
| 103. | 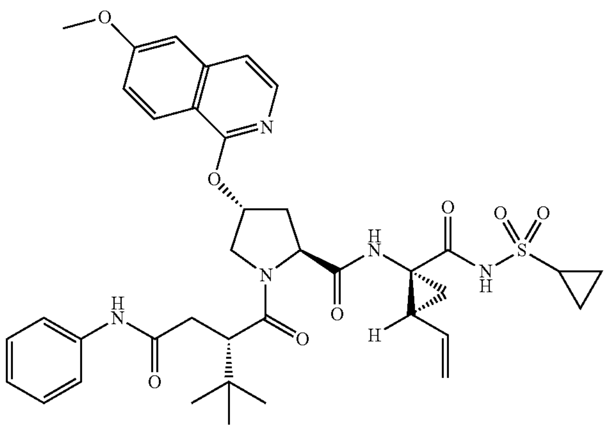 [SMILES: C=C[C@@H]1C[C@]1(NC(=O)[C@@H]1C[C@@H](Oc2nccc3cc(OC)ccc23)CN1C(=O)[C@@H](CC(=O)Nc1ccccc1)C(C)(C)C)C(=O)NS(=O)(=O)C1CC1] | (2S,4R)-1-((S)-2-tert-butyl-4-oxo-4-(phenyl-amino)butano-yl)-N-((1R,2S)-1-(cyclopropylsulfonyl-carbamoyl)-2-vinyl-cyclopropyl)-4-(6-methoxyisoquinolin-1-yloxy)pyrrolidine-2-carboxamide | | | |
| 104. | 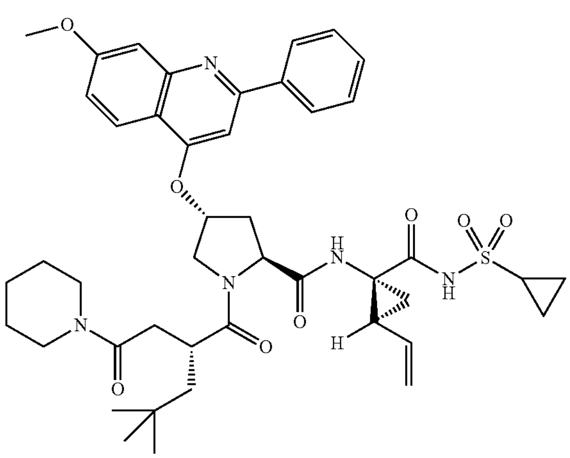 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)CC(C)(C)C)C(=O)NS(=O)(=O)C1CC1] | (2S,4R)-N-((1R,2S)-1-(cyclopropyl-sulfonylcarbamoyl)-2-vinylcyclopropyl)-1-((R)-4,4-dimethyl-2-(2-oxo-2-(piperidin-1-yl)ethyl)pentanoyl)-4-(7-methoxy-2-phenylquinolin-4-yloxy)pyrrolidine-2-carboxamide | *** | 3.17 | 814 |

TABLE I-continued

| Cpd. | STRUCTURE | Name | EC50 | rt | MS + 1 |
|---|---|---|---|---|---|
| 105. | 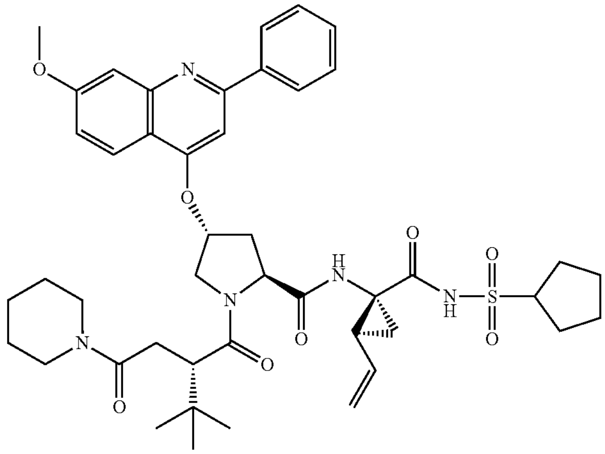 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CCCC1] | (2S,4R)-1-((S)-2-tert-butyl-4-oxo-4-(piperidin-1-yl)butanoyl)-N-((1R,2S)-1-(cyclopentyl-sulfonylcarbamoyl)-2-vinylcyclopropyl)-4-(7-methoxy-2-phenylquinolin-4-yloxy)pyrrolidine-2-carboxamide | *** | 1.71 | 828 |
| 106. | 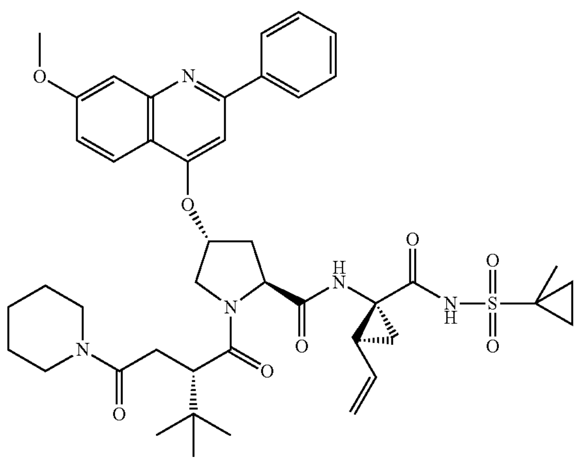 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1(C)CC1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(1-methylcyclopropyl-sulfonylcarbamoyl)-2-vinylcyclopropyl)pyrrolidine-2-carboxamide | *** | 1.58 | 814 |
| 107. | 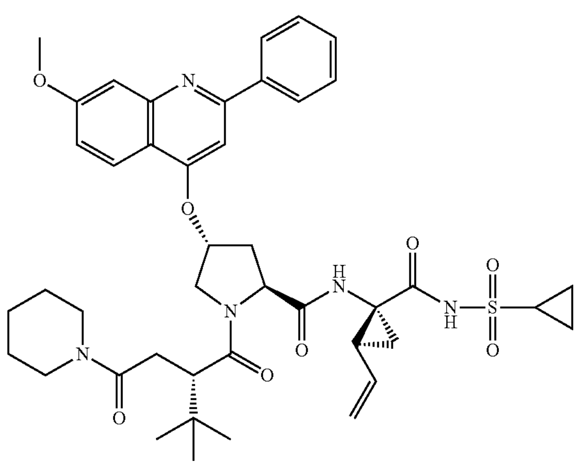 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(N-cyclopropyl-sulfamoyl-carbamoyl)-2-vinylcyclopropyl)-4-(7-methoxy-2-phenylquinolin-4-yloxy)pyrrolidine-2-carboxamide | *** | 1.58 | 815 |

| Cpd. | STRUCTURE | Name | EC50 | rt | MS + 1 |
|---|---|---|---|---|---|
| 108. | 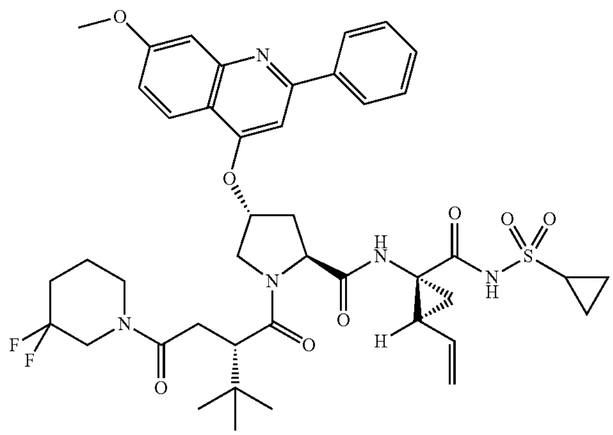 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.57 | 836 |
| 109. | 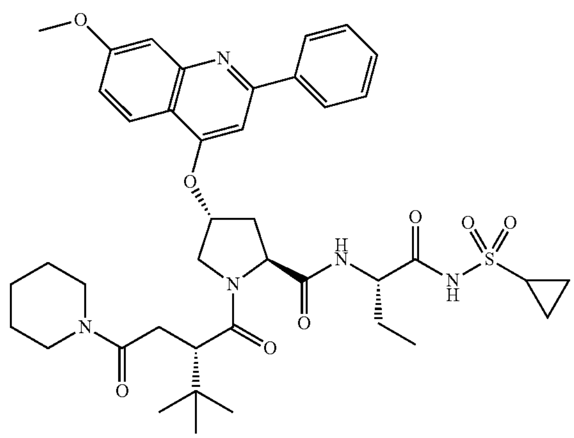 [SMILES: CC[C@H](NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((S)-1-(cyclopropanesulfonamido)-1-oxobutan-2-yl)-4-(7-methoxy-2-phenylquinolin-4-yloxy)pyrrolidine-2-carboxamide | ** | 1.45 | 776 |
| 110. | 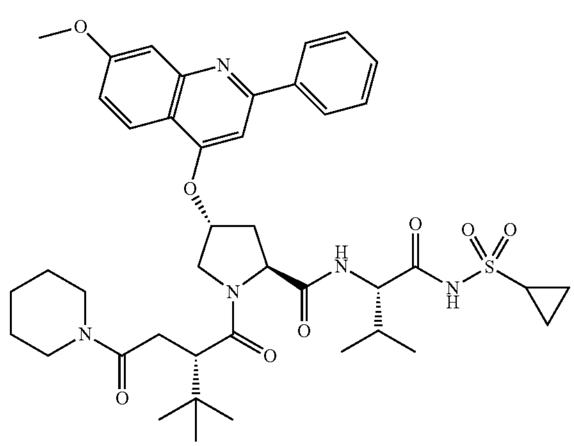 [SMILES: COc1ccc2c(O[C@@H]3C[C@@H](C(=O)N[C@H](C(=O)NS(=O)(=O)C4CC4)C(C)C)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-((S)-1-(cyclopropanesulfonamido)-3-methyl-1-oxobutan-2-yl)-4-(7-methoxy-2-phenylquinolin-4-yloxy)pyrrolidine-2-carboxamide | ** | 1.5 | 790 |

TABLE I-continued

| Cpd. | STRUCTURE | Name | EC50 | rt | MS + 1 |
|---|---|---|---|---|---|
| 111. | 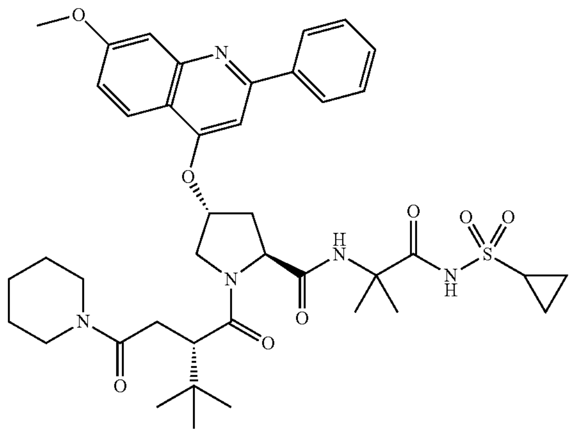 [SMILES: COc1ccc2c(O[C@@H]3C[C@@H](C(=O)NC(C)(C)C(=O)NS(=O)(=O)C4CC4)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-(1-(cyclopropane-sulfonamido)-2-methyl-1-oxopropan-2-yl)-4-(7-methoxy-2-phenylquinolin-4-yloxy)pyrrolidine-2-carboxamide | ** | 1.46 | 776 |
| 112. | 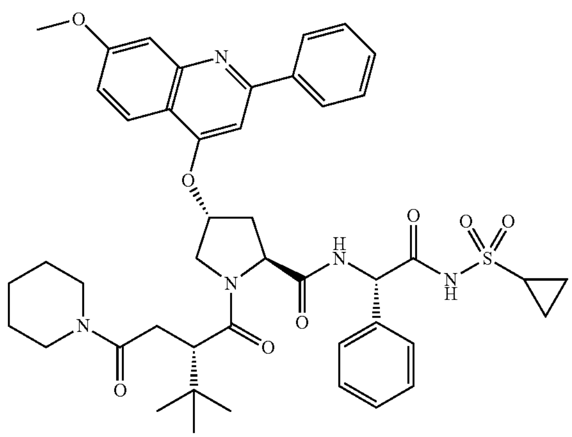 [SMILES: COc1ccc2c(O[C@@H]3C[C@@H](C(=O)N[C@H](C(=O)NS(=O)(=O)C4CC4)c4ccccc4)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-((S)-2-(cyclopropane-sulfonamido)-2-oxo-1-phenylethyl)-4-(7-methoxy-2-phenylquinolin-4-yloxy)pyrrolidine-2-carboxamide | ** | 1.51 | 825 |
| 113. | 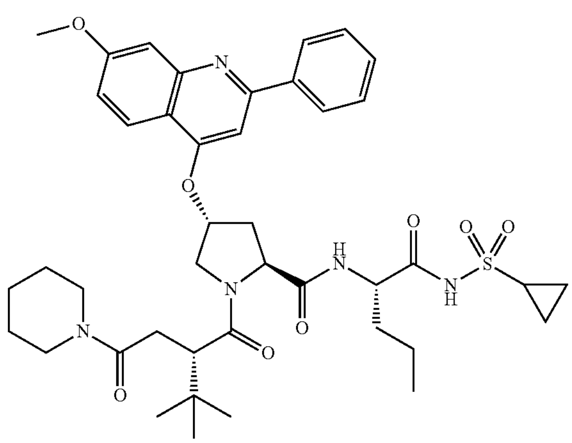 [SMILES: CCC[C@H](NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((S)-1-(cyclopropanesulfon-amido)-1-oxopentan-2-yl)-4-(7-methoxy-2-phenylquinolin-4-yloxy)pyrrolidine-2-carboxamide | ** | 1.51 | 790 |

TABLE I-continued

| Cpd. | STRUCTURE | Name | EC50 | rt | MS + 1 |
|---|---|---|---|---|---|
| 114. | 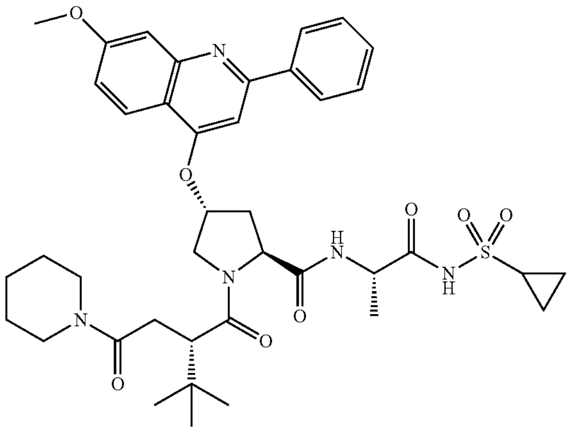 [SMILES: COc1ccc2c(O[C@@H]3C[C@@H](C(=O)N[C@@H](C)C(=O)NS(=O)(=O)C4CC4)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-((S)-1-(cyclopropanesulfon-amido)-1-oxopropan-2-yl)-4-(7-methoxy-2-phenylquinolin-4-yloxy)pyrrolidine-2-carboxamide | ** | 1.39 | 762 |
| 115. | 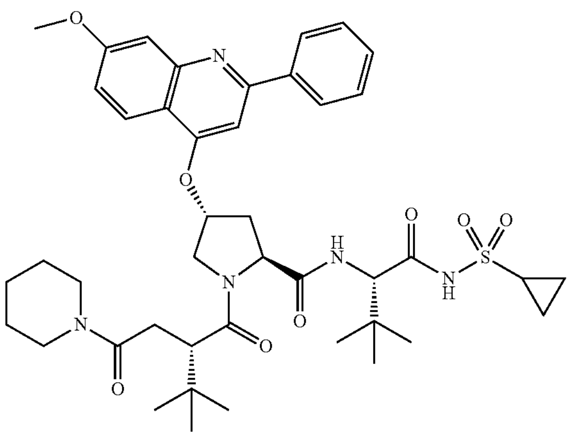 [SMILES: COc1ccc2c(O[C@@H]3C[C@@H](C(=O)N[C@H](C(=O)NS(=O)(=O)C4CC4)C(C)(C)C)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-((S)-1-(cyclopropanesulfon-amido)-3,3-dimethyl-1-oxobutan-2-yl)-4-(7-methoxy-2-phenylquinolin-4-yloxy)pyrrolidine-2-carboxamide | ** | 1.56 | 805 |
| 116. | 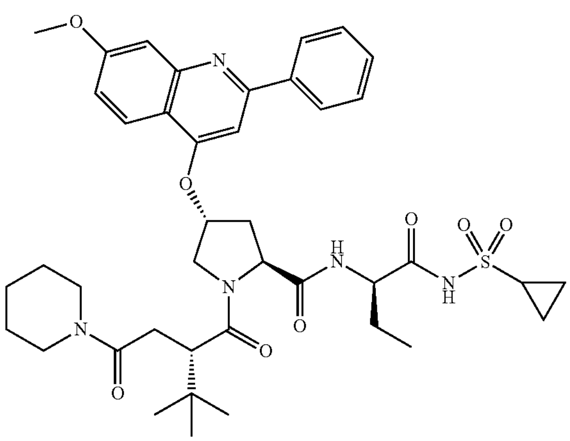 [SMILES: CC[C@@H](NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((R)-1-(cyclopropanesulfon-amido)-1-oxobutan-2-yl)-4-(7-methoxy-2-phenylquinolin-4-yloxy)pyrrolidine-2-carboxamide | ** | 1.48 | 777 |

TABLE I-continued

| Cpd. | STRUCTURE | Name | EC50 | rt | MS + 1 |
|---|---|---|---|---|---|
| 117. | 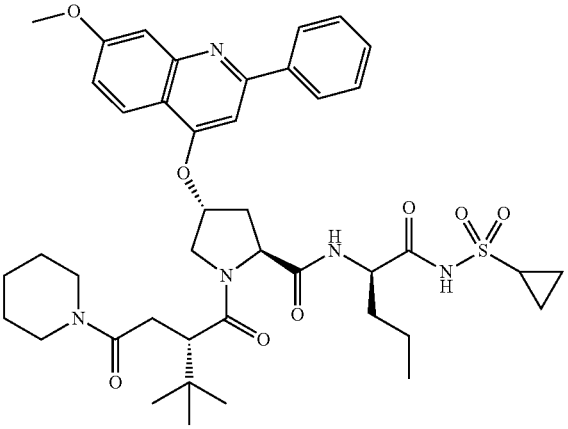 [SMILES: CCC[C@@H](NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((R)-1-(cyclopropanesulfon-amido)-1-oxopentan-2-yl)-4-(7-methoxy-2-phenylquinolin-4-yloxy)pyrrolidine-2-carboxamide | ** | 1.55 | 791 |
| 118. | 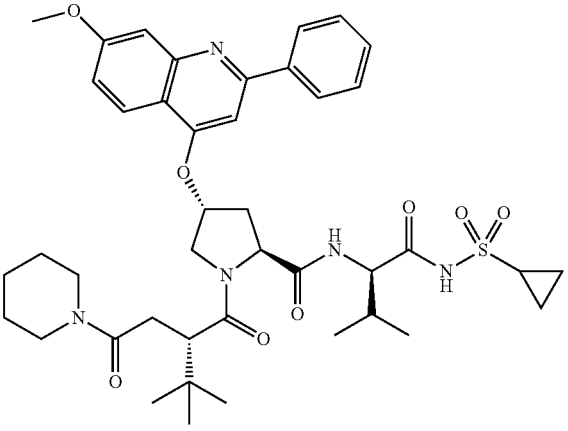 [SMILES: COc1ccc2c(O[C@@H]3C[C@@H](C(=O)N[C@@H](C(=O)NS(=O)(=O)C4CC4)C(C)C)N(C(=O)[C@@H](CC(=O)N4CCCCC4)C(C)(C)C)C3)cc(-c3ccccc3)nc2c1] | (2S,4R)-1-((S)-2-tert-butyl-4-oxo-4-(piperidin-1-yl)butanoyl)-N-((R)-1-(cyclopropanesulfon-amido)-3-methyl-1-oxobutan-2-yl)-4-(7-methoxy-2-phenylquinolin-4-yloxy)pyrrolidine-2-carboxamide | ** | 1.55 | 791 |
| 119. | 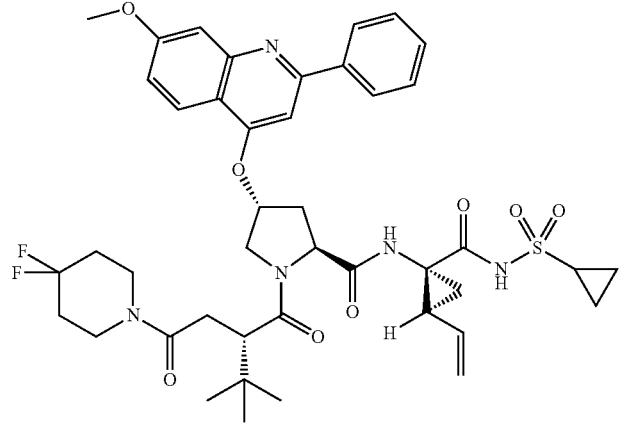 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(F)(F)CC1)C(C)(C)C)C(=O)NS(=O)(=O)C1CC1] | (2S,4R)-1-((S)-2-tert-butyl-4-(4,4-difluoropiperidin-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.55 | 837 |

TABLE I-continued

| Cpd. | STRUCTURE | Name | EC50 | rt | MS + 1 |
|---|---|---|---|---|---|
| 120. | 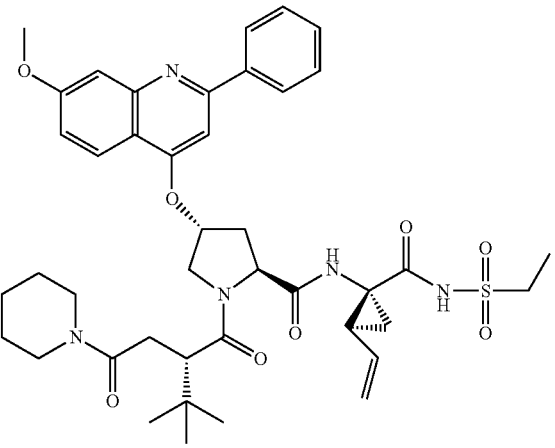 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)CC] | (2S,4R)-1-((S)-2-tert-butyl-4-oxo-4-(piperidin-1-yl)butanoyl)-N-((1R,2S)-1-(ethyl-sulfonylcarbamoyl)-2-vinylcyclopropyl)-4-(7-methoxy-2-phenylquinolin-4-yloxy)pyrrolidine-2-carboxamide | *** | 1.51 | 788 |
| 121. | 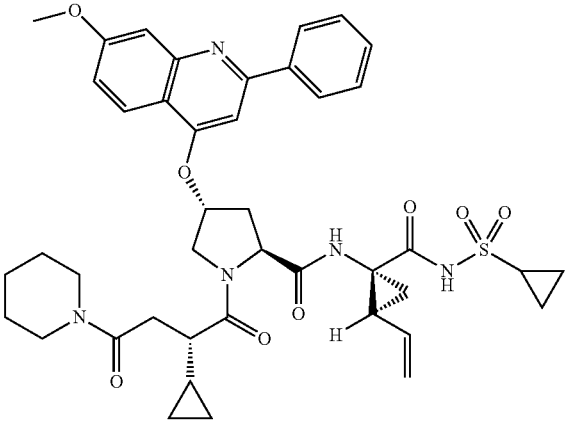 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C1CC1)C(=O)NS(=O)(=O)C1CC1] | (2S,4R)-1-((S)-2-cyclopropyl-4-oxo-4-(piperidin-1-yl)butanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 2.81 | 784 |
| 122. | 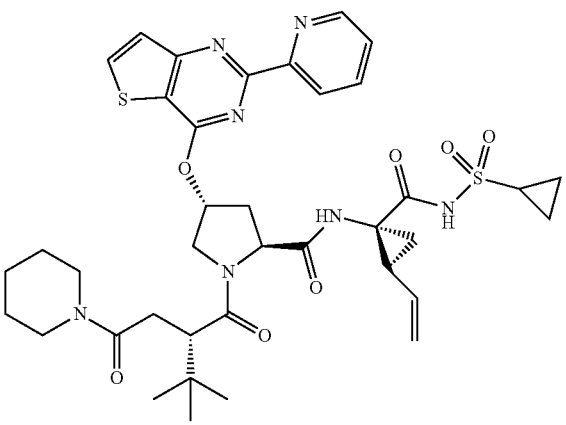 [SMILES: C=C[C@@H]1C[C@]1(NC(=O)[C@@H]1C[C@@H](Oc2nc(-c3ccccn3)nc3ccsc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(2-(pyridin-2-yl)thieno[3,2-d]pyrimidin-4-yloxy)pyrrolidine-2-carboxamide | ** | 2.7 | 778.5 |

| Cpd. | STRUCTURE | Name | EC50 | rt | MS + 1 |
|---|---|---|---|---|---|
| 123. | 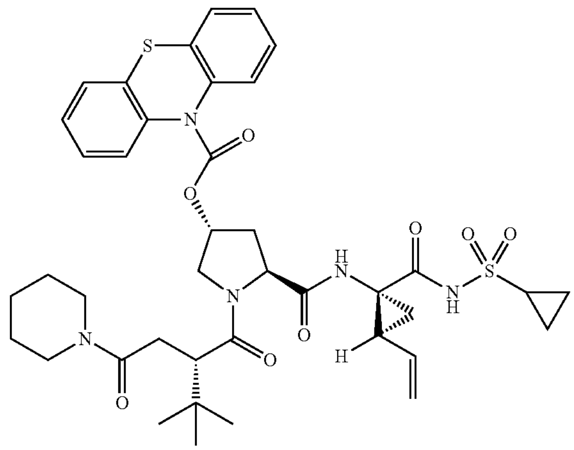 [SMILES: C=C[C@@H]1C[C@]1(NC(=O)[C@@H]1C[C@@H](OC(=O)N2c3ccccc3Sc3ccccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonyl-carbamoyl)-2-vinyl-cyclopropylcarbamoyl)pyrrolidin-3-yl 10H-phenothiazine-10-carboxylate | ** | 2.4 | 793 |
| 124. | 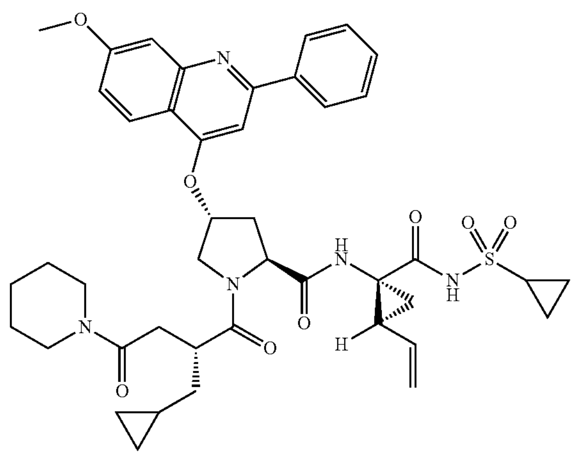 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)CC1CC1)C(=O)NS(=O)(=O)C1CC1] | (2S,4R)-1-((R)-2-(cyclopropylmethyl)-4-oxo-4-(piperidin-1-yl)butanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 2.97 | 798 |
| 125. | 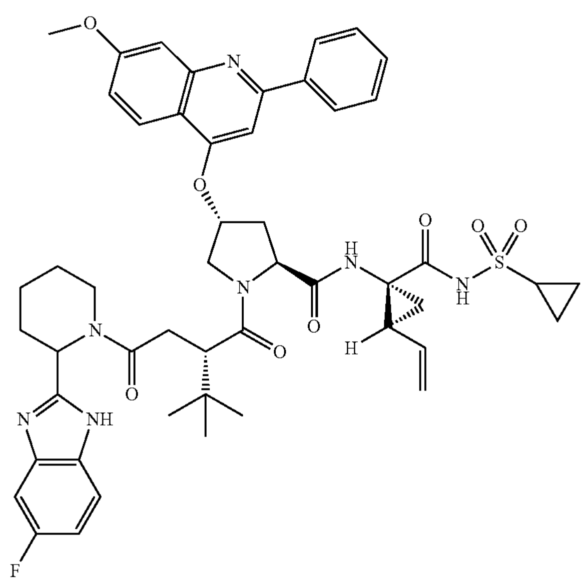 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1c1nc2cc(F)ccc2[nH]1)C(C)(C)C)C(=O)NS(=O)(=O)C1CC1] | (2S,4R)-1-((2S)-2-tert-butyl-4-(2-(5-fluoro-1H-benzo[d]imidazol-2-yl)piperidin-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.24 | 935 |

| Cpd. | STRUCTURE | Name | EC50 | rt | MS + 1 |
|---|---|---|---|---|---|
| 126. | 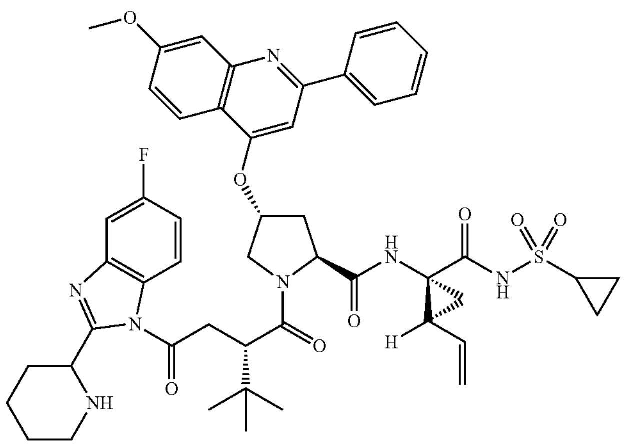 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)n1c(C2CCCCN2)nc2cc(F)ccc21)C(C)(C)C)C(=O)NS(=O)(=O)C1CC1] | (2S,4R)-1-((2S)-2-tert-butyl-4-(5-fluoro-2-(piperidin-2-yl)-1H-benzo[d]imidazol-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.35 | 935 |
| 127. | 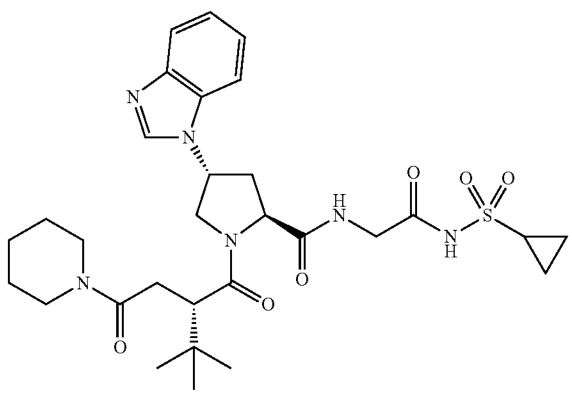 [SMILES: CC(C)(C)[C@H](CC(=O)N1CCCCC1)C(=O)N1C[C@H](n2cnc3ccccc32)C[C@H]1C(=O)NCC(=O)NS(=O)(=O)C1CC1] | (2S,4R)-4-(1H-benzo[d]imidazol-1-yl)-1-((S)-2-tert-butyl-4-oxo-4-(piperidin-1-yl)butanoyl)-N-(2-(cyclopropane-sulfonamido)-2-oxoethyl)pyrrolidine-2-carboxamide | ** | 1.27 | |
| 128. | 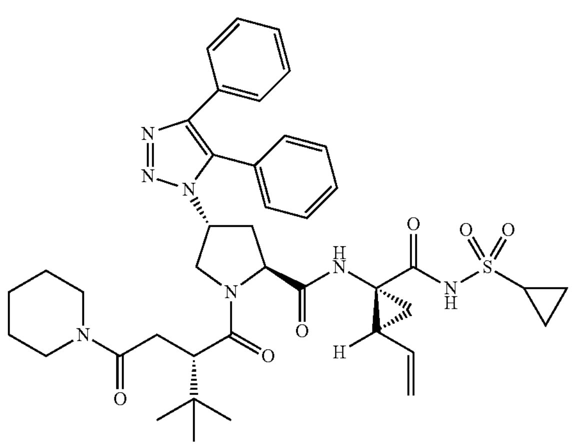 [SMILES: C=C[C@@H]1C[C@]1(NC(=O)[C@@H]1C[C@@H](n2nnc(-c3ccccc3)c2-c2ccccc2)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(4,5-diphenyl-1H-1,2,3-triazol-1-yl)pyrrolidine-2-carboxamide | ** | 2.21 | |

TABLE I-continued

| Cpd. | STRUCTURE | Name | EC50 | rt | MS + 1 |
|---|---|---|---|---|---|
| 129. | 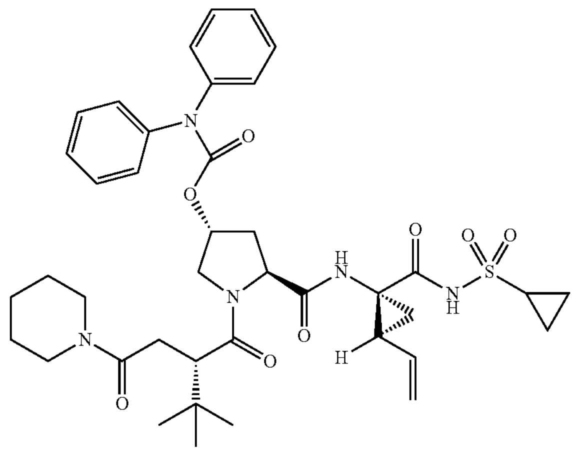 [SMILES: C=C[C@@H]1C[C@]1(NC(=O)[C@@H]1C[C@@H](OC(=O)N(c2ccccc2)c2ccccc2)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl diphenylcarbamate | ** | 2.75 | 763 |
| 130. | 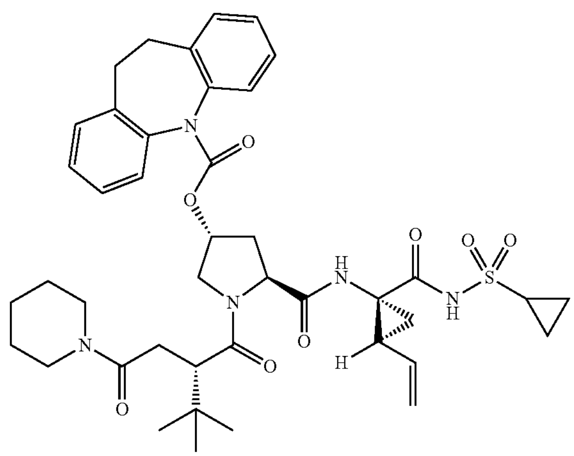 [SMILES: C=C[C@@H]1C[C@]1(NC(=O)[C@@H]1C[C@@H](OC(=O)N2c3ccccc3CCc3ccccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl 10,11-dihydro-5H-dibenzo[b,f]azepine-5-carboxylate | ** | 2.81 | 789 |
| 131. | 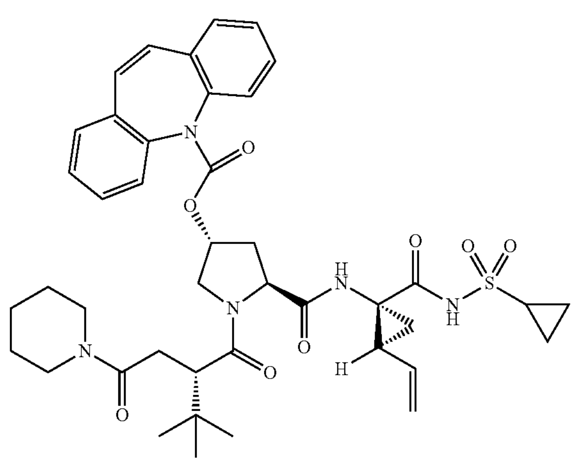 [SMILES: C=C[C@@H]1C[C@]1(NC(=O)[C@@H]1C[C@@H](OC(=O)N2c3ccccc3C=Cc3ccccc32)CN1C(=O)[C@@H](CC(=O)N1CCCCC1)C(C)(C)C)C(=O)NS(=O)(=O)C1CC1] | (Z)-((3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl)5H-dibenzo[b,f]azepine-5-carboxylate | ** | 2.81 | 787 |

TABLE I-continued

| Cpd. | STRUCTURE | Name | EC50 | rt | MS + 1 |
|---|---|---|---|---|---|
| 132. | 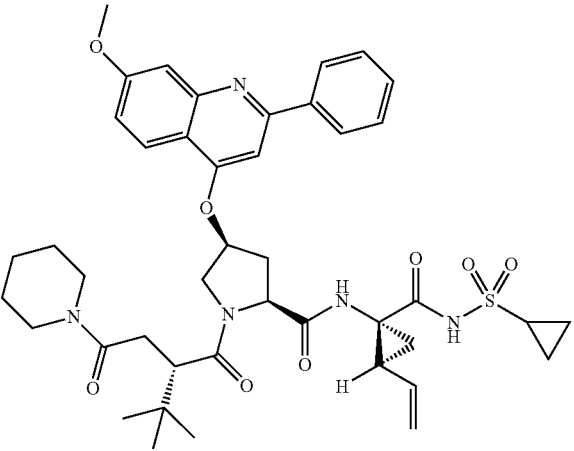 [SMILES: C=C[C@@H]1C[C@]1(NC(=O)[C@@H]1C[C@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4S)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.83 | 800 |
| 133. | 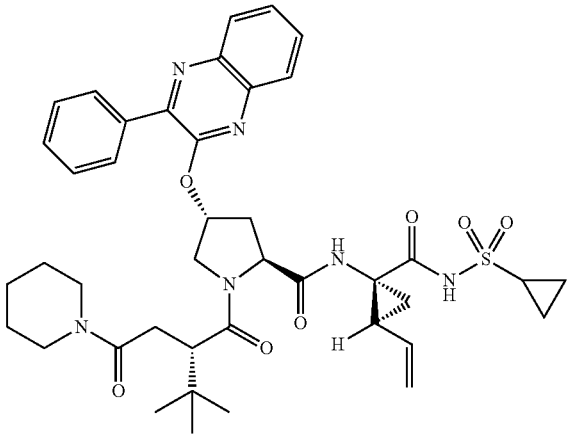 [SMILES: C=C[C@@H]1C[C@]1(NC(=O)[C@@H]1C[C@@H](Oc2nc3ccccc3nc2-c2ccccc2)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(3-phenylquinoxalin-2-yloxy)pyrrolidine-2-carboxamide | ** | | |
| 134. | 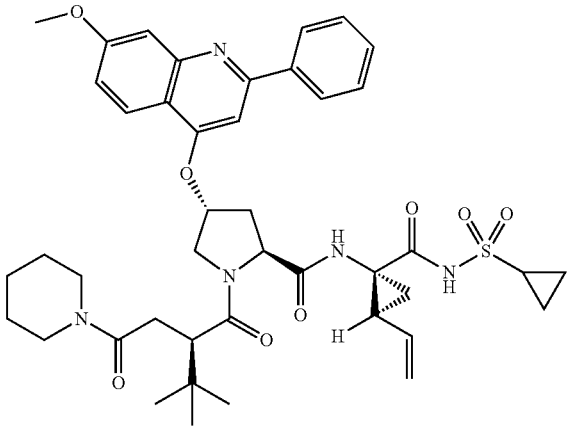 [SMILES: C=C[C@@H]1C[C@]1(NC(=O)[C@@H]1C[C@@H](Oc2cc(-c3ccccc3)nc3cc(OC)ccc23)CN1C(=O)[C@H](CC(=O)N1CCCCC1)C(C)(C)C)C(=O)NS(=O)(=O)C1CC1] | (2S,4R)-1-((R)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | ** | 2.16 | 800 |

TABLE I-continued

| Cpd. | STRUCTURE | Name | EC50 | rt | MS + 1 |
|---|---|---|---|---|---|
| 135. | 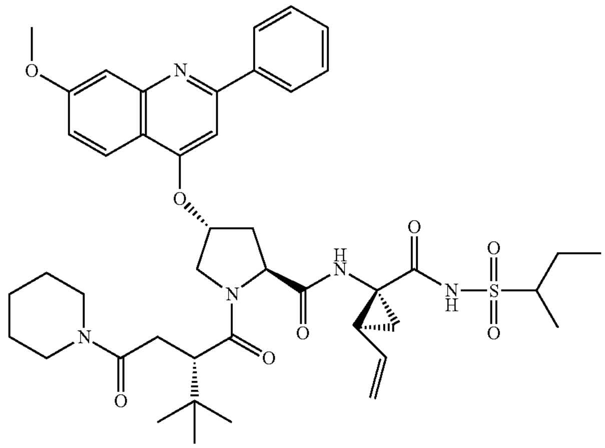 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C(C)CC] | (2S,4R)-1-((S)-2-tert-butyl-4-oxo-4-(piperidin-1-yl)butanoyl)-N-((1R,2S)-1-(sec-butylsulfonyl-carbamoyl)-2-vinylcyclopropyl)-4-(7-methoxy-2-phenylquinolin-4-yloxy)pyrrolidine-2-carboxamide | *** | 1.66 | 816 |
| 136. | 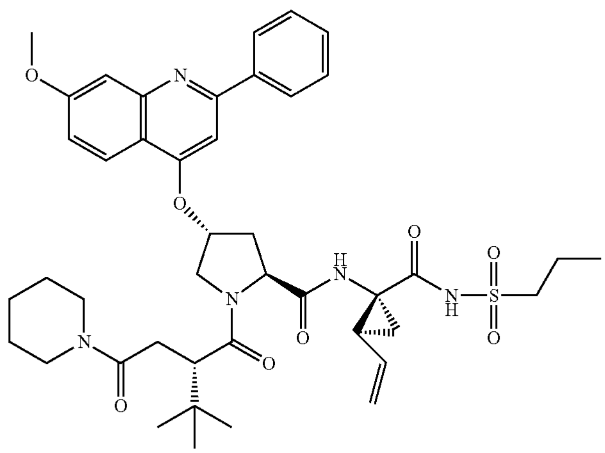 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)CCC] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(propylsulfonyl-carbamoyl)-2-vinyl-cyclopropyl)pyrrolidine-2-carboxamide | *** | 2.1 | 802 |
| 137. | 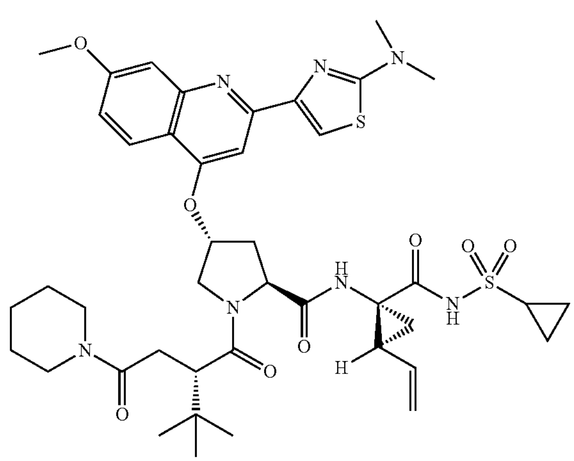 [SMILES: C=C[C@@H]1C[C@]1(NC(=O)[C@@H]1C[C@@H](Oc2cc(-c3csc(N(C)C)n3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinylcyclopropyl)-4-(2-(2-(dimethylamino)thiazol-4-yl)-7-methoxyquinolin-4-yloxy)pyrrolidine-2-carboxamide | *** | 3.03 | 850.4 |

TABLE I-continued

| Cpd. | STRUCTURE | Name | EC50 | rt | MS + 1 |
|---|---|---|---|---|---|
| 138. | 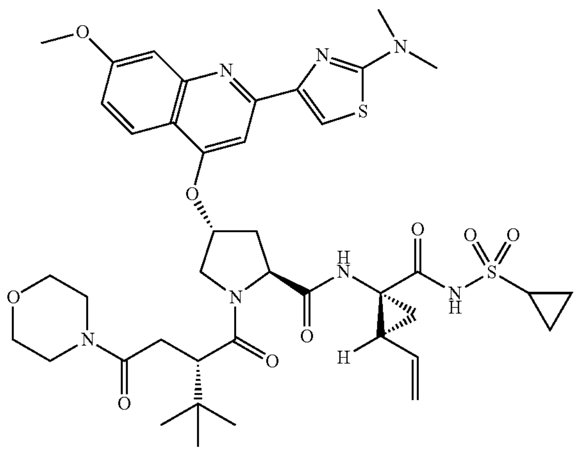 [SMILES: C=C[C@@H]1C[C@]1(NC(=O)[C@@H]1C[C@@H](Oc2cc(-c3csc(N(C)C)n3)nc3cc(OC)ccc23)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-N-((1R,2S)-1-(cyclopropylsulfonylcarbamoyl)-2-vinylcyclopropyl)-4-(2-(2-(dimethylamino)thiazol-4-yl)-7-methoxyquinolin-4-yloxy)pyrrolidine-2-carboxamide | *** | 2.73 | 852.4 |
| 139. | 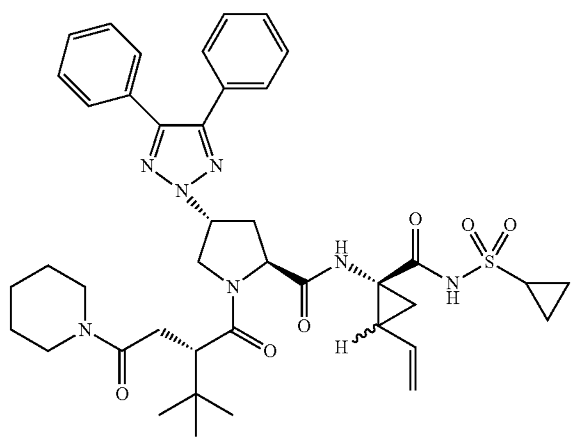 [SMILES: C=CC1C[C@]1(NC(=O)[C@@H]1C[C@@H](n2nc(-c3ccccc3)c(-c3ccccc3)n2)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(4,5-diphenyl-2H-1,2,3-triazol-2-yl)pyrrolidine-2-carboxamide | *** | 3 | |
| 140. | 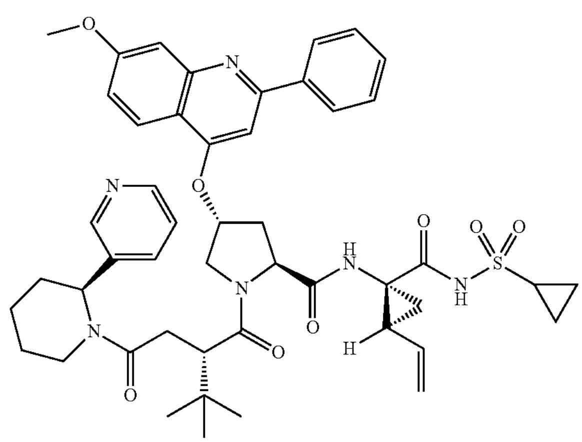 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC[C@H]1c1cccnc1)C(C)(C)C)C(=O)NS(=O)(=O)C1CC1] | (2S,4R)-1-((S)-2-tert-butyl-4-oxo-4-((S)-2-(pyridin-3-yl)piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.23 | 878 |

TABLE I-continued

| Cpd. | STRUCTURE | Name | EC50 | rt | MS + 1 |
|---|---|---|---|---|---|
| 141. | 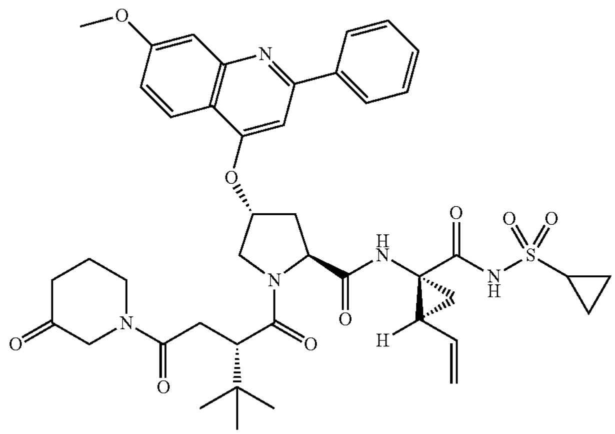 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC(=O)C1)C(C)(C)C)C(=O)NS(=O)(=O)C1CC1] | (2S,4R)-1-((S)-2-tert-butyl-4-oxo-4-(3-oxopiperidin-1-yl)butanoyl)-N-((1R,2S)-1-(cyclo-propylsulfonyl-carbamoyl)-2-vinylcyclopropyl)-4-(7-methoxy-2-phenylquinolin-4-yloxy)pyrrolidine-2-carboxamide | *** | 1.8 | 815 |
| 142. | 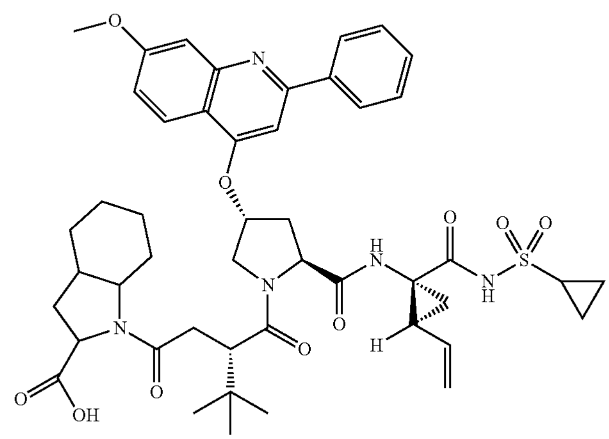 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1C(C(=O)O)CC2CCCCC21)C(C)(C)C)C(=O)NS(=O)(=O)C1CC1] | 1-((S)-3-((2S,4R)-2-((1R,2S)-1-(cyclo-propylsulfonyl-carbamoyl)-2-vinyl-cyclopropyl-carbamoyl)-4-(7-methoxy-2-phenylquinolin-4-yloxy)pyrrolidine-1-carbonyl)-4,4-dimethylpentano-yl)octahydro-1H-indole-2-carboxylic acid | *** | 1.98 | 885 |
| 143. | 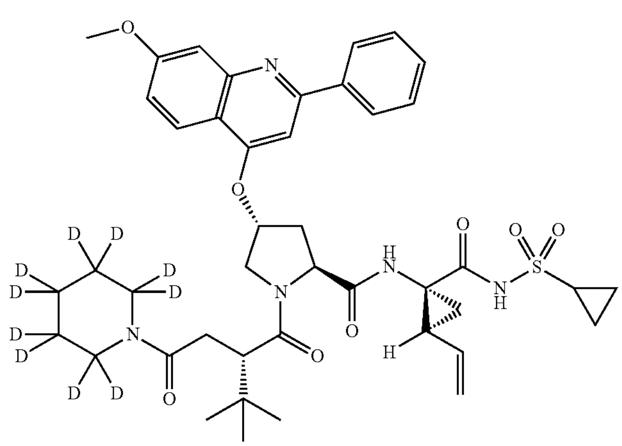 [SMILES: [2H]C1([2H])N(C(=O)C[C@H](C(=O)N2C[C@H](Oc3cc(-c4ccccc4)nc4cc(OC)ccc34)C[C@H]2C(=O)N[C@]2(C(=O)NS(=O)(=O)C3CC3)C[C@H]2C=C)C(C)(C)C)C([2H])([2H])C([2H])([2H])C([2H])([2H])C1([2H])[2H]] | | | | |

TABLE I-continued

| Cpd. | STRUCTURE | Name | EC50 | rt | MS + 1 |
| --- | --- | --- | --- | --- | --- |
| 144. | 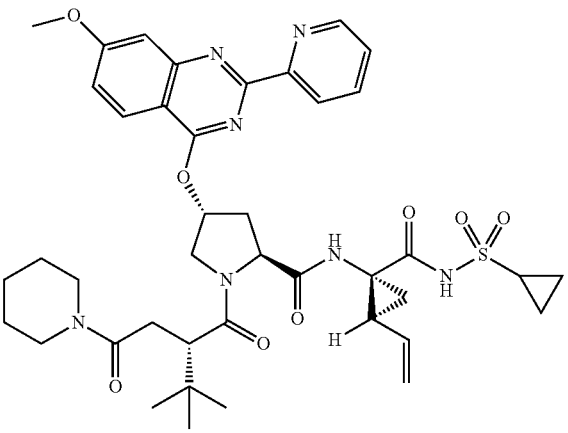 [SMILES: C=C[C@@H]1C[C@]1(NC(=O)[C@@H]1C[C@@H](Oc2nc(-c3ccccn3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-(pyridin-2-yl)quinazolin-4-yloxy)pyrrolidine-2-carboxamide | *** | 2.76 | 802.3 |
| 145. | 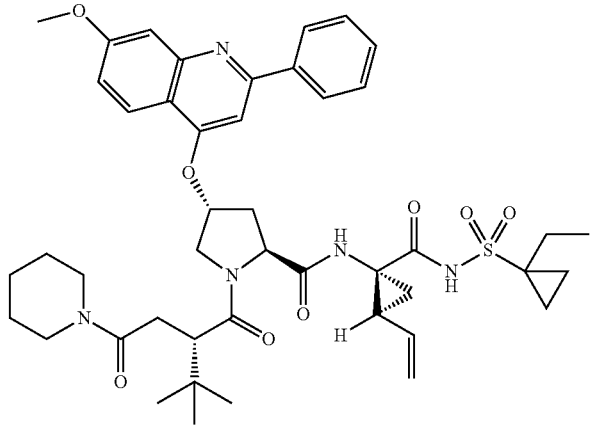 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1(CC)CC1] | (2S,4R)-1-((S)-2-tert-butyl-4-oxo-4-(piperidin-1-yl)butanoyl)-N-((1R,2S)-1-(1-ethylcyclopropylsulfonylcarbamoyl)-2-vinylcyclopropyl)-4-(7-methoxy-2-phenylquinolin-4-yloxy)pyrrolidine-2-carboxamide | *** | 2.21 | 828 |
| 146. | 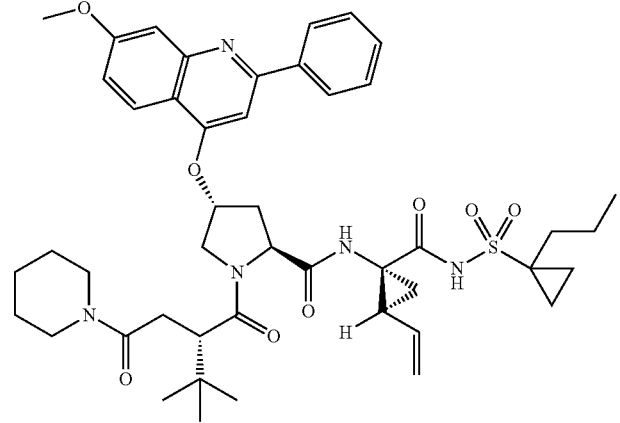 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1(CCC)CC1] | (2S,4R)-1-((S)-2-tert-butyl-4-oxo-4-(piperidin-1-yl)butanoyl)-4-(7-methoxy-2-phenylquinolin-4-yloxy)-N-((1R,2S)-1-(1-propylcyclopropylsulfonylcarbamoyl)-2-vinylcyclopropyl)pyrrolidine-2-carboxamide | *** | 2.36 | 842 |

| Cpd. | STRUCTURE | Name | EC50 | rt | MS + 1 |
|---|---|---|---|---|---|
| 147. | 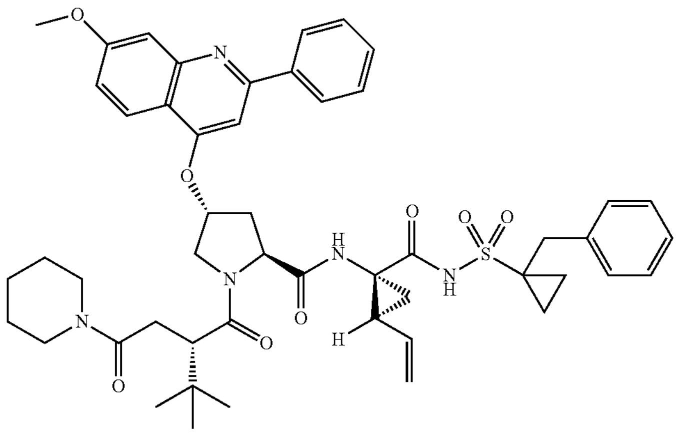 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1(Cc2ccccc2)CC1] | (2S,4R)-N-((1R,2S)-1-(1-benzylcyclopropylsulfonylcarbamoyl)-2-vinylcyclopropyl)-1-((S)-2-tert-butyl-4-oxo-4-(piperidin-1-yl)butanoyl)-4-(7-methoxy-2-phenylquinolin-4-yloxy)pyrrolidine-2-carboxamide | ** | 2.44 | 890 |
| 148. | 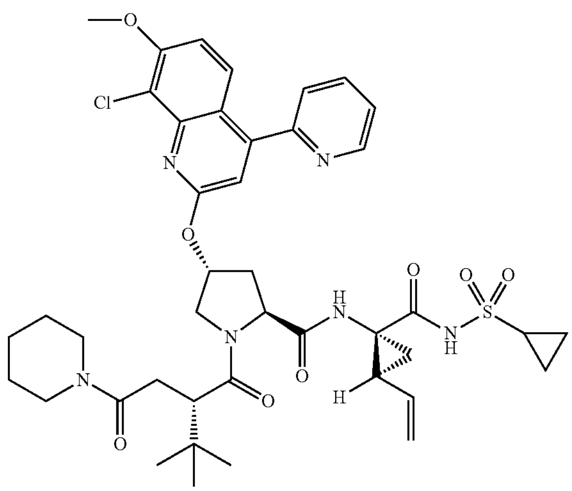 [SMILES: C=C[C@@H]1C[C@]1(NC(=O)[C@@H]1C[C@@H](Oc2cc(-c3ccccn3)c3ccc(OC)c(Cl)c3n2)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-4-(8-chloro-7-methoxy-4-(pyridin-2-yl)quinolin-2-yloxy)-N-((1R,2S)-1-(cyclopropylsulfonylcarbamoyl)-2-vinylcyclopropyl)pyrrolidine-2-carboxamide | ** | 1.87 | 835 |
| 149. | 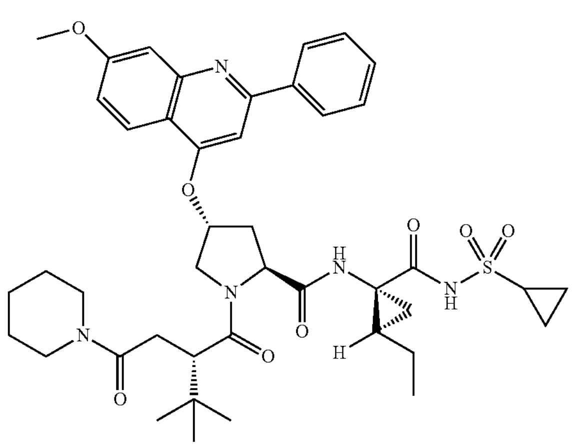 [SMILES: CC[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2R)-1-(cyclopropylsulfonylcarbamoyl)-2-ethylcyclopropyl)-4-(7-methoxy-2-phenylquinolin-4-yloxy)pyrrolidine-2-carboxamide | *** | 2.03 | 903 |

TABLE I-continued

| Cpd. | STRUCTURE | Name | EC50 | rt | MS + 1 |
|---|---|---|---|---|---|
| 150. | 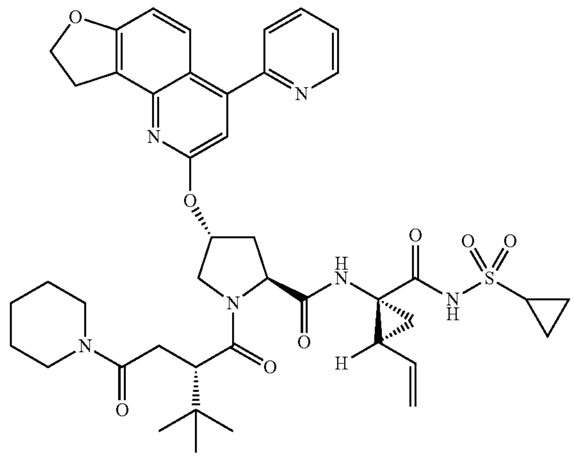 [SMILES: C=C[C@@H]1C[C@]1(NC(=O)[C@@H]1C[C@@H](Oc2cc(-c3ccccn3)c3ccc4c(c3n2)CCO4)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(4-(pyridin-2-yl)-8,9-dihydrofuro[2,3-h]quinolin-2-yloxy)pyrrolidine-2-carboxamide | *** | 2.68 | |
| 151. | 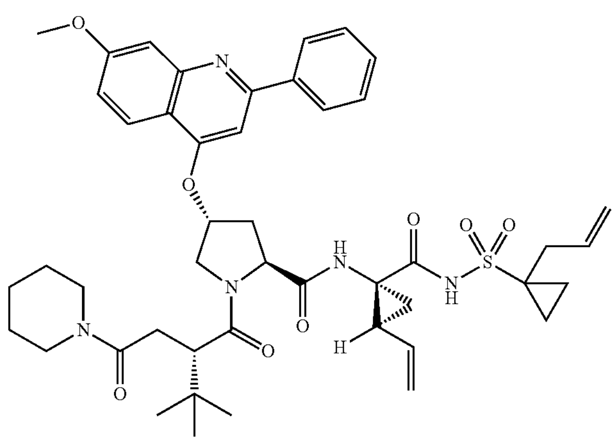 [SMILES: C=CCC1(S(=O)(=O)NC(=O)[C@@]2(NC(=O)[C@@H]3C[C@@H](Oc4cc(-c5ccccc5)nc5cc(OC)ccc45)CN3C(=O)[C@@H](CC(=O)N3CCCCC3)C(C)(C)C)C[C@H]2C=C)CC1] | (2S,4R)-N-(1R,2S)-1-(1-allylcyclopropyl-sulfonylcarbamoyl)-2-vinylcyclopropyl)-1-((S)-2-tert-butyl-4-oxo-4-(piperidin-1-yl)butanoyl)-4-(7-methoxy-2-phenylquinolin-4-yloxy)pyrrolidine-2-carboxamide | *** | 2.31 | 840 |
| 152. | 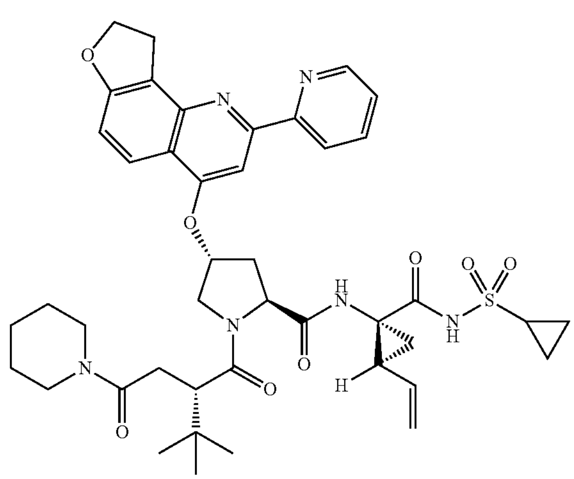 [SMILES: C=C[C@@H]1C[C@]1(NC(=O)[C@@H]1C[C@@H](Oc2cc(-c3ccccn3)nc3c4c(ccc23)OCC4)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(2-(pyridin-2-yl)-8,9-dihydrofuro[2,3-h]quinolin-4-yloxy)pyrrolidine-2-carboxamide | *** | 2.79 | 813.3 |

| Cpd. | STRUCTURE | Name | EC50 | rt | MS + 1 |
|---|---|---|---|---|---|
| 153. | 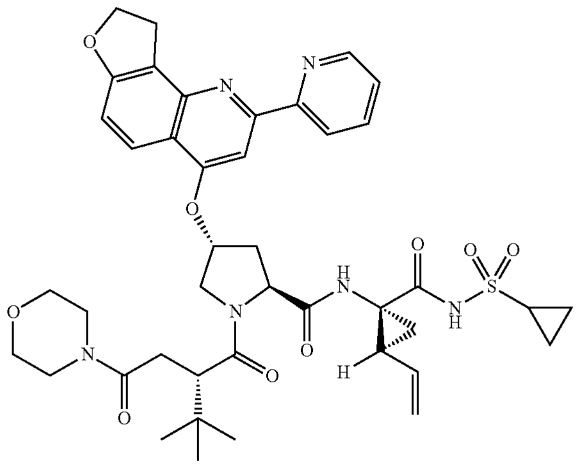 [SMILES: C=C[C@@H]1C[C@]1(NC(=O)[C@@H]1C[C@@H](Oc2cc(-c3ccccn3)nc3c4c(ccc23)OCC4)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-N-((1R,2S)-1-(cyclopropylsulfonylcarbamoyl)-2-vinylcyclopropyl)-4-(2-(pyridin-2-yl)-8,9-dihydrofuro[2,3-h]quinolin-4-yloxy)pyrrolidine-2-carboxamide | *** | 2.49 | 815.3 |
| 154. | 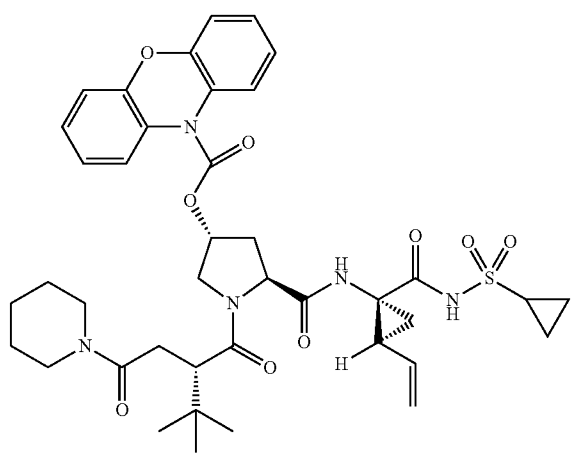 [SMILES: C=C[C@@H]1C[C@]1(NC(=O)[C@@H]1C[C@@H](OC(=O)N2c3ccccc3Oc3ccccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl 10H-phenoxazine-10-carboxylate | ** | 2.84 | 777 |
| 155. | 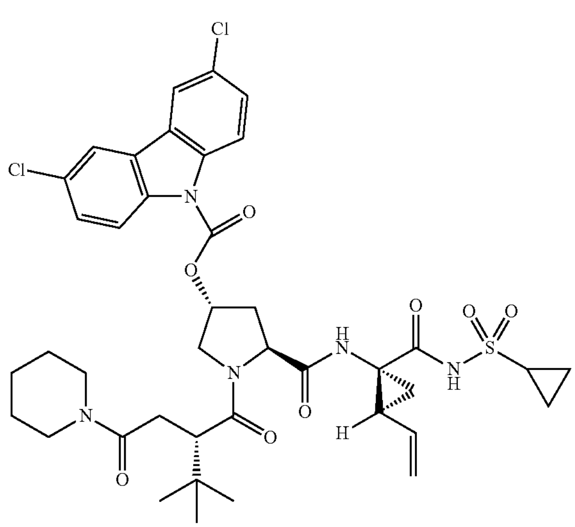 [SMILES: C=C[C@@H]1C[C@]1(NC(=O)[C@@H]1C[C@@H](OC(=O)n2c3ccc(Cl)cc3c3cc(Cl)ccc32)CN1C(=O)[C@@H](CC(=O)N1CCCCC1)C(C)(C)C)C(=O)NS(=O)(=O)C1CC1] | (3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl 3,6-dichloro-9H-carbazole-9-carboxylate | *** | 3.1 | 829 |

| Cpd. | STRUCTURE | Name | EC50 | rt | MS + 1 |
|---|---|---|---|---|---|
| 156. | 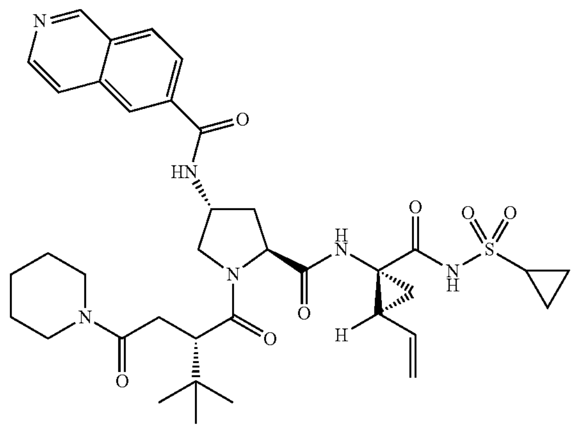 [SMILES: C=C[C@@H]1C[C@]1(NC(=O)[C@@H]1C[C@@H](NC(=O)c2ccc3cnccc3c2)CN1C(=O)[C@@H](CC(=O)N1CCCCC1)C(C)(C)C)C(=O)NS(=O)(=O)C1CC1] | N-((3R,5S)-1-((S)-2-tert-butyl-4-oxo-4-(piperidin-1-yl)butanoyl)-5-((1R,2S)-1-(cyclopropylsulfonylcarbamoyl)-2-vinylcyclopropylcarbamoyl)pyrrolidin-3-yl)isoquinoline-6-carboxamide | | 1.98 | |
| 157. | 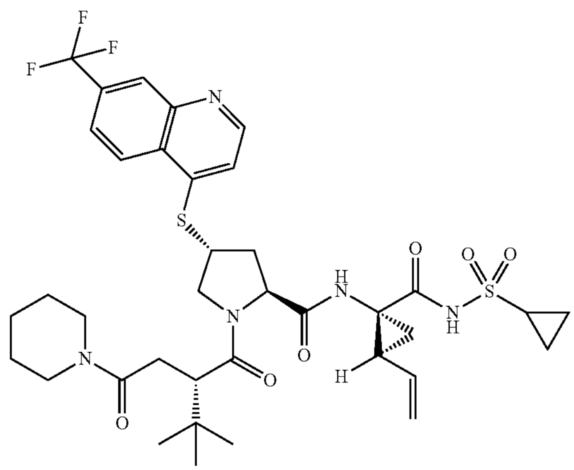 [SMILES: C=C[C@@H]1C[C@]1(NC(=O)[C@@H]1C[C@@H](Sc2ccnc3cc(C(F)(F)F)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-(trifluoromethyl)quinolin-4-ylthio)pyrrolidine-2-carboxamide | | 2.59 | |
| 158. | 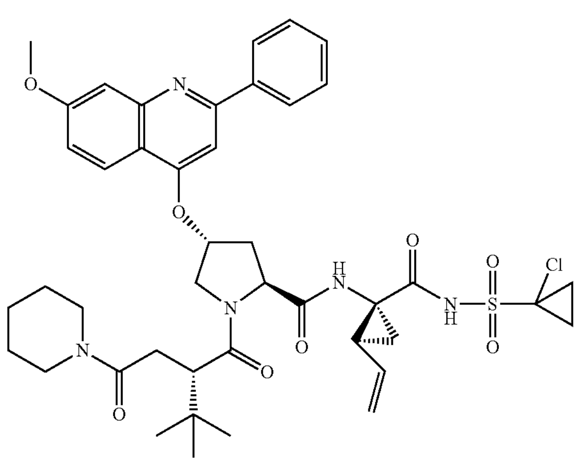 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1(Cl)CC1] | (2S,4R)-1-((S)-2-tert-butyl-4-oxo-4-(piperidin-1-yl)butanoyl)-N-((1R,2S)-1-(1-chlorocyclopropylsulfonylcarbamoyl)-2-vinylcyclopropyl)-4-(7-methoxy-2-phenylquinolin-4-yloxy)pyrrolidine-2-carboxamide | *** | 2.44 | 834 |

TABLE I-continued

| Cpd. | STRUCTURE | Name | EC50 | rt | MS + 1 |
|---|---|---|---|---|---|
| 159. | 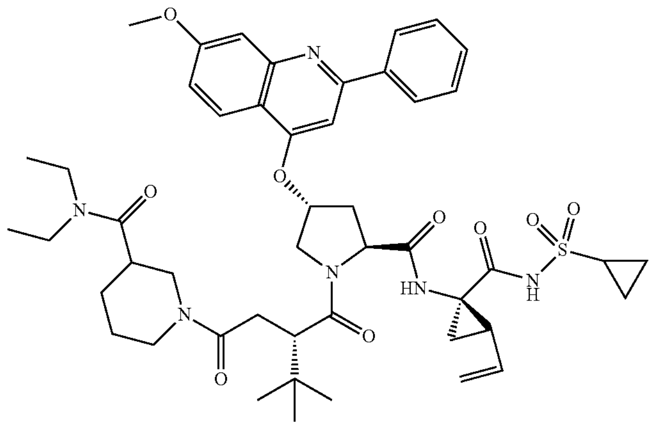 | 1-((S)-3-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoyl)-N,N-diethylpiperidine-3-carboxamide | *** | 1.57 | 900 |
| 160. | 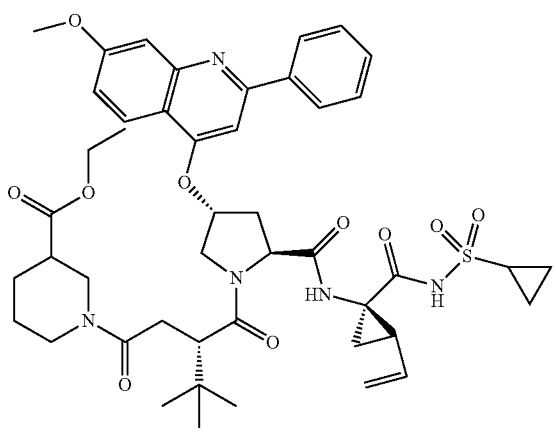 | ethyl 1-((S)-3-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoyl)piperidine-3-carboxylate | *** | 1.62 | 873 |
| 161. | 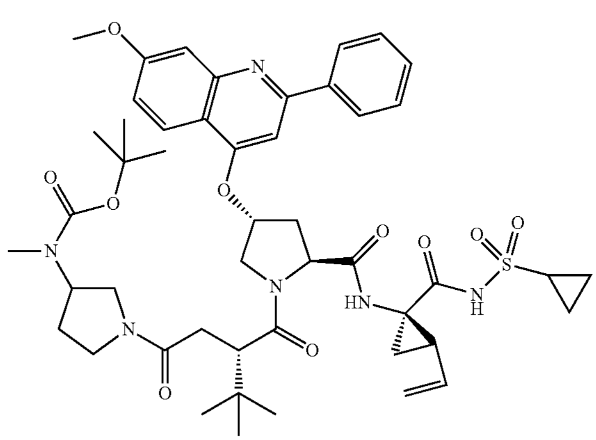 | tert-butyl 1-((S)-3-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoyl)pyrrolidin-3-yl(methyl)carbamate | *** | 1.68 | 916 |

TABLE I-continued

| Cpd. | STRUCTURE | Name | EC50 | rt | MS + 1 |
|---|---|---|---|---|---|
| 162. | 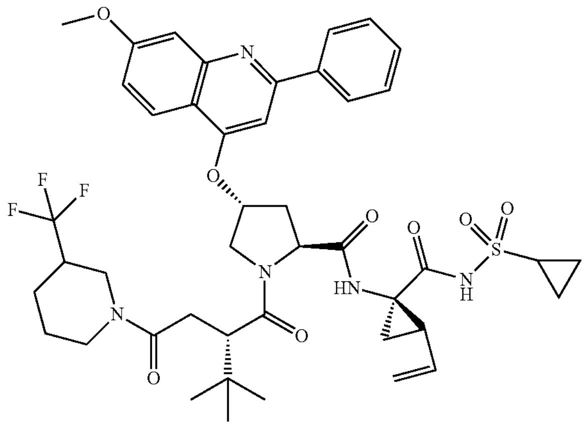 | (2S,4R)-1-((2S)-2-tert-butyl-4-oxo-4-(3-(trifluoromethyl)piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.66 | 869 |
| 163. | 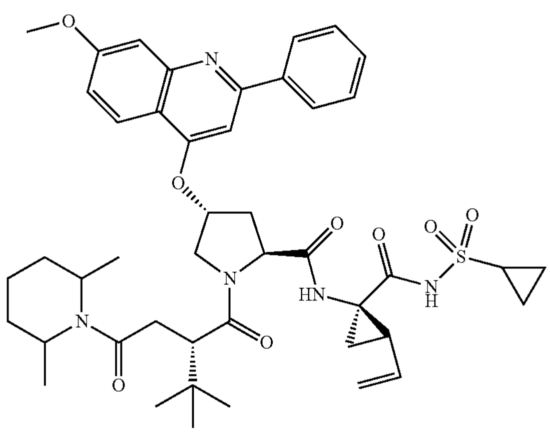 | (2S,4R)-1-((2S)-2-tert-butyl-4-(2,6-dimethylpiperidin-1-yl)-4-oxobutanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide | *** | 1.69 | 829 |
| 164. | 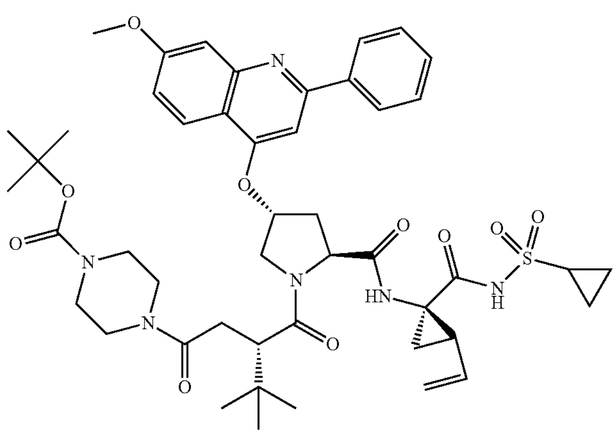 | tert-butyl 4-((S)-3-((2S,4R)-2-((1R,2S)-1-(cyclopropylsulfonylcarbamoyl)-2-vinylcyclopropylcarbamoyl)-4-(7-methoxy-2-phenylquinolin-4-yloxy)pyrrolidine-1-carbonyl)-4,4-dimethylpentanoyl)piperazine-1-carboxylate | *** | 1.62 | 902 |

TABLE I-continued

| Cpd. | STRUCTURE | Name | EC50 | rt | MS + 1 |
|---|---|---|---|---|---|
| 165. | 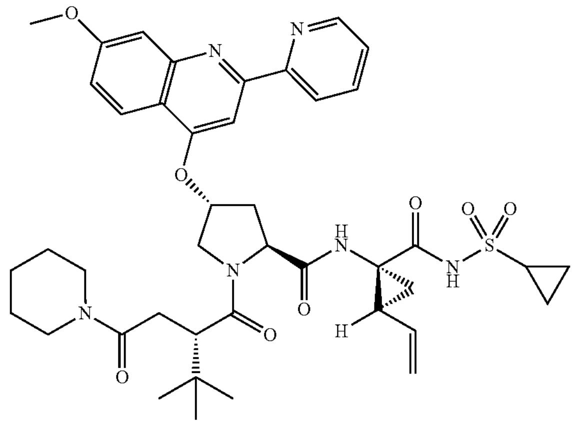 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R,2S)-1-(cyclopropylsulfonyl-carbamoyl)-2-vinyl-cyclopropyl)-4-(7-methoxy-2-(pyridin-2-yl)quinolin-4-yloxy)pyrrolidine-2-carboxamide | *** | 3.16 | 801.5 |
| 166. | 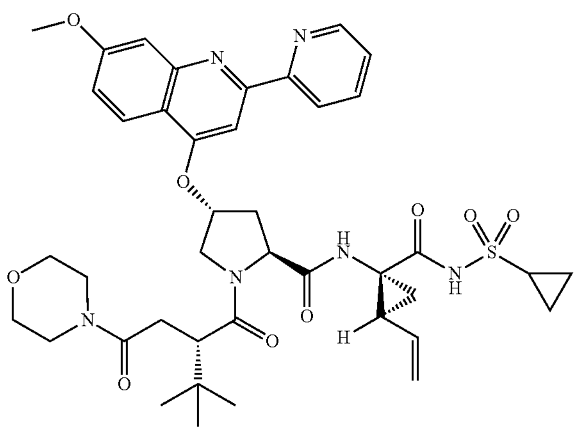 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-N-((1R,2S)-1-(cyclopropylsulfonyl-carbamoyl)-2-vinylcyclopropyl)-4-(7-methoxy-2-(pyridin-2-yl)quinolin-4-yloxy)pyrrolidine-2-carboxamide | *** | 3.19 | 803.5 |
| 167. | 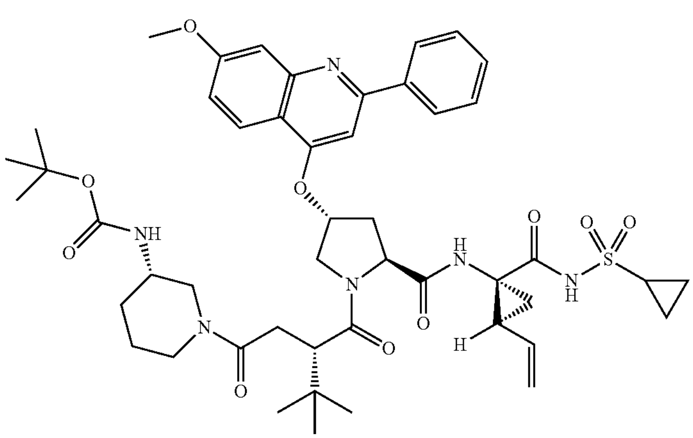 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC[C@H](NC(=O)OC(C)(C)C)C1)C(C)(C)C)C(=O)NS(=O)(=O)C1CC1] | tert-butyl (S)-1-((S)-3-((2S,4R)-2-((1R,2S)-1-(cyclopropylsulfonyl-carbamoyl)-2-vinylcyclopropyl-carbamoyl)-4-(7-methoxy-2-phenylquinolin-4-yloxy(pyrrolidine-1-carbonyl)-4,4-dimethylpentanoyl)piperidin-3-ylcarbamate | *** | 1.68 | 916 |

TABLE I-continued

| Cpd. | STRUCTURE | Name | EC50 | rt | MS + 1 |
|---|---|---|---|---|---|
| 168. | 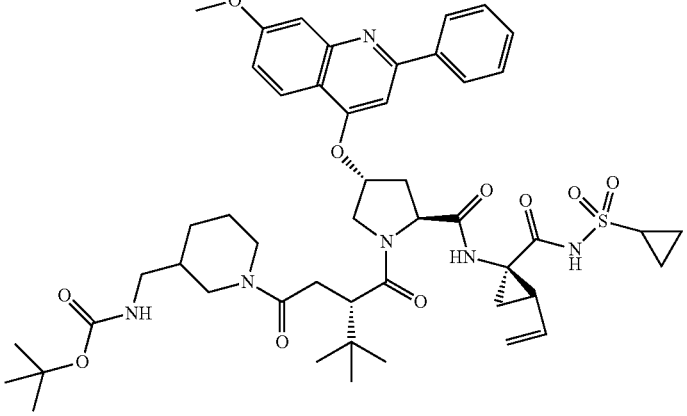 | tert-butyl (1-((S)-3-((2S,4R)-2-((1R,2S)-1-(cyclopropyl-sulfonylcarbamoyl)-2-vinylcyclopropyl-carbamoyl)-4-(7-methoxy-2-phenylquinolin-4-yloxy)pyrrolidine-1-carbonyl)-4,4-dime-thylpentanoyl)piper-idin-3-yl)methylcarbamate | *** | 1.81 | 930 |
| 169. | 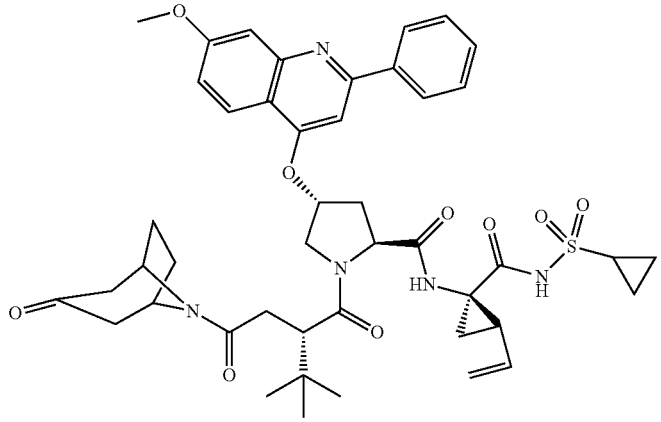 | (2S,4R)-1-((2S)-2-tert-butyl-4-oxo-4-(3-oxo-8-aza-bicyclo[3.2.1]octan-8-yl)butanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 1.4 | 841 |
| 170. | 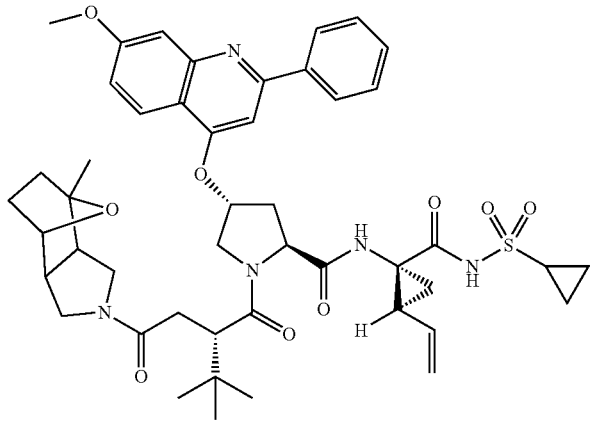 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC2C3CCC(C)(O3)C2C1)C(C)(C)C)C(=O)NS(=O)(=O)C1CC1] | | *** | 1.61 | 869 |

| Cpd. | STRUCTURE | Name | EC50 | rt | MS + 1 |
|---|---|---|---|---|---|
| 171. | 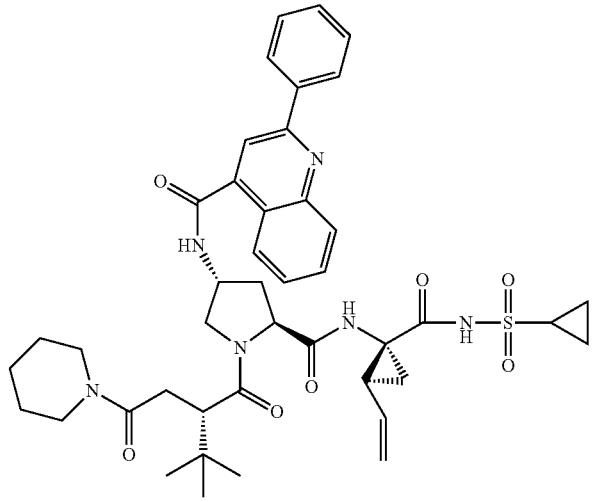 [SMILES: C=C[C@@H]1C[C@]1(NC(=O)[C@@H]1C[C@@H](NC(=O)c2cc(-c3ccccc3)nc3ccccc23)CN1C(=O)[C@@H](CC(=O)N1CCCCC1)C(C)(C)C)C(=O)NS(=O)(=O)C1CC1] | N-((3R,5S)-1-((S)-2-tert-butyl-4-oxo-4-(piperidin-1-yl)butanoyl)-5-((1R,2S)-1-(cyclopropyl-sulfonylcarbamoyl)-2-vinylcyclo-propylcarbamo-yl)pyrrolidin-3-yl)-2-phenylquinoline-4-carboxamide | *** | 1.96 | |
| 172. | 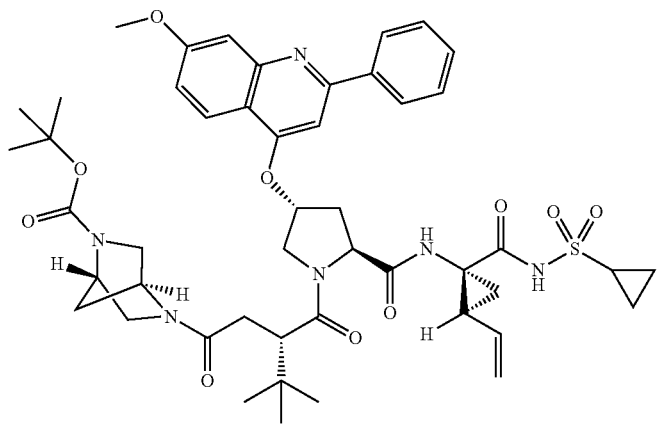 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1C[C@@H]2C[C@H]1CN2C(=O)OC(C)(C)C)C(C)(C)C)C(=O)NS(=O)(=O)C1CC1] | (1S,4S)-tert-butyl 5-((S)-3-((2S,4R)-2-((1R,2S)-1-(cyclopropyl-sulfonylcarbamoyl)-2-vinylcyclopropyl-carbamoyl)-4-(7-methoxy-2-phenylquinolin-4-yloxy)pyrrolidine-1-carbonyl)-4,4-dimethylpentanoyl)-2,5-diazabi-cyclo[2.2.1]heptane-2-carboxylate | *** | 1.7 | 914 |
| 173. | 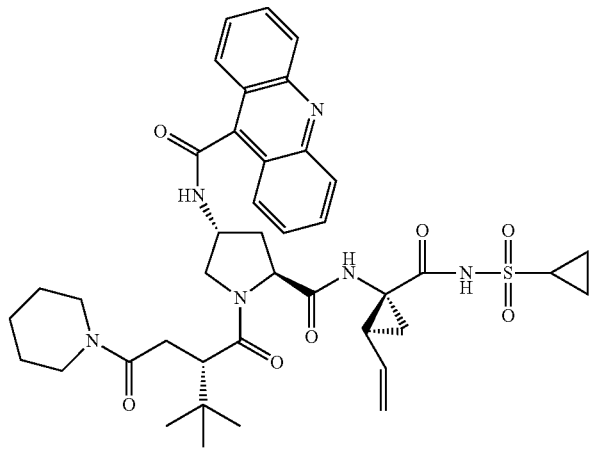 [SMILES: C=C[C@@H]1C[C@]1(NC(=O)[C@@H]1C[C@@H](NC(=O)c2c3ccccc3nc3ccccc23)CN1C(=O)[C@@H](CC(=O)N1CCCCC1)C(C)(C)C)C(=O)NS(=O)(=O)C1CC1] | N-((3R,5S)-1-((S)-2-tert-butyl-4-oxo-4-(piperidin-1-yl)butanoyl)-5-((1R,2S)-1-(cyclopropyl-sulfonylcarbamoyl)-2-vinylcyclopropyl-carbamoyl)pyr-rolidin-3-yl)acridine-9-carboxamide | | 1.49 | |

| Cpd. | STRUCTURE | Name | EC50 | rt | MS + 1 |
|---|---|---|---|---|---|
| 174. | 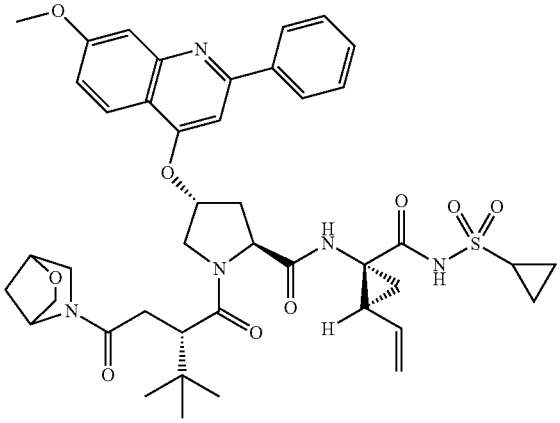 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC2CC1CO2)C(C)(C)C)C(=O)NS(=O)(=O)C1CC1] | (2S,4R)-1-((2S)-2-(2-(2-oxa-5-aza-bicyclo[2.2.1]heptan-5-yl)-2-oxoethyl)-3,3-dimethylbutanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 1.44 | 815 |
| 175. | 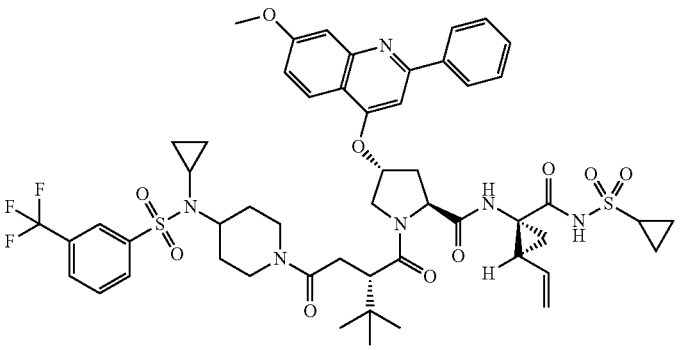 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(N(C2CC2)S(=O)(=O)c2cccc(C(F)(F)F)c2)CC1)C(C)(C)C)C(=O)NS(=O)(=O)C1CC1] | (2S,4R)-1-((S)-2-tert-butyl-4-(4-(N-cyclopropyl-3-(tri-fluoromethyl)phenyl-sulfonamido)piper-idin-1-yl)-4-oxobutanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | 1.91 | 1064 |
| 176. | 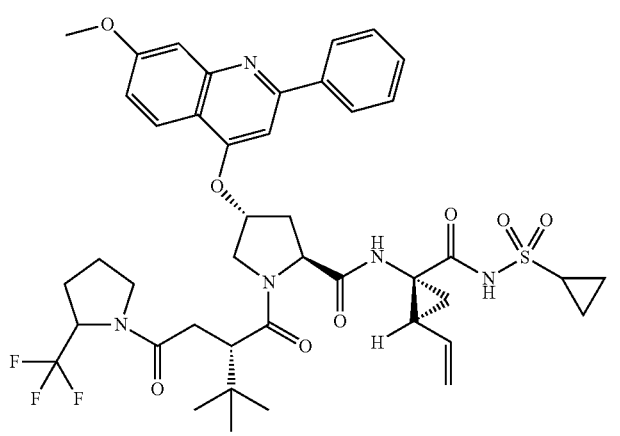 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCC1C(F)(F)F)C(C)(C)C)C(=O)NS(=O)(=O)C1CC1] | (2S,4R)-1-((2S)-2-tert-butyl-4-oxo-4-(2-(trifluoro-methyl)pyrrolidin-1-yl)butanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.71 | 855 |

TABLE I-continued

| Cpd. | STRUCTURE | Name | EC50 | rt | MS + 1 |
|---|---|---|---|---|---|
| 177. | 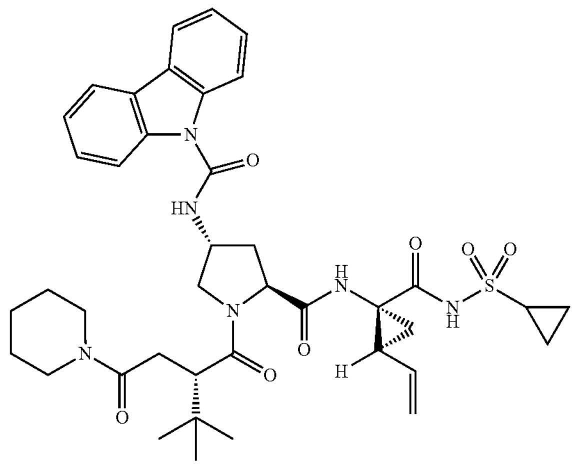 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCCCC1)C(C)(C)C)C(=O)NS(=O)(=O)C1CC1] | N-((3R,5S)-1-((S)-2-tert-butyl-4-oxo-4-(piperidin-1-yl)butanoyl)-5-((1R,2S)-1-(cyclopropyl-sulfonylcarbamoyl)-2-vinylcyclopropyl-carbamoyl)pyr-rolidin-3-yl)-9H-carbazole-9-carboxamide | *** | 2.79 | 760 |
| 178. | 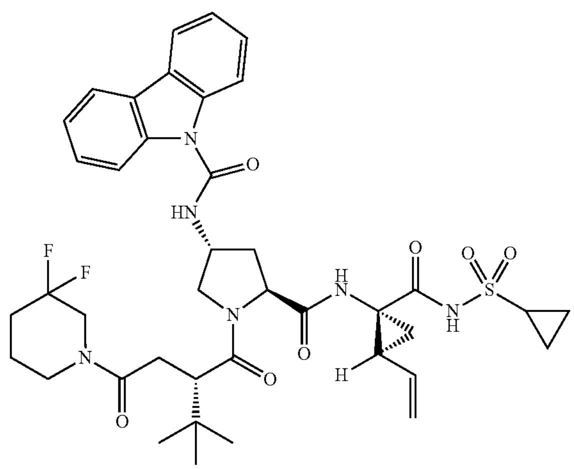 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCCC(F)(F)C1)C(C)(C)C)C(=O)NS(=O)(=O)C1CC1] | N-((3R,5S)-1-((S)-2-tert-butyl-4-(3,3-difluoropiperidin-1-yl)-4-oxobutanoyl)-5-((1R,2S)-1-(cyclo-propylsulfonyl-carbamoyl)-2-vinylcyclopropyl-carbamoyl)pyrrolidin-3-yl)-9H-carbazole-9-carboxamide | *** | 2.62 | 796 |
| 179. | 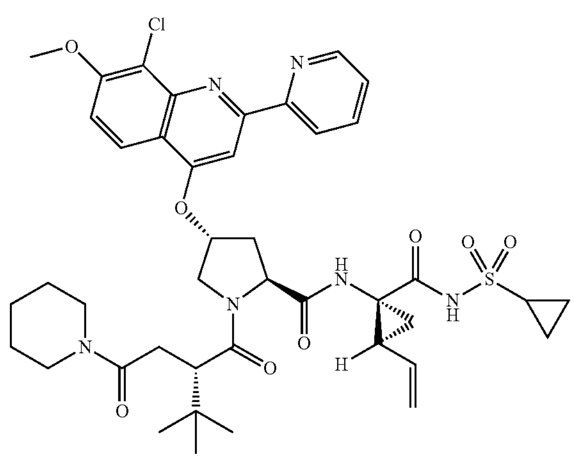 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-4-(8-chloro-7-methoxy-2-(pyridin-2-yl)quinolin-4-yloxy)-N-((1R,2S)-1-(cyclopropyl-sulfonylcarbamoyl)-2-vinylcyclo-propyl)pyrrolidine-2-carboxamide | *** | 1.83 | 835 |

| Cpd. | STRUCTURE | Name | EC50 | rt | MS + 1 |
|---|---|---|---|---|---|
| 180. | 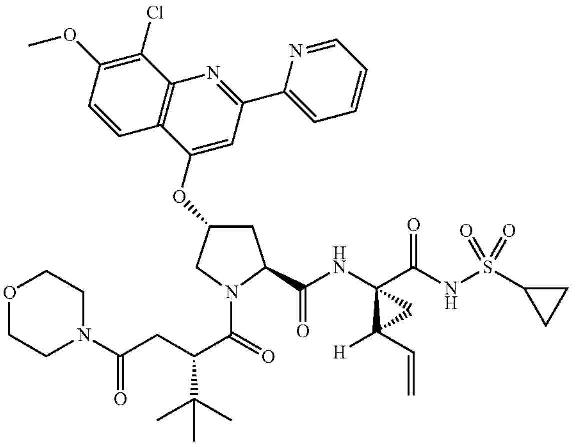 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCOCC1)C(C)(C)C)C(=O)NS(=O)(=O)C1CC1] | (2S,4R)-1-((S)-2-tert-butyl-4-morpholino-4-oxobutanoyl)-4-(8-chloro-7-methoxy-2-(pyridin-2-yl)quinolin-4-yloxy)-N-((1R,2S)-1-(cyclopropyl-sulfonylcarbamoyl)-2-vinyl-cyclopropyl)pyr-rolidine-2-carboxamide | *** | 1.58 | 838 |
| 181. | 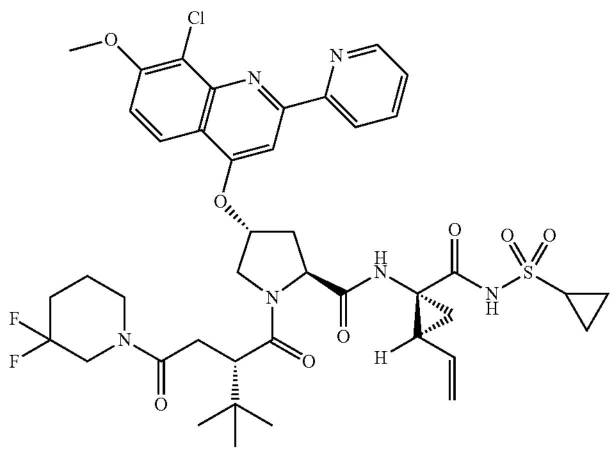 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-4-(8-chloro-7-methoxy-2-(pyridin-2-yl)quinolin-4-yloxy)-N-((1R,2S)-1-(cyclopropyl-sulfonylcarbamoyl)-2-vinyl-cyclopropyl)pyr-rolidine-2-carboxamide | *** | 1.82 | 872 |
| 182. | 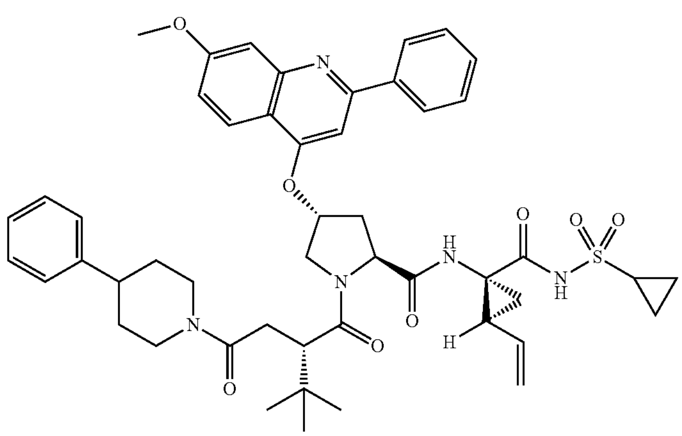 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC(c2ccccc2)CC1)C(C)(C)C)C(=O)NS(=O)(=O)C1CC1] | (2S,4R)-1-((S)-2-tert-butyl-4-oxo-4-(4-phenylpiperidin-1-yl)butanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.86 | 877 |

TABLE I-continued

| Cpd. | STRUCTURE | Name | EC50 | rt | MS + 1 |
|---|---|---|---|---|---|
| 183. | 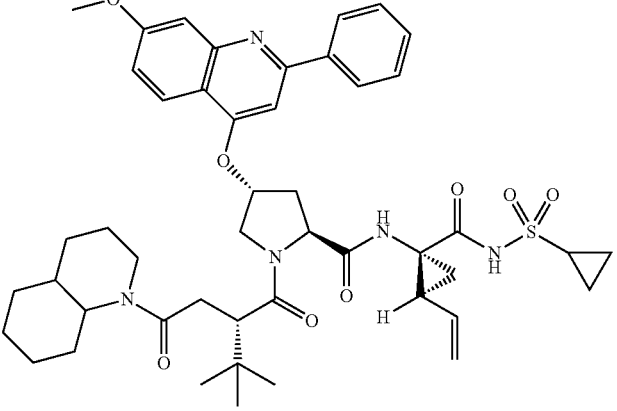 | (2S,4R)-1-((2S)-2-tert-butyl-4-(octahydroquinolin-1(2H)-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.85 | 855 |
| 184. | 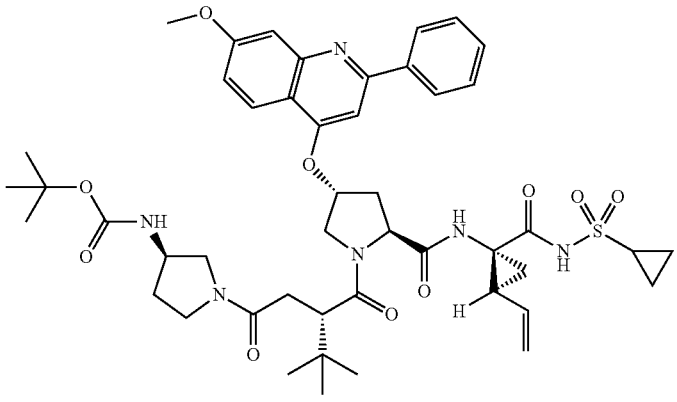 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC[C@@H](NC(=O)OC(C)(C)C)C1)C(C)(C)C)C(=O)NS(=O)(=O)C1CC1] | tert-butyl (R)-1-((S)-3-((2S,4R)-2-((1R,2S)-1-(cyclopropylsulfonyl-carbamoyl)-2-vinyl-cyclopropyl-carbamoyl)-4-(7-methoxy-2-phenylquinolin-4-yloxy)pyrrolidine-1-carbonyl)-4,4-dimethylpentanoyl)pyrrolidin-3-ylcarbamate | *** | 1.73 | 902 |
| 185. | 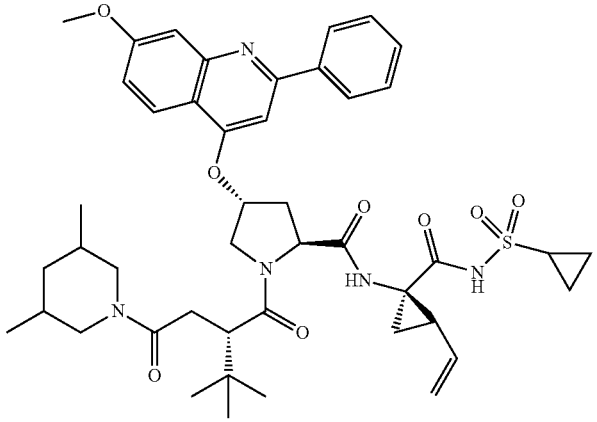 | (2S,4R)-1-((2S)-2-tert-butyl-4-(3,5-dimethylpiperidin-1-yl)-4-oxobutanoyl)-N-((1R,2S)-1-(cyclopropylsulfonyl-carbamoyl)-2-vinylcyclopropyl)-4-(7-methoxy-2-phenylquinolin-4-yloxy)pyrrolidine-2-carboxamide | *** | 1.91 | 829 |

TABLE I-continued

| Cpd. | STRUCTURE | Name | EC50 | rt | MS + 1 |
|---|---|---|---|---|---|
| 186. | 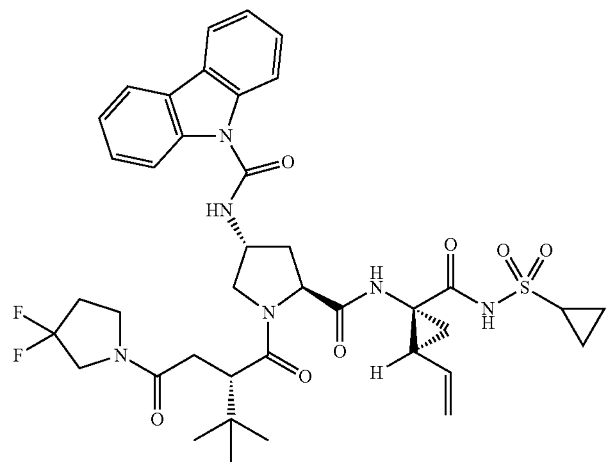 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCC(F)(F)C1)C(C)(C)C)C(=O)NS(=O)(=O)C1CC1] | N-((3R,5S)-1-((S)-2-tert-butyl-4-(3,3-difluoropyrrolidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-9H-carbazole-9-carboxamide | *** | 2.16 | 782 |
| 187. | 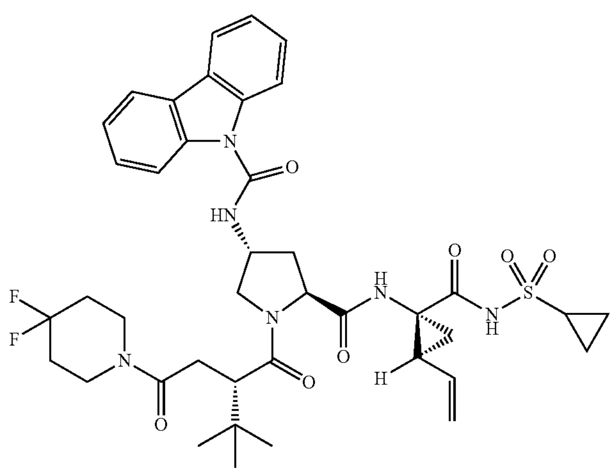 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCC(F)(F)CC1)C(C)(C)C)C(=O)NS(=O)(=O)C1CC1] | N-((3R,5S)-1-((S)-2-tert-butyl-4-(4,4-difluoropiperidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-9H-carbazole-9-carboxamide | *** | 2.28 | 796 |
| 188. | 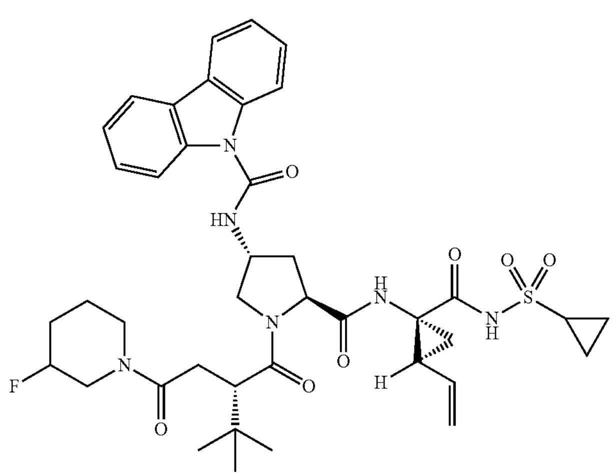 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCCC(F)C1)C(C)(C)C)C(=O)NS(=O)(=O)C1CC1] | N-((3R,5S)-1-((2S)-2-tert-butyl-4-(3-fluoropiperidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-9H-carbazole-9-carboxamide | *** | 2.26 | 778 |

TABLE I-continued

| Cpd. | STRUCTURE | Name | EC50 | rt | MS + 1 |
|---|---|---|---|---|---|
| 189. | 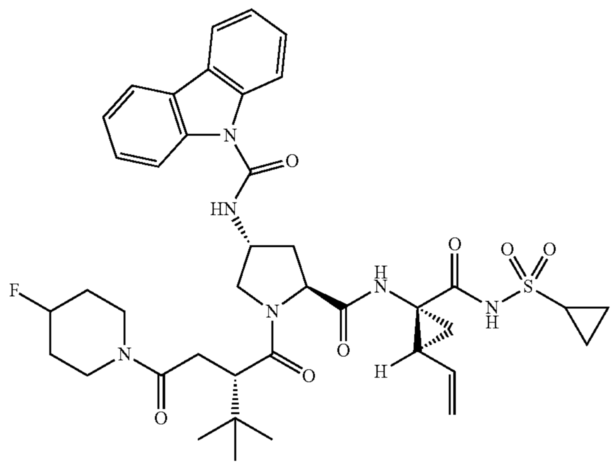 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCC(F)CC1)C(C)(C)C)C(=O)NS(=O)(=O)C1CC1] | N-((3R,5S)-1-((S)-2-tert-butyl-4-(4-fluoropiperidin-1-yl)-4-oxobutanoyl)-5-((1R,2S)-1-(cyclopropylsulfonyl-carbamoyl)-2-vinylcyclopropyl-carbamoyl)pyrrolidin-3-yl)-9H-carbazole-9-carboxamide | *** | 2.16 | 778 |
| 190. | 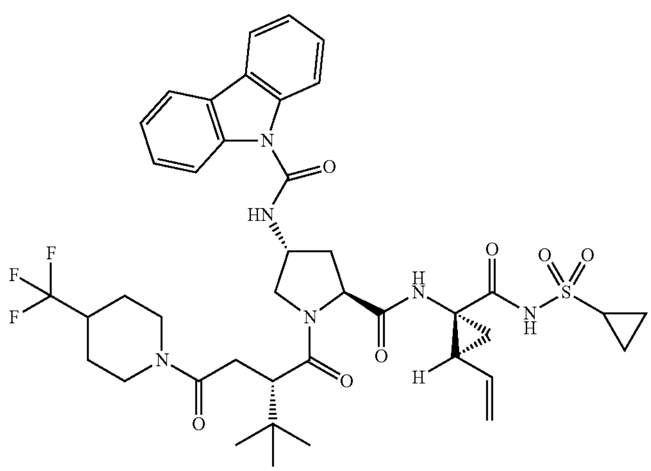 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CCC(C(F)(F)F)CC1)C(C)(C)C)C(=O)NS(=O)(=O)C1CC1] | N-((3R,5S)-1-((S)-2-tert-butyl-4-oxo-4-(4-(trifluoromethyl)piperidin-1-yl)butanoyl)-5-((1R,2S)-1-(cyclopropylsulfonyl-carbamoyl)-2-vinylcyclopropyl-carbamoyl)pyrrolidin-3-yl)-9H-carbazole-9-carboxamide | *** | 2.36 | 828 |
| 191. | 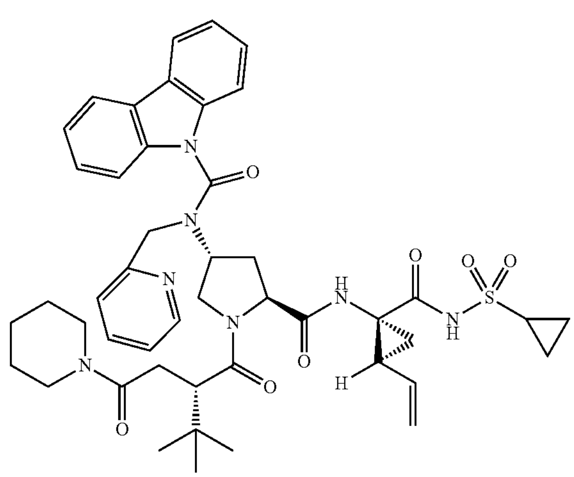 [SMILES: C=C[C@@H]1C[C@]1(NC(=O)[C@@H]1C[C@@H](N(Cc2ccccn2)C(=O)n2c3ccccc3c3ccccc32)CN1C(=O)[C@@H](CC(=O)N1CCCCC1)C(C)(C)C)C(=O)NS(=O)(=O)C1CC1] | N-((3R,5S)-1-((S)-2-tert-butyl-4-oxo-4-(piperidin-1-yl)butanoyl)-5-((1R)-1-(cyclopropylsulfonyl-carbamoyl)-2-vinyl-cyclopropyl-carbamoyl)pyrrolidin-3-yl)-N-(pyridin-2-ylmethyl)-9H-carbazole-9-carboxamide | *** | | |

| Cpd. | STRUCTURE | Name | EC50 | rt | MS + 1 |
|---|---|---|---|---|---|
| 192. | 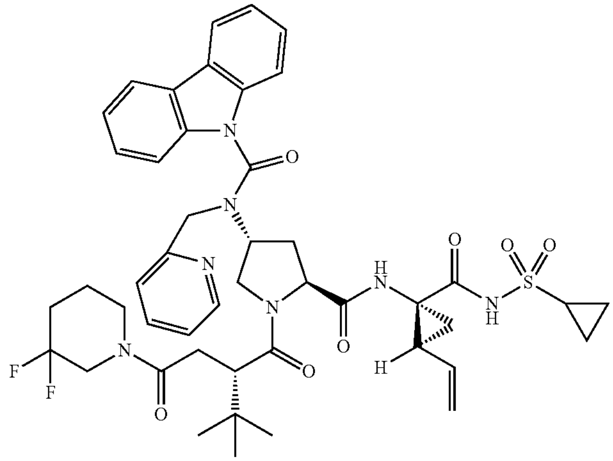 [SMILES: C=C[C@@H]1C[C@]1(NC(=O)[C@@H]1C[C@@H](N(Cc2ccccn2)C(=O)n2c3ccccc3c3ccccc32)CN1C(=O)[C@@H](CC(=O)N1CCCC(F)(F)C1)C(C)(C)C)C(=O)NS(=O)(=O)C1CC1] | N-((3R,5S)-1-((S)-2-tert-butyl-4-(3,3-difluoropiperidin-1-yl)-4-oxobutanoyl)-5-((1R)-1-(cyclopropylsulfonyl-carbamoyl)-2-vinylcyclopropyl-carbamoyl)pyrrolidin-3-yl)-N-(pyridin-2-ylmethyl)-9H-carbazole-9-carboxamide | *** | | |
| 193. | 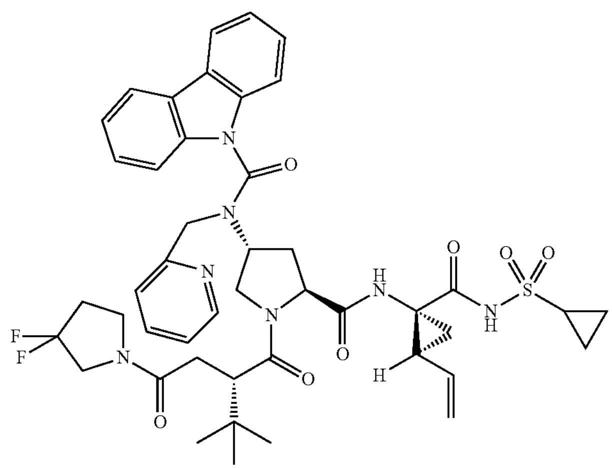 [SMILES: C=C[C@@H]1C[C@]1(NC(=O)[C@@H]1C[C@@H](N(Cc2ccccn2)C(=O)n2c3ccccc3c3ccccc32)CN1C(=O)[C@@H](CC(=O)N1CCC(F)(F)C1)C(C)(C)C)C(=O)NS(=O)(=O)C1CC1] | N-((3R,5S)-1-((S)-2-tert-butyl-4-(3,3-difluoropyrrolidin-1-yl)-4-oxobutanoyl)-5-((1R)-1-(cyclopropylsulfonyl-carbamoyl)-2-vinylcyclopropyl-carbamoyl)pyrrolidin-3-yl)-N-(pyridin-2-ylmethyl)-9H-carbazole-9-carboxamide | *** | | |
| 194. | 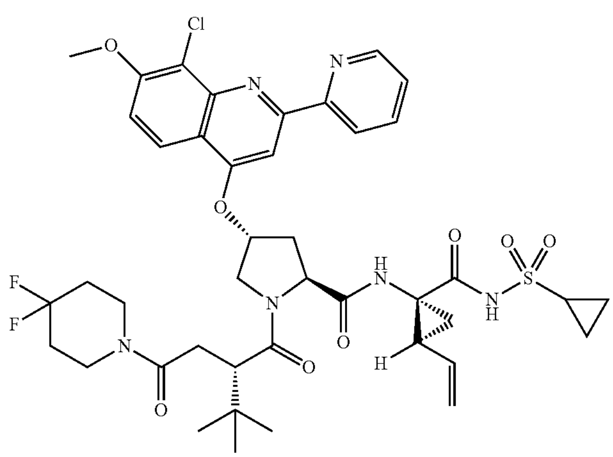 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCC(F)(F)CC1)C(C)(C)C)C(=O)NS(=O)(=O)C1CC1] | (2S,4R)-1-((S)-2-tert-butyl-4-(4,4-difluoropiperidin-1-yl)-4-oxobutanoyl)-4-(8-chloro-7-methoxy-2-(pyridin-2-yl)quinolin-4-yloxy)-N-((1R)-1-(cyclopropyl-sulfonylcarbamoyl)-2-vinyl-cyclopropyl)pyr-rolidine-2-carboxamide | *** | | |

TABLE I-continued

| Cpd. | STRUCTURE | Name | EC50 | rt | MS + 1 |
|---|---|---|---|---|---|
| 195. | 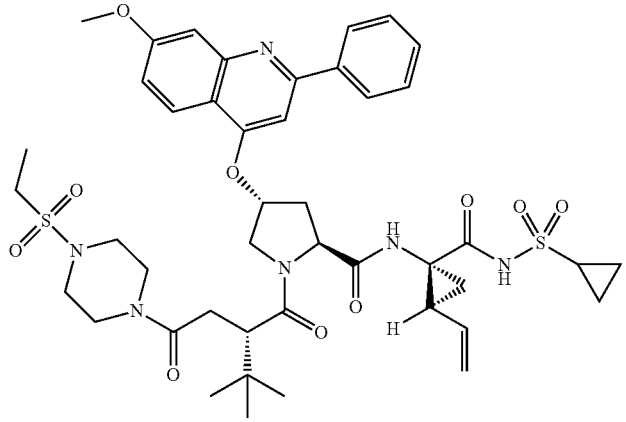 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCN(S(=O)(=O)CC)CC1)C(C)(C)C)C(=O)NS(=O)(=O)C1CC1] | (2S,4R)-1-((S)-2-tert-butyl-4-(4-(ethylsulfonyl)piper-azin-1-yl)-4-oxobutanoyl)-N-((1R)-1-(cyclopropylsulfonyl-carbamoyl)-2-vinylcyclopropyl)-4-(7-methoxy-2-phenylquinolin-4-yloxy)pyrrolidine-2-carboxamide | *** | | |
| 196. | 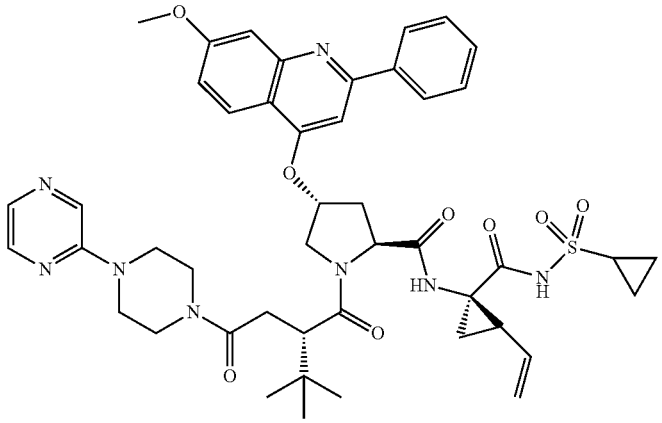 | (2S,4R)-1-((S)-2-tert-butyl-4-oxo-4-(4-(pyrazin-2-yl)piperazin-1-yl)butanoyl)-N-((1R,2S)-1-(cyclopropyl-sulfonylcarbamoyl)-2-vinylcyclopropyl)-4-(7-methoxy-2-phenylquinolin-4-yloxy)pyrrolidine-2-carboxamide | *** | | |
| 197. | 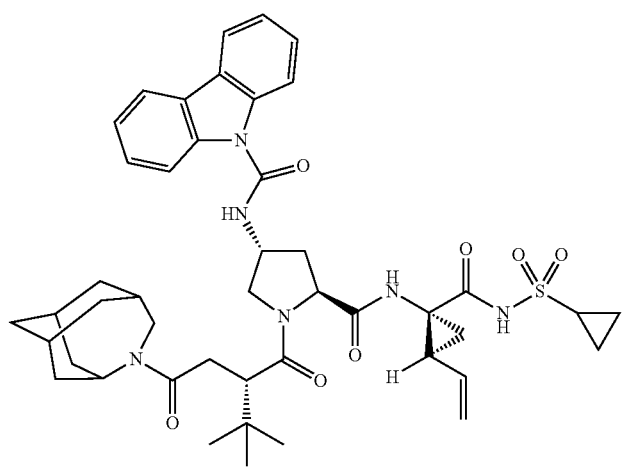 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CC2CC3CC(C2)CC1C3)C(C)(C)C)C(=O)NS(=O)(=O)C1CC1] | | *** | | |

TABLE I-continued

| Cpd. | STRUCTURE | Name | EC50 | rt | MS + 1 |
|---|---|---|---|---|---|
| 198. | 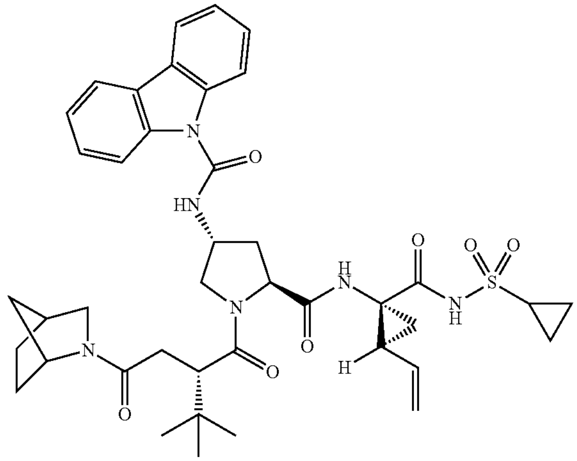 [SMILES: C=C[C@@H]1C[C@]1(NC(=O)[C@@H]1C[C@@H](NC(=O)n2c3ccccc3c3ccccc32)CN1C(=O)[C@@H](CC(=O)N1CC2CCC1C2)C(C)(C)C)C(=O)NS(=O)(=O)C1CC1] | N-((3R,5S)-1-((2S)-2-(2-(2-aza-bicyclo[2.2.1]heptan-2-yl)-2-oxoethyl)-3,3-dimethylbutanoyl)-5-((1R)-1-(cyclopropylsulfonyl-carbamoyl)-2-vinylcyclopropyl-carbamoyl)pyrrolidin-3-yl)-9H-carbazole-9-carboxamide | *** | | |
| 199. | 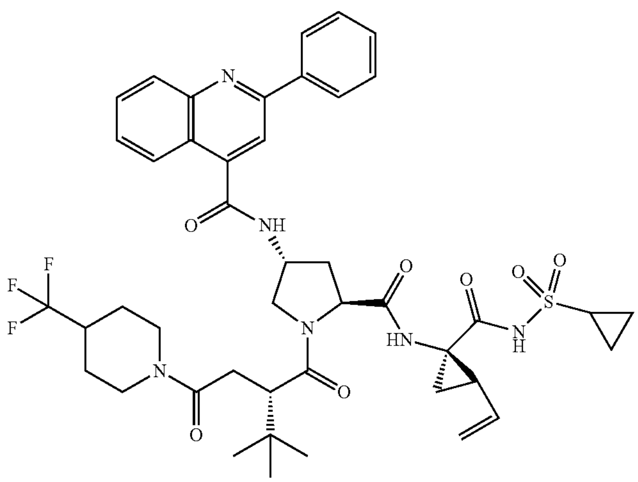 | N-((3R,5S)-1-((S)-2-tert-butyl-4-oxo-4-(4-(trifluoromethyl)piper-idin-1-yl)butanoyl)-5-((1R,2S)-1-(cyclo-propylsulfonyl-carbamoyl)-2-vinyl-cyclopropyl-carbamoyl)pyrrolidin-3-yl)-2-phenylquinoline-4-carboxamide | *** | | |
| 200. | 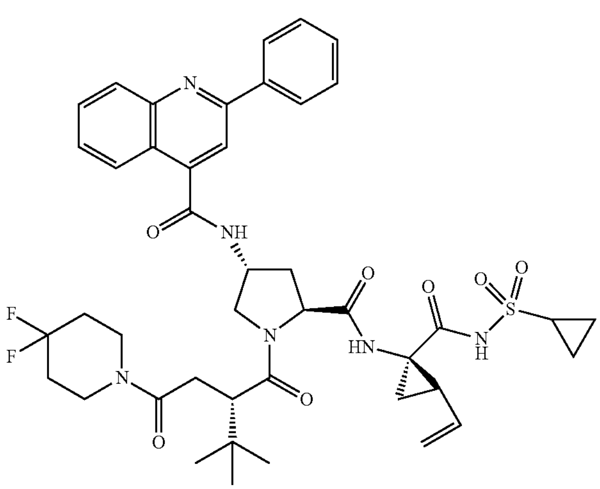 | N-((3R,5S)-1-((S)-2-tert-butyl-4-(4,4-difluoropiperidin-1-yl)-4-oxobutanoyl)-5-((1R,2S)-1-(cyclopropylsulfonyl-carbamoyl)-2-vinylcyclopropyl-carbamoyl)pyrrolidin-3-yl)-2-phenylquinoline-4-carboxamide | *** | | |

| Cpd. | STRUCTURE | Name | EC50 | rt | MS + 1 |
|---|---|---|---|---|---|
| 201. | 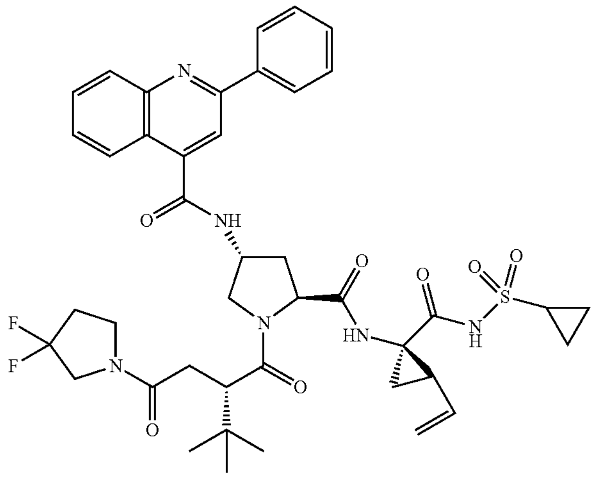 | N-((3R,5S)-1-((S)-2-tert-butyl-4-(3,3-difluoropyrrolidin-1-yl)-4-oxobutanoyl)-5-((1R,2S)-1-(cyclopropylsulfonyl-carbamoyl)-2-vinylcyclopropyl-carbamoyl)pyrrolidin-3-yl)-2-phenylquinoline-4-carboxamide | *** | | |
| 202. | 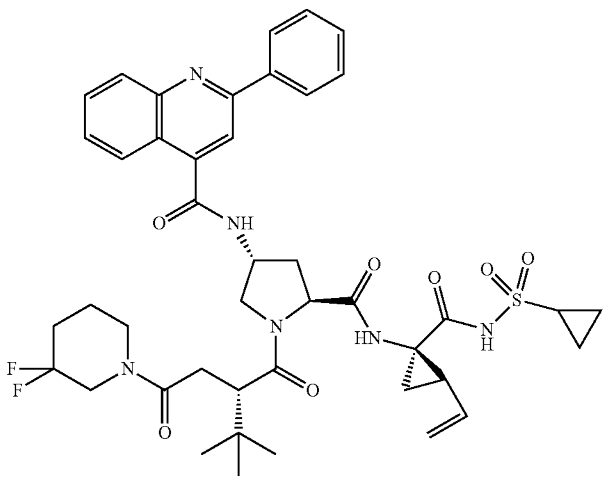 | N-((3R,5S)-1-((S)-2-tert-butyl-4-(3,3-difluoropiperidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-2-phenylquinoline-4-carboxamide | *** | | |
| 203. | 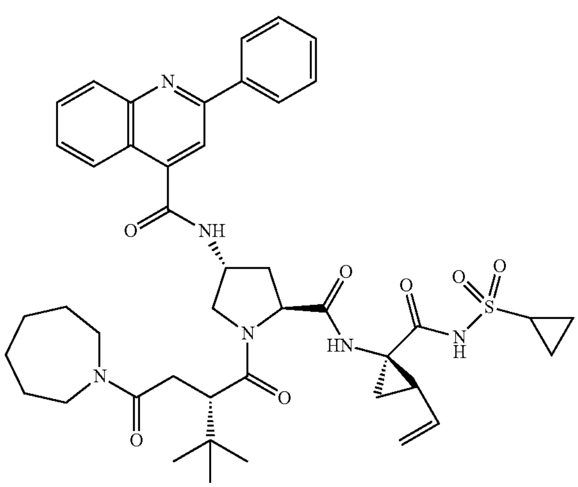 | N-((3R,5S)-1-((S)-4-(azepan-1-yl)-2-tert-butyl-4-oxobutanoyl)-5-((1R,2S)-1-(cyclopropylsulfonyl-carbamoyl)-2-vinylcyclopropyl-carbamoyl)pyrrolidin-3-yl)-2-phenylquinoline-4-carboxamide | *** | | |

TABLE I-continued

| Cpd. | STRUCTURE | Name | EC50 | rt | MS + 1 |
|---|---|---|---|---|---|
| 204. | 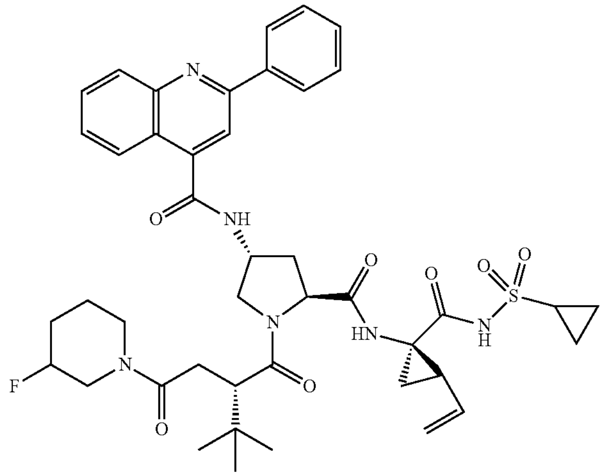 | N-((3R,5S)-1-((2S)-2-tert-butyl-4-(3-fluoropiperidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-2-phenylquinoline-4-carboxamide | *** | | |
| 205. | 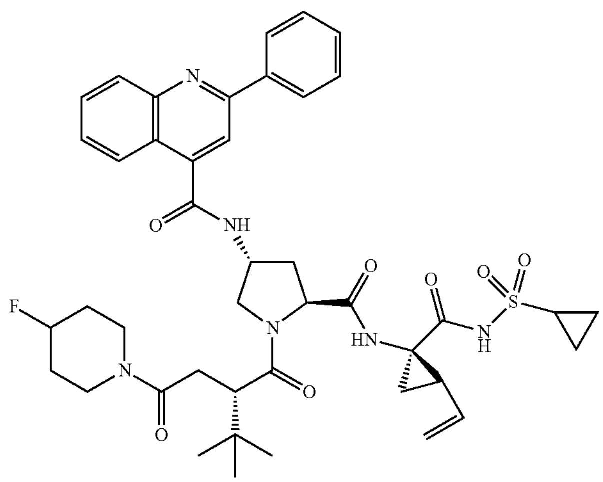 | N-((3R,5S)-1-((S)-2-tert-butyl-4-(4-fluoropiperidin-1-yl)-4-oxobutanoyl)-5-((1R,2S)-1-(cyclopropylsulfonyl-carbamoyl)-2-vinyl-cyclopropyl-carbamoyl)pyrrolidin-3-yl)-2-phenylquinoline-4-carboxamide | *** | | |
| 206. | 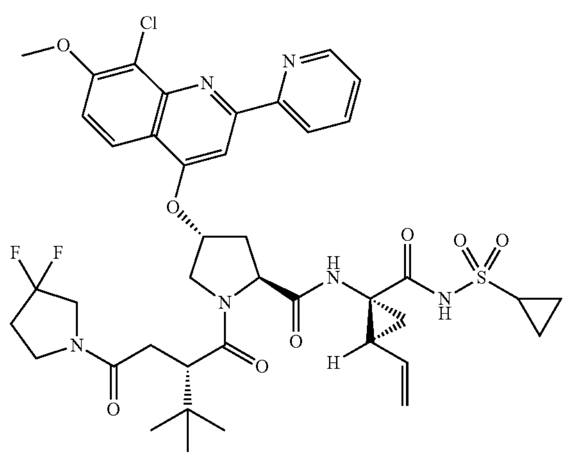 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCC(F)(F)C1)C(C)(C)C)C(=O)NS(=O)(=O)C1CC1] | (2S,4R)-1-((S)-2-tert-butyl-4-(3,3-difluoropyrrolidin-1-yl)-4-oxobutanoyl)-4-(8-chloro-7-methoxy-2-(pyridin-2-yl)quinolin-4-yloxy)-N-((1R)-1-(cyclopropylsulfonyl-carbamoyl)-2-vinylcyclopropyl)pyr-rolidine-2-carboxamide | *** | | |

TABLE I-continued

| Cpd. | STRUCTURE | Name | EC50 | rt | MS + 1 |
|---|---|---|---|---|---|
| 207. | 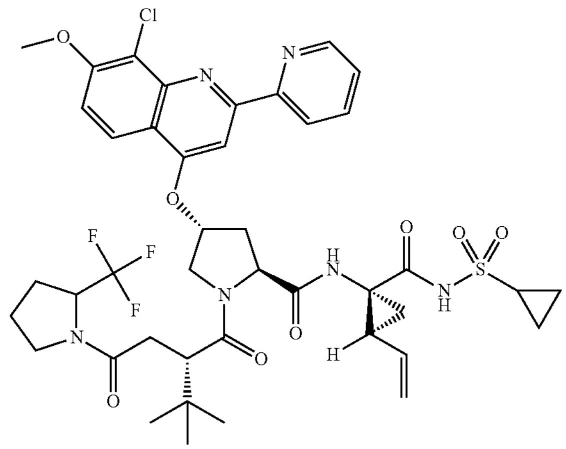 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCCC1C(F)(F)F)C(C)(C)C)C(=O)NS(=O)(=O)C1CC1] | (2S,4R)-1-((2S)-2-tert-butyl-4-oxo-4-(2-(trifluoromethyl)pyrrolidin-1-yl)butanoyl)-4-(8-chloro-7-methoxy-2-(pyridin-2-yl)quinolin-4-yloxy)-N-((1R)-1-(cyclopropylsulfonylcarbamoyl)-2-vinylcyclopropyl)pyrrolidine-2-carboxamide | *** | | |
| 208. | 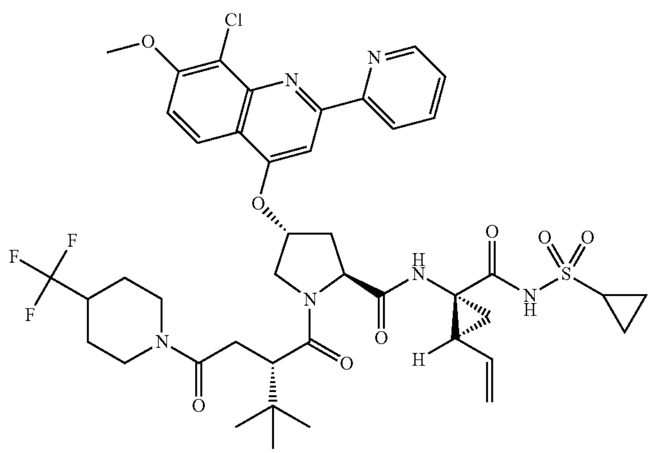 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoromethyl)piperidin-1-yl)butanoyl)-4-(8-chloro-7-methoxy-2-(pyridin-2-yl)quinolin-4-yloxy)-N-((1R)-1-(cyclopropylsulfonylcarbamoyl)-2-vinylcyclopropyl)pyrrolidine-2-carboxamide | *** | | |
| 209. | 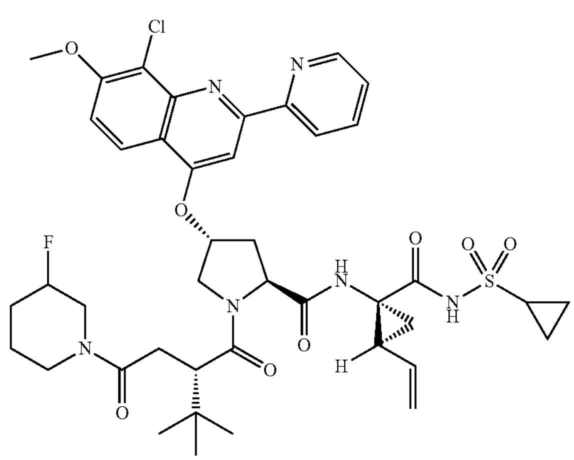 [SMILES: C=C[C@@H]1C[C@]1(NC(=O)[C@@H]1C[C@@H](Oc2cc(-c3ccccn3)nc3c(Cl)c(OC)ccc23)CN1C(=O)[C@@H](CC(=O)N1CCCC(F)C1)C(C)(C)C)C(=O)NS(=O)(=O)C1CC1] | (2S,4R)-1-((2S)-2-tert-butyl-4-(3-fluoropiperidin-1-yl)-4-oxobutanoyl)-4-(8-chloro-7-methoxy-2-(pyridin-2-yl)quinolin-4-yloxy)-N-((1R)-1-(cyclopropylsulfonylcarbamoyl)-2-vinylcyclopropyl)pyrrolidine-2-carboxamide | *** | | |

TABLE I-continued

| Cpd. | STRUCTURE | Name | EC50 | rt | MS + 1 |
|---|---|---|---|---|---|
| 210. | 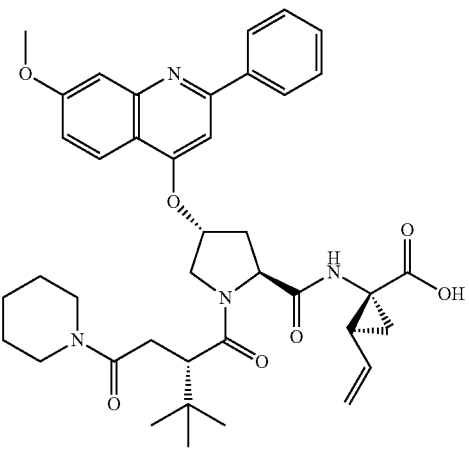 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1)C(C)(C)C)C(=O)O] | (1R)-1-((2S,4R)-1-((S)-2-tert-butyl-4-oxo-4-(piperidin-1-yl)butanoyl)-4-(7-methoxy-2-phenylquinolin-4-yloxy)pyrrolidine-2-carboxamido)-2-vinylcyclopropane-carboxylic acid | * | | |
| 211. | 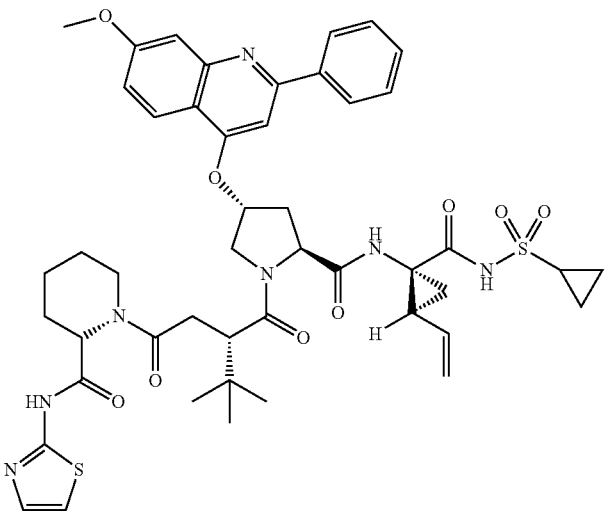 | (2S)-1-((3S)-3-((2S,4R)-2-((1R)-1-(cyclopropyl-sulfonylcarbamoyl)-2-vinylcyclopropyl-carbamoyl)-4-(7-methoxy-2-phenylquinolin-4-yloxy)pyrrolidine-1-carbonyl)-4,4-dimethylpentanoyl)-N-(thiazol-2-yl)piperidine-2-carboxamide | *** | | |
| 212. | 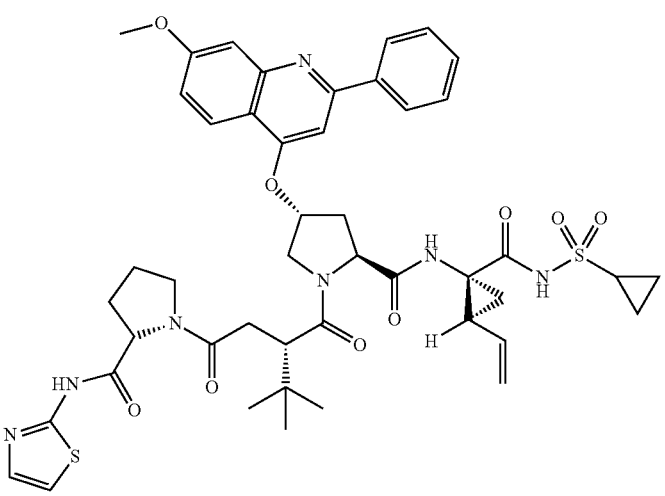 | (2S,4R)-1-((S)-2-tert-butyl-4-oxo-4-((S)-2-(thiazol-2-ylcarbamoyl)pyrrolidin-1-yl)butanoyl)-N-((1R)-1-(cyclopropylsulfonyl-carbamoyl)-2-vinylcyclopropyl)-4-(7-methoxy-2-phenylquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 213. | 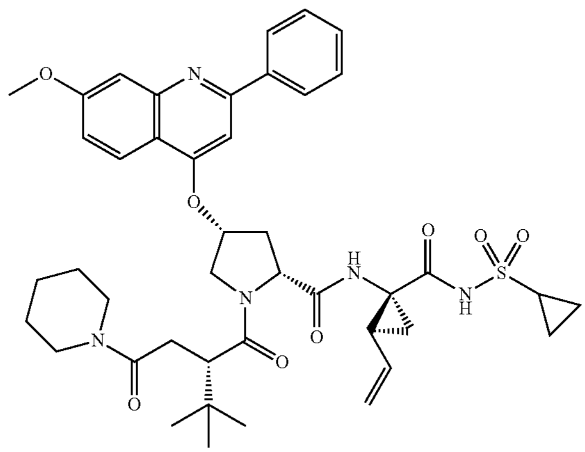 [SMILES: C=C[C@@H]1C[C@]1(NC(=O)[C@H]1C[C@@H](Oc2cc(-c3ccccc3)nc3cc(OC)ccc23)CN1C(=O)[C@@H](CC(=O)N1CCCCC1)C(C)(C)C)C(=O)NS(=O)(=O)C1CC1] | (2R,4R)-1-((S)-2-tert-butyl-4-oxo-4-(piperidin-1-yl)butanoyl)-N-((1R)-1-(cyclopropylsulfonyl-carbamoyl)-2-vinyl-cyclopropyl)-4-(7-methoxy-2-phenylquinolin-4-yloxy)pyrrolidine-2-carboxamide | *** | | |
| 214. | 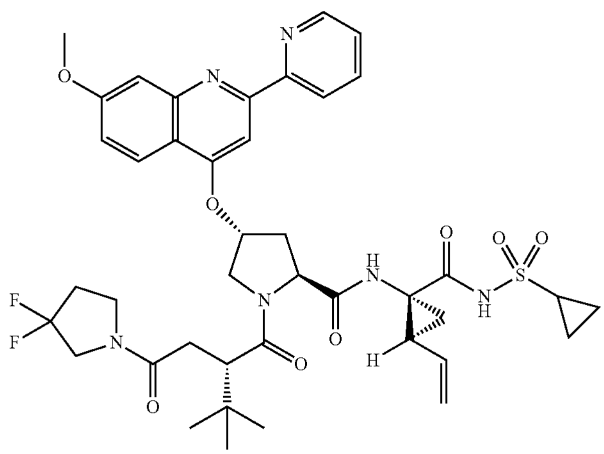 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCC(F)(F)C1)C(C)(C)C)C(=O)NS(=O)(=O)C1CC1] | (2S,4R)-1-((S)-2-tert-butyl-4-(3,3-difluoropyrrolidin-1-yl)-4-oxobutanoyl)-N-((1R)-1-(cyclopropyl-sulfonylcarbamoyl)-2-vinylcyclopropyl)-4-(7-methoxy-2-(pyridin-2-yl)quinolin-4-yloxy)pyrrolidine-2-carboxamide | *** | | |
| 215. | 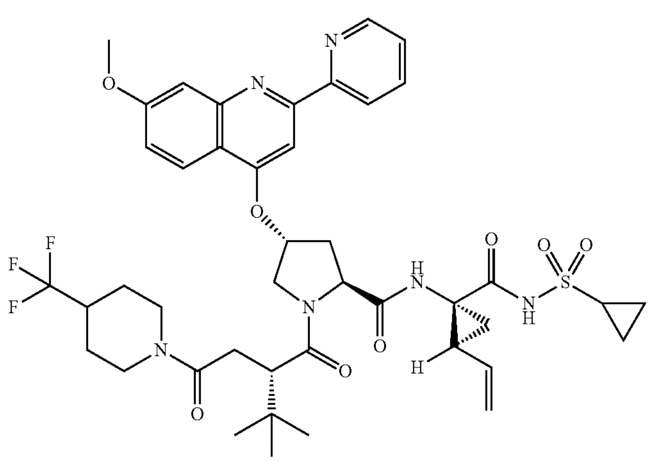 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-N-((1R)-1-(cyclopropyl-sulfonylcarbamoyl)-2-vinylcyclopropyl)-4-(7-methoxy-2-(pyridin-2-yl)quinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 216. | 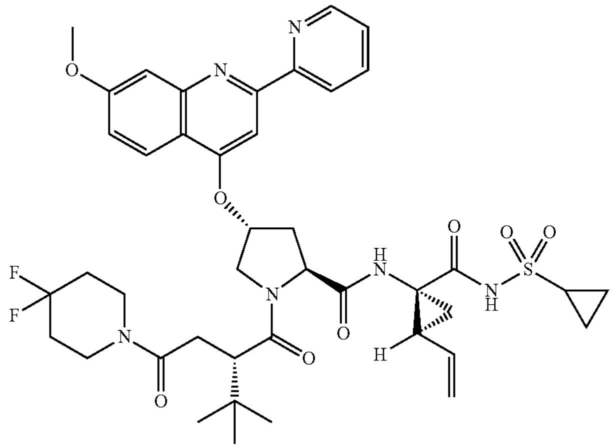 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCC(F)(F)CC1)C(C)(C)C)C(=O)NS(=O)(=O)C1CC1] | (2S,4R)-1-((S)-2-tert-butyl-4-(4,4-difluoropiperidin-1-yl)-4-oxobutanoyl)-N-((1R)-1-(cyclopropylsulfonylcarbamoyl)-2-vinylcyclopropyl)-4-(7-methoxy-2-(pyridin-2-yl)quinolin-4-yloxy)pyrrolidine-2-carboxamide | *** | | |
| 217. | 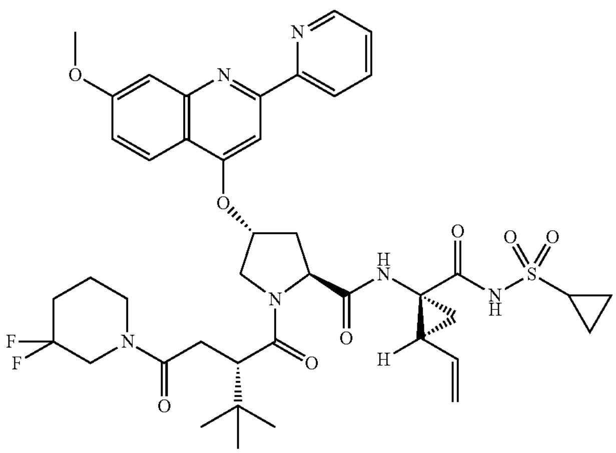 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((1R)-1-(cyclopropylsulfonylcarbamoyl)-2-vinylcyclopropyl)-4-(7-methoxy-2-(pyridin-2-yl)quinolin-4-yloxy)pyrrolidine-2-carboxamide | *** | | |
| 218. | 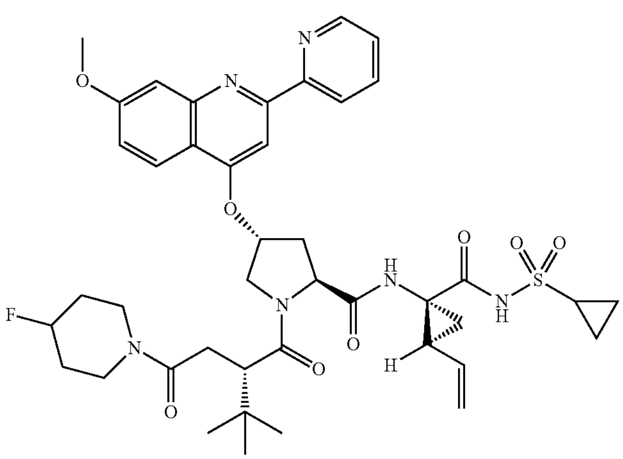 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCC(F)CC1)C(C)(C)C)C(=O)NS(=O)(=O)C1CC1] | (2S,4R)-1-((S)-2-tert-butyl-4-(4-fluoropiperidin-1-yl)-4-oxobutanoyl)-N-((1R)-1-(cyclopropylsulfonylcarbamoyl)-2-vinylcyclopropyl)-4-(7-methoxy-2-(pyridin-2-yl)quinolin-4-yloxy)pyrrolidine-2-carboxamide | *** | | |

| Cpd. | STRUCTURE | Name | EC50 | rt | MS + 1 |
|---|---|---|---|---|---|
| 219. | 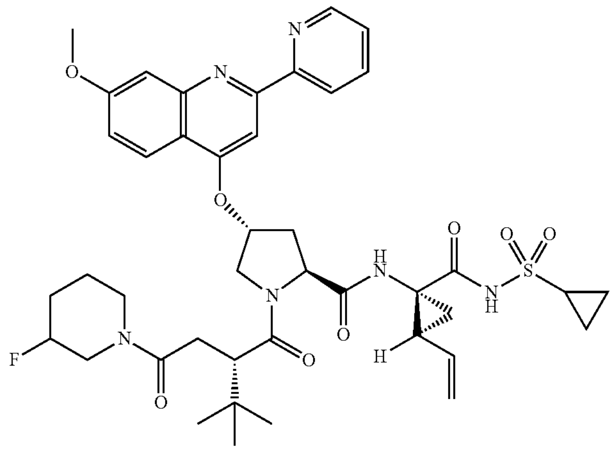 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CCCC(F)C1)C(C)(C)C)C(=O)NS(=O)(=O)C1CC1] | (2S,4R)-1-((2S)-2-tert-butyl-4-(3-fluoropiperidin-1-yl)-4-oxobutanoyl)-N-((1R)-1-(cyclopropyl-sulfonylcarbamoyl)-2-vinylcyclopropyl)-4-(7-methoxy-2-(pyridin-2-yl)quinolin-4-yloxy)pyrrolidine-2-carboxamide | | | |
| 220. | 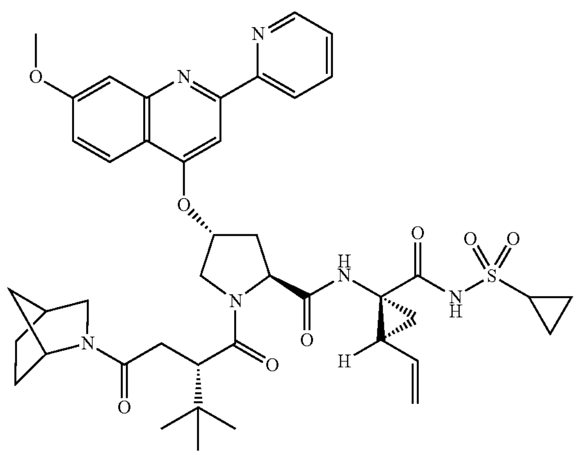 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CC2CCC1C2)C(C)(C)C)C(=O)NS(=O)(=O)C1CC1] | (2S,4R)-1-((2S)-2-(2-(2-azabi-cyclo[2.2.1]heptan-2-yl)-2-oxoethyl)-3,3-dimethylbutanoyl)-N-((1R)-1-(cyclo-propylsulfonyl-carbamoyl)-2-vinylcyclopropyl)-4-(7-methoxy-2-(pyridin-2-yl)quinolin-4-yloxy)pyrrolidine-2-carboxamide | *** | | |
| 221. | 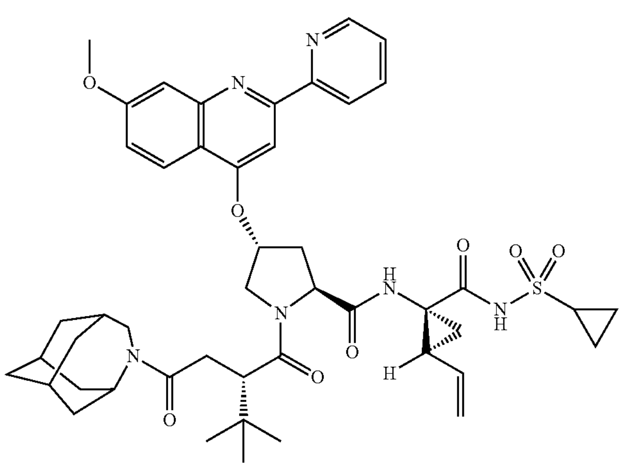 [SMILES: C=C[C@@H]1C[C@]1(NC(=O)[C@@H]1C[C@@H](Oc2cc(-c3ccccn3)nc3cc(OC)ccc23)CN1C(=O)[C@@H](CC(=O)N1CC2CC3CC(C2)CC1C3)C(C)(C)C)C(=O)NS(=O)(=O)C1CC1] | | * | | |

TABLE I-continued

| Cpd. | STRUCTURE | Name | EC50 | rt | MS + 1 |
|---|---|---|---|---|---|
| 222. | 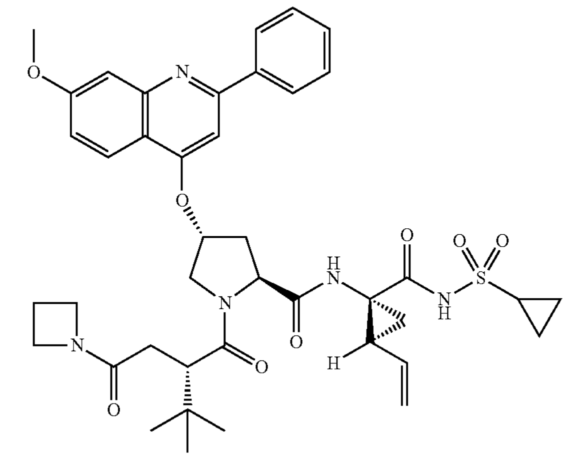 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC1)C(C)(C)C)C(=O)NS(=O)(=O)C1CC1] | (2S,4R)-1-((S)-4-(azetidin-1-yl)-2-tert-butyl-4-oxobutanoyl)-N-((1R)-1-(cyclopropyl-sulfonylcarbamoyl)-2-vinylcyclopropyl)-4-(7-methoxy-2-phenylquinolin-4-yloxy)pyrrolidine-2-carboxamide | *** | | |
| 223. | 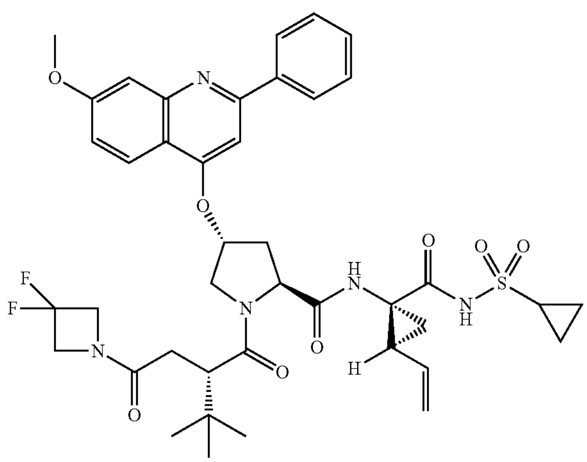 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC(F)(F)C1)C(C)(C)C)C(=O)NS(=O)(=O)C1CC1] | (2S,4R)-1-((S)-2-tert-butyl-4-(3,3-difluoroazetidin-1-yl)-4-oxobutanoyl)-N-((1R)-1-(cyclopropyl-sulfonylcarbamoyl)-2-vinylcyclopropyl)-4-(7-methoxy-2-phenylquinolin-4-yloxy)pyrrolidine-2-carboxamide | *** | | |
| 224. | 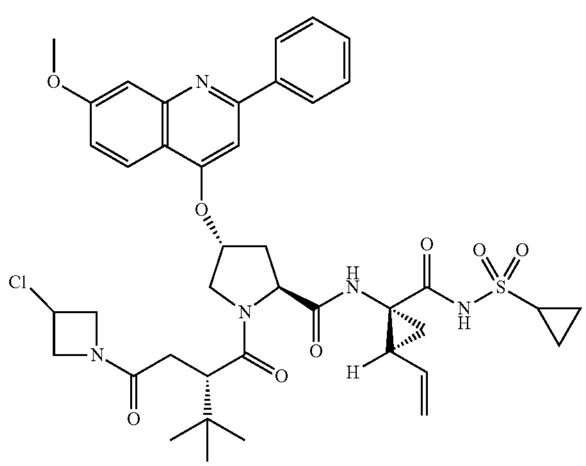 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CC(Cl)C1)C(C)(C)C)C(=O)NS(=O)(=O)C1CC1] | (2S,4R)-1-((S)-2-tert-butyl-4-(3-chloroazetidin-1-yl)-4-oxobutanoyl)-N-((1R)-1-(cyclopropyl-sulfonylcarbamoyl)-2-vinylcyclopropyl)-4-(7-methoxy-2-phenylquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 225. | 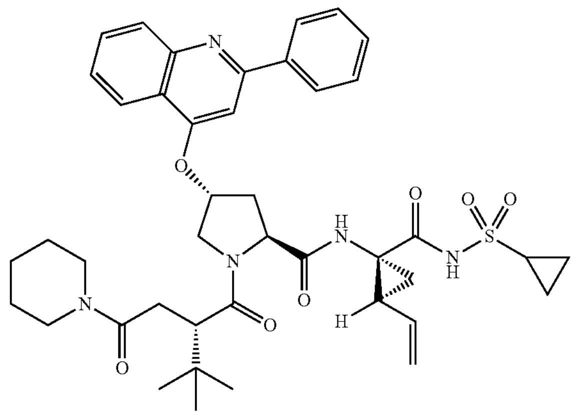 [SMILES: C=C[C@@H]1C[C@]1(NC(=O)[C@@H]1C[C@@H](Oc2cc(-c3ccccc3)nc3ccccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R)-1-(cyclopropyl-sulfonylcarbamoyl)-2-vinylcyclopropyl)-4-(2-phenylquinolin-4-yloxy)pyrrolidine-2-carboxamide | *** | | |
| 226. | 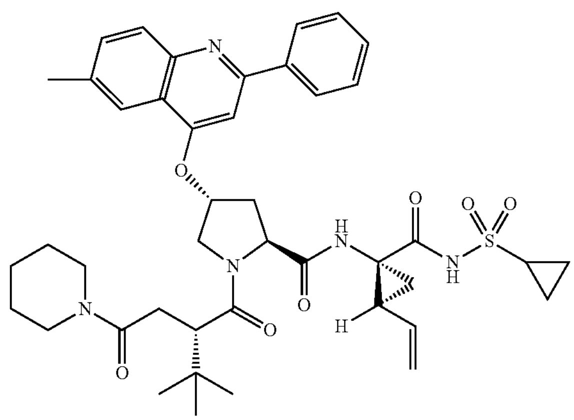 [SMILES: C=C[C@@H]1C[C@]1(NC(=O)[C@@H]1C[C@@H](Oc2cc(-c3ccccc3)nc3ccc(C)cc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R)-1-(cyclopropyl-sulfonylcarbamoyl)-2-vinylcyclopropyl)-4-(6-methyl-2-phenylquinolin-4-yloxy)pyrrolidine-2-carboxamide | *** | | |
| 227. | 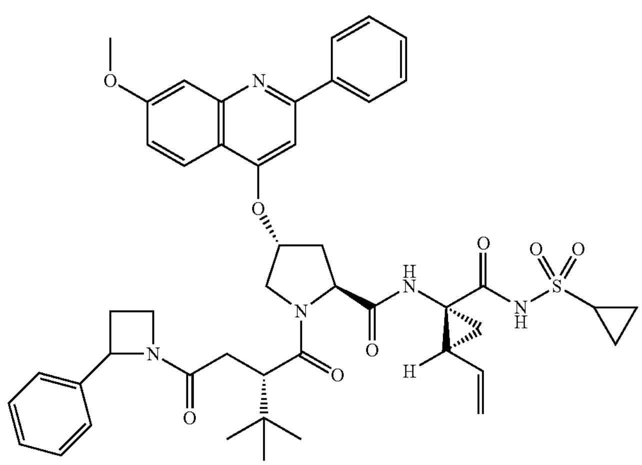 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC1c1ccccc1)C(C)(C)C)C(=O)NS(=O)(=O)C1CC1] | (2S,4R)-1-((2S)-2-tert-butyl-4-oxo-4-(2-phenylazetidin-1-yl)butanoyl)-N-((1R)-1-(cyclopropyl-sulfonylcarbamoyl)-2-vinylcyclopropyl)-4-(7-methoxy-2-phenylquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 228. | 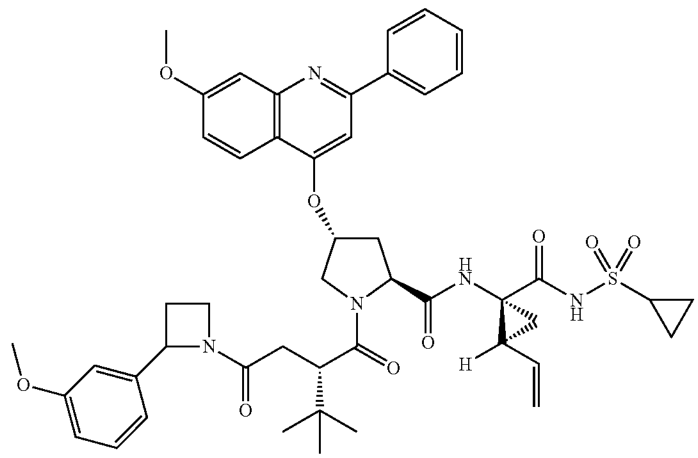 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCC1c1cccc(OC)c1)C(C)(C)C)C(=O)NS(=O)(=O)C1CC1] | (2S,4R)-1-((2S)-2-tert-butyl-4-(2-(3-methoxyphenyl)azetidin-1-yl)-4-oxobutanoyl)-N-((1R)-1-(cyclopropyl-sulfonylcarbamoyl)-2-vinylcyclopropyl)-4-(7-methoxy-2-phenylquinolin-4-yloxy)pyrrolidine-2-carboxamide | *** | | |
| 229. | 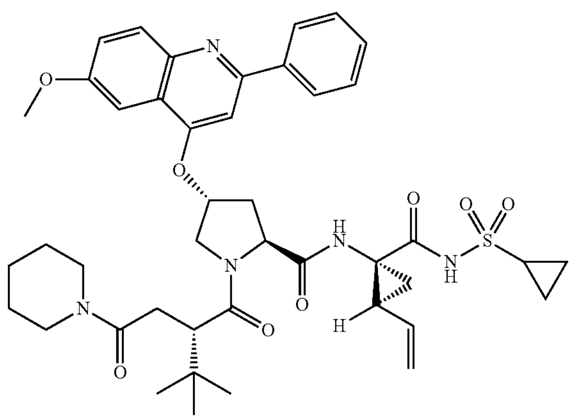 [SMILES: C=C[C@@H]1C[C@]1(NC(=O)[C@@H]1C[C@@H](Oc2cc(-c3ccccc3)nc3ccc(OC)cc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R)-1-(cyclopropyl-sulfonylcarbamoyl)-2-vinylcyclopropyl)-4-(6-methoxy-2-phenylquinolin-4-yloxy)pyrrolidine-2-carboxamide | *** | | |
| 230. | 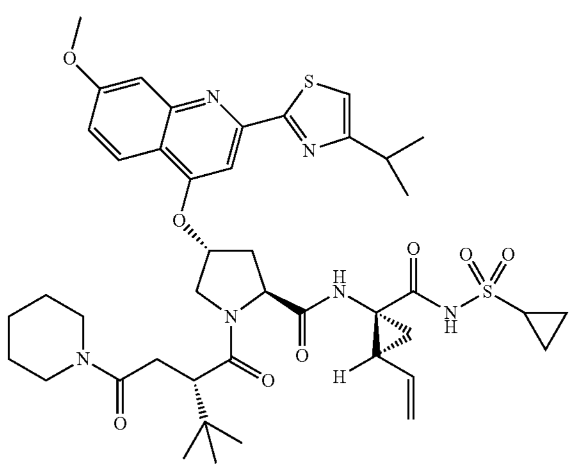 [SMILES: C=C[C@@H]1C[C@]1(NC(=O)[C@@H]1C[C@@H](Oc2cc(-c3nc(C(C)C)cs3)nc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R)-1-(cyclopropyl-sulfonylcarbamoyl)-2-vinylcyclopropyl)-4-(2-(4-isopropylthiazol-2-yl)-7-methoxyquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 231. | 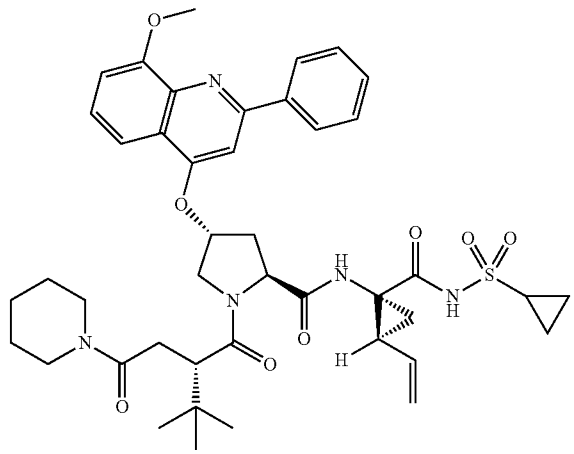 [SMILES: C=C[C@@H]1C[C@]1(NC(=O)[C@@H]1C[C@@H](Oc2cc(-c3ccccc3)nc3c(OC)cccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((2S)-1-(cyclopropyl-sulfonylcarbamoyl)-2-vinylcyclopropyl)-4-(8-methoxy-2-phenylquinolin-4-yloxy)pyrrolidine-2-carboxamide | *** | | |
| 232. | 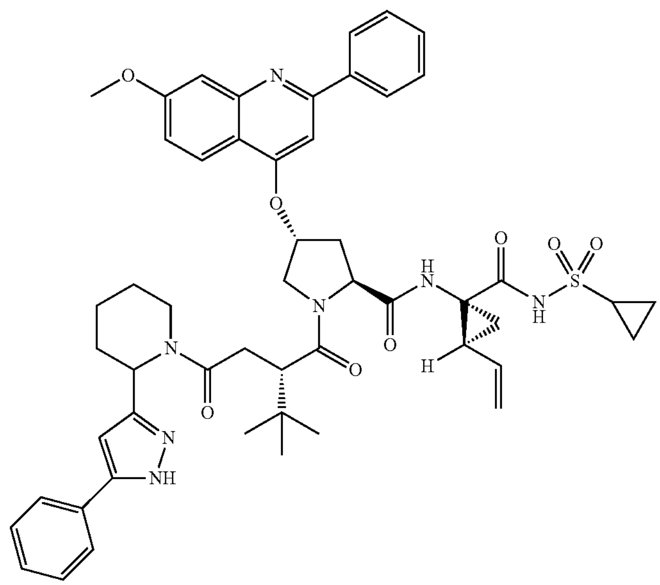 [SMILES: C=C[C@@H]1C[C@]1(NC(=O)[C@@H]1C[C@@H](Oc2cc(-c3ccccc3)nc3cc(OC)ccc23)CN1C(=O)[C@@H](CC(=O)N1CCCCC1c1cc(-c2ccccc2)[nH]n1)C(C)(C)C)C(=O)NS(=O)(=O)C1CC1] | (2S,4R)-1-((2S)-2-tert-butyl-4-oxo-4-(2-(5-phenyl-1H-pyrazol-3-yl)piperidin-1-yl)butanoyl)-N-((2S)-1-(cyclopropyl-sulfonylcarbamoyl)-2-vinylcyclopropyl)-4-(7-methoxy-2-phenylquinolin-4-yloxy)pyrrolidine-2-carboxamide | *** | | |
| 233. | 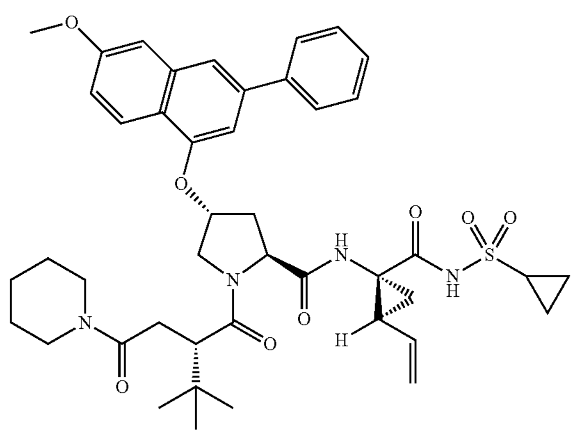 [SMILES: C=C[C@@H]1C[C@]1(NC(=O)[C@@H]1C[C@@H](Oc2cc(-c3ccccc3)cc3cc(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((1R)-1-(cyclopropyl-sulfonylcarbamoyl)-2-vinylcyclopropyl)-4-(6-methoxy-3-phenylnaphthalen-1-yloxy)pyrrolidine-2-carboxamide | *** | | |

| Cpd. | STRUCTURE | Name | EC50 | rt | MS + 1 |
|---|---|---|---|---|---|
| 234. | 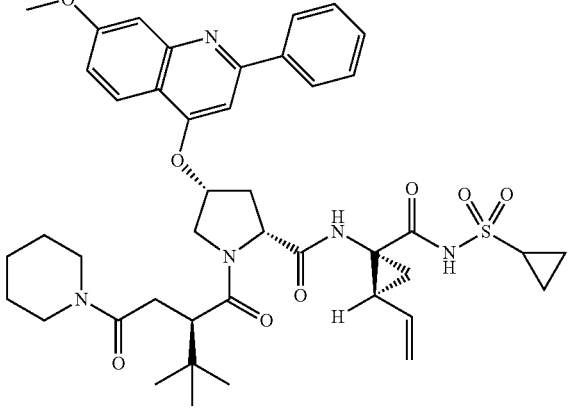 | (2R,4R)-1-((R)-2-tert-butyl-4-oxo-4-(piperidin-1-yl)butanoyl)-N-((2S)-1-(cyclopropyl-sulfonylcarbamoyl)-2-vinylcyclopropyl)-4-(7-methoxy-2-phenylquinolin-4-yloxy)pyrrolidine-2-carboxamide | | | |
| 235. | 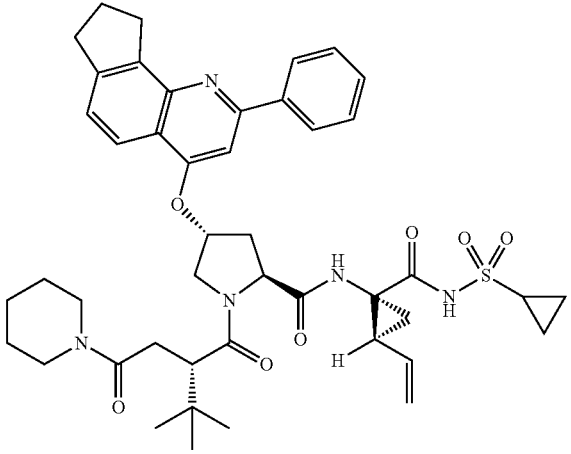 | (2S,4R)-1-((S)-2-tert-butyl-4-oxo-4-(piperidin-1-yl)butanoyl)-N-((2S)-1-(cyclopropyl-sulfonylcarbamoyl)-2-vinylcyclopropyl)-4-(2-phenyl-8,9-dihydro-7H-cyclopenta[h]quinolin-4-yloxy)pyrrolidine-2-carboxamide | *** | | |
| 236. | 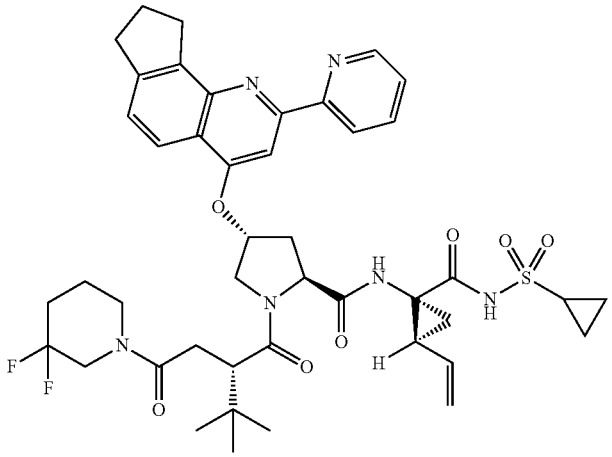 [SMILES: C=C[C@@H]1C[C@]1(NC(=O)[C@@H]1C[C@@H](Oc2cc(-c3ccccn3)nc3c4c(ccc23)CCC4)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropyl-sulfonylcarbamoyl)-2-vinylcyclopropyl)-4-(2-(pyridin-2-yl)-8,9-dihydro-7H-cyclopenta[h]quinolin-4-yloxy)pyrrolidine-2-carboxamide | *** | | |

| Cpd. | STRUCTURE | Name | EC50 | rt | MS + 1 |
|------|-----------|------|------|----|----|
| 237. | 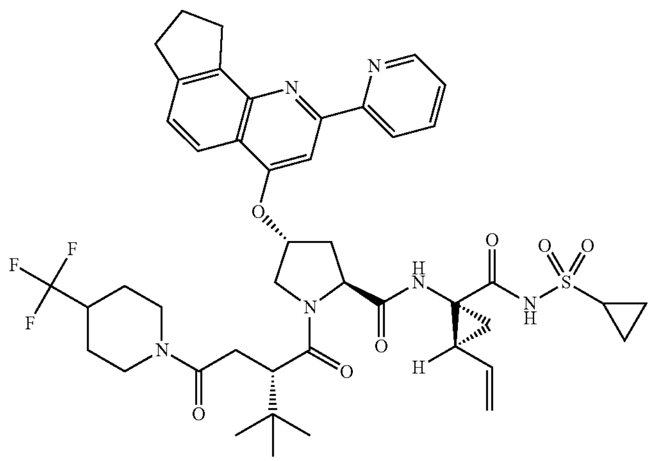 [SMILES: C=C[C@@H]1C[C@]1(NC(=O)[C@@H]1C[C@@H](Oc2cc(-c3ccccn3)nc3c4c(ccc23)CCC4)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-N-((2S)-1-(cyclopropyl-sulfonylcarbamoyl)-2-vinylcyclopropyl)-4-(2-(pyridin-2-yl)-8,9-dihydro-7H-cyclopenta[h]quino-lin-4-yloxy)pyrrolidine-2-carboxamide | *** | | |
| 238. | 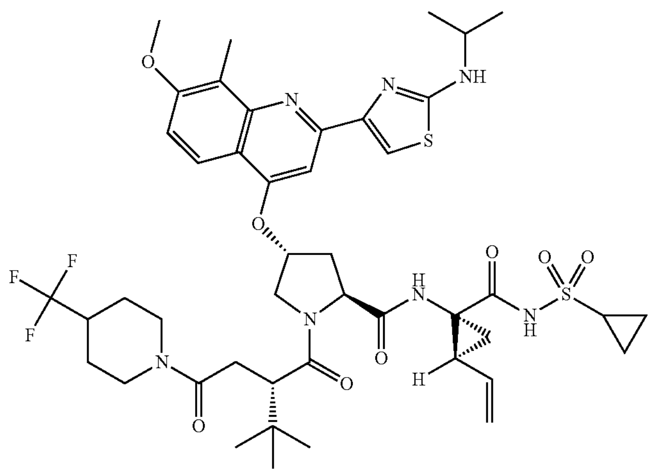 [SMILES: C=C[C@@H]1C[C@]1(NC(=O)[C@@H]1C[C@@H](Oc2cc(-c3csc(NC(C)C)n3)nc3c(C)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-N-((2S)-1-(cyclopropyl-sulfonylcarbamoyl)-2-vinylcyclopropyl)-4-(2-(2-(isopropyl-amino)thiazol-4-yl)-7-methoxy-8-methylquinolin-4-yloxy)pyrrolidine-2-carboxamide | *** | | |
| 239. | 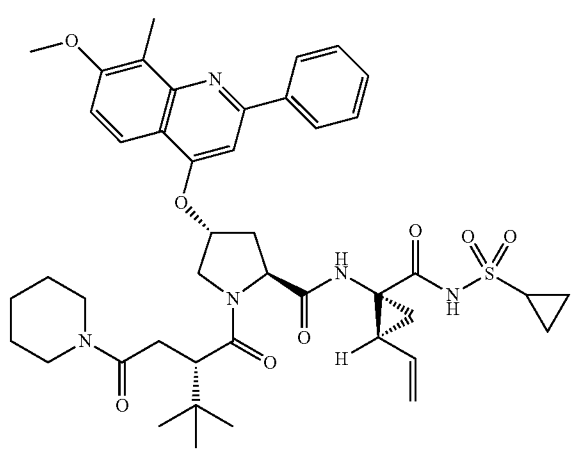 [SMILES: C=C[C@@H]1C[C@]1(NC(=O)[C@@H]1C[C@@H](Oc2cc(-c3ccccc3)nc3c(C)c(OC)ccc23)CN1C(=O)[C@@H](CC(=O)N1CCCCC1)C(C)(C)C)C(=O)NS(=O)(=O)C1CC1] | (2S,4R)4-((S)-2-tert-butyl-4-oxo-4-(piperidin-1-yl)butanoyl)-N-((2S)-1-(cyclopropyl-sulfonylcarbamoyl)-2-vinylcyclopropyl)-4-(7-methoxy-8-methyl-2-phenylquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 240. | 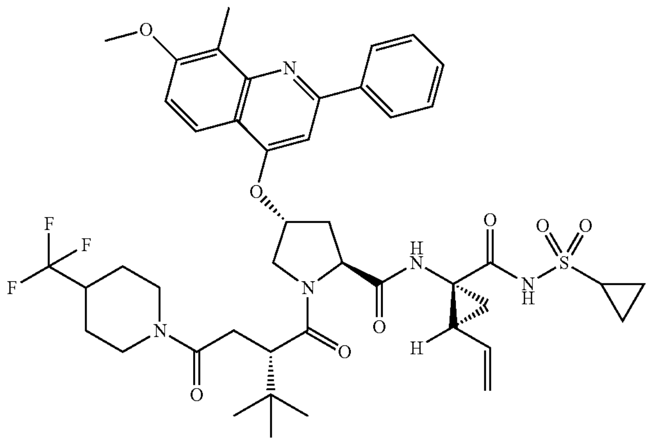 [SMILES: C=C[C@@H]1C[C@]1(NC(=O)[C@@H]1C[C@@H](Oc2cc(-c3ccccc3)nc3c(C)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-N-((1R)-1-(cyclopropyl-sulfonylcarbamoyl)-2-vinylcyclopropyl)-4-(7-methoxy-8-methyl-2-phenylquinolin-4-yloxy)pyrrolidine-2-carboxamide | *** | | |
| 241. | 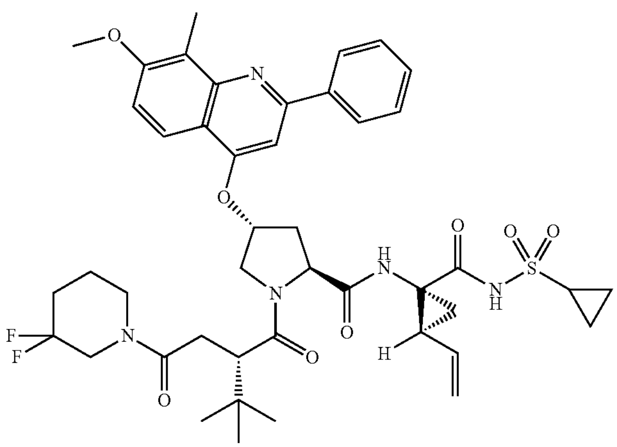 [SMILES: C=C[C@@H]1C[C@]1(NC(=O)[C@@H]1C[C@@H](Oc2cc(-c3ccccc3)nc3c(C)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropyl-sulfonylcarbamoyl)-2-vinylcyclopropyl)-4-(7-methoxy-8-methyl-2-phenylquinolin-4-yloxy)pyrrolidine-2-carboxamide | *** | | |
| 242. | 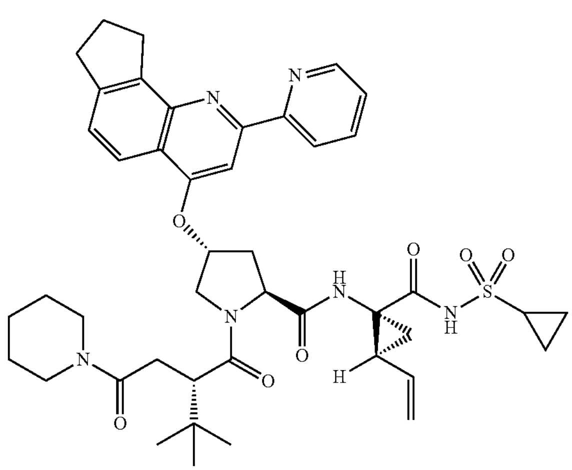 [SMILES: C=C[C@@H]1C[C@]1(NC(=O)[C@@H]1C[C@@H](Oc2cc(-c3ccccn3)nc3c4c(ccc23)CCC4)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((2S)-1-(cyclopropyl-sulfonylcarbamoyl)-2-vinylcyclopropyl)-4-(2-(pyridin-2-yl)-8,9-dihydro-7H-cyclopenta[h]quinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 243. | 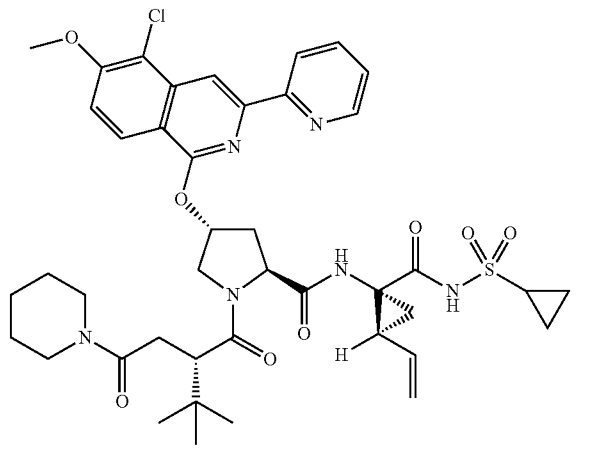 [SMILES: C=C[C@@H]1C[C@]1(NC(=O)[C@@H]1C[C@@H](Oc2nc(-c3ccccn3)cc3c(Cl)c(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-4-(5-chloro-6-methoxy-3-(pyridin-2-yl)isoquinolin-1-yloxy)-N-((2S)-1-(cyclopropyl-sulfonylcarbamoyl)-2-vinylcyclo-propyl)pyrrolidine-2-carboxamide | *** | | |
| 244. | 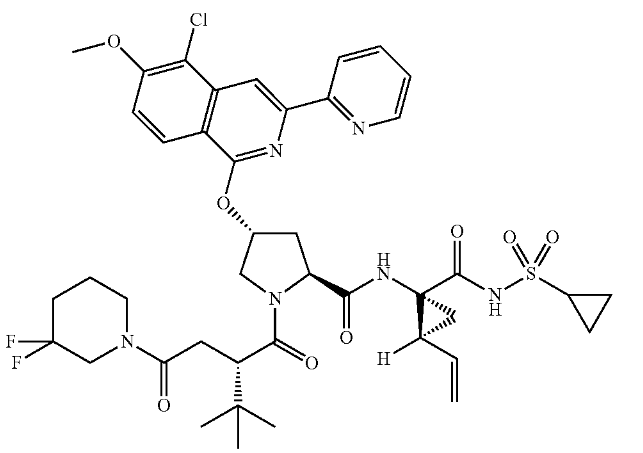 [SMILES: C=C[C@@H]1C[C@]1(NC(=O)[C@@H]1C[C@@H](Oc2nc(-c3ccccn3)cc3c(Cl)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-4-(5-chloro-6-methoxy-3-(pyridin-2-yl)isoquinolin-1-yloxy)-N-((2S)-1-(cyclopropyl-sulfonylcarbamoyl)-2-vinylcyclo-propyl)pyrrolidine-2-carboxamide | *** | | |
| 245. | 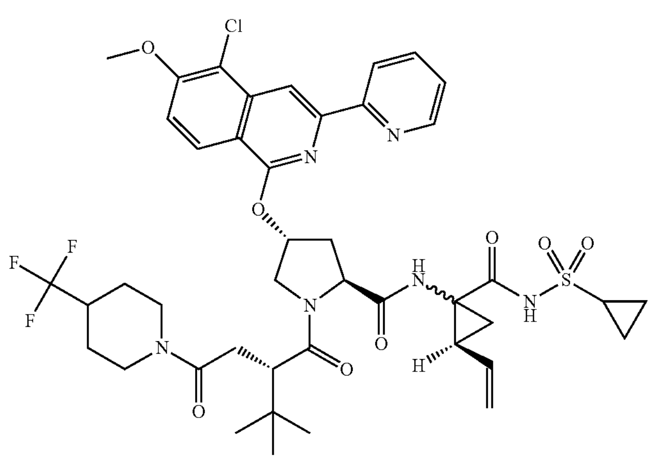 [SMILES: C=C[C@@H]1CC1(NC(=O)[C@@H]1C[C@@H](Oc2nc(-c3ccccn3)cc3c(Cl)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-4-(5-chloro-6-methoxy-3-(pyridin-2-yl)isoquinolin-1-yloxy)-N-((S)-1-(cyclopropyl-sulfonylcarbamoyl)-2-vinylcyclo-propyl)pyrrolidine-2-carboxamide | *** | | |

TABLE I-continued

| Cpd. | STRUCTURE | Name | EC50 | rt | MS + 1 |
|---|---|---|---|---|---|
| 246. | 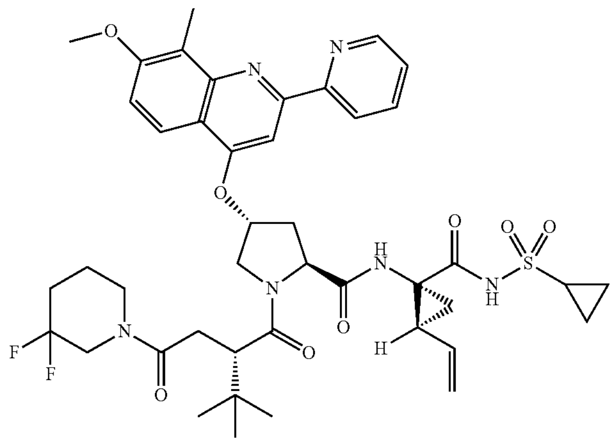 [SMILES: C=C[C@@H]1C[C@]1(NC(=O)[C@@H]1C[C@@H](Oc2cc(-c3ccccn3)nc3c(C)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropyl-sulfonylcarbamoyl)-2-vinylcyclopropyl)-4-(7-methoxy-8-methyl-2-(pyridin-2-yl)quinolin-4-yloxy)pyrrolidine-2-carboxamide | *** | | |
| 247. | 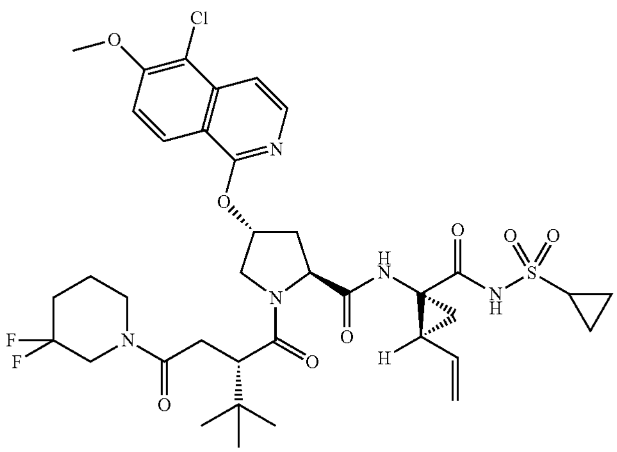 [SMILES: C=C[C@@H]1C[C@]1(NC(=O)[C@@H]1C[C@@H](Oc2nccc3c(Cl)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-4-(5-chloro-6-methoxyisoquinolin-1-yloxy)-N-((2S)-1-(cyclopropyl-sulfonylcarbamoyl)-2-vinylcyclo-propyl)pyrrolidine-2-carboxamide | *** | | |
| 248. | 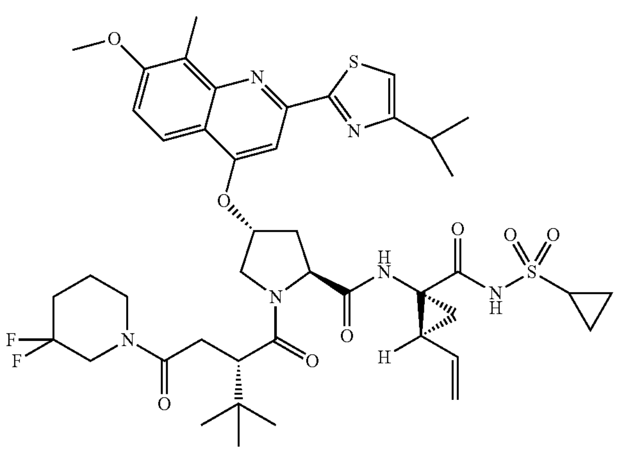 [SMILES: C=C[C@@H]1C[C@]1(NC(=O)[C@@H]1C[C@@H](Oc2cc(-c3nc(C(C)C)cs3)nc3c(C)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropyl-sulfonylcarbamoyl)-2-vinylcyclopropyl)-4-(2-(4-isopropylthiazol-2-yl)-7-methoxy-8-methylquinolin-4-yloxy)pyrrolidine-2-carboxamide | *** | | |

| Cpd. | STRUCTURE | Name | EC50 | rt | MS + 1 |
|---|---|---|---|---|---|
| 249. | 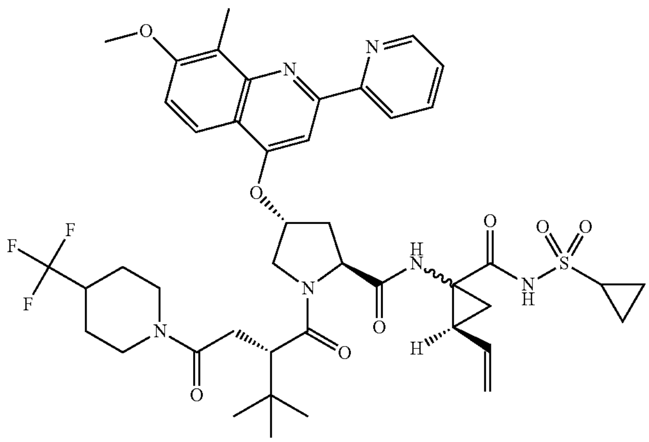 [SMILES: C=C[C@@H]1CC1(NC(=O)[C@@H]1C[C@@H](Oc2cc(-c3ccccn3)nc3c(C)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoromethyl)piperidin-1-yl)butanoyl)-N-((S)-1-(cyclopropylsulfonylcarbamoyl)-2-vinylcyclopropyl)-4-(7-methoxy-8-methyl-2-(pyridin-2-yl)quinolin-4-yloxy)pyrrolidine-2-carboxamide | *** | | |
| 250. | 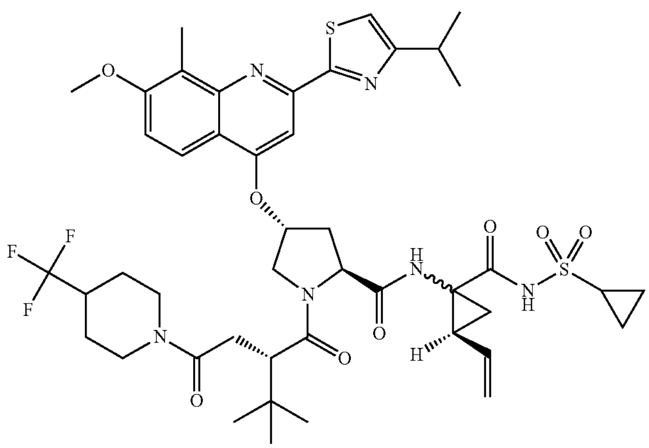 [SMILES: C=C[C@@H]1CC1(NC(=O)[C@@H]1C[C@@H](Oc2cc(-c3nc(C(C)C)cs3)nc3c(C)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoromethyl)piperidin-1-yl)butanoyl)-N-((S)-1-(cyclopropylsulfonylcarbamoyl)-2-vinylcyclopropyl)-4-(2-(4-isopropylthiazol-2-yl)-7-methoxy-8-methylquinolin-4-yloxy)pyrrolidine-2-carboxamide | *** | | |
| 251. | 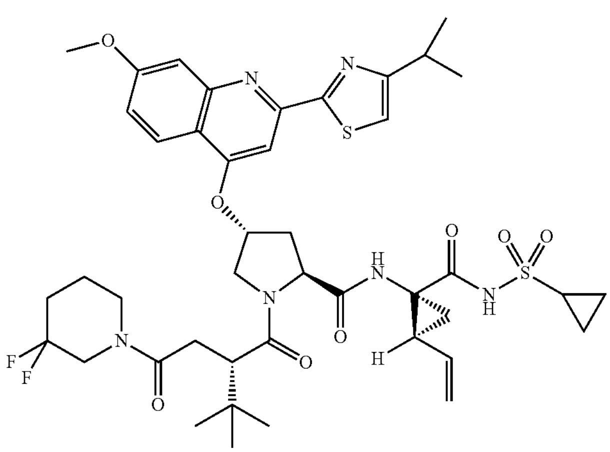 [SMILES: C=C[C@@H]1C[C@]1(NC(=O)[C@@H]1C[C@@H](Oc2cc(-c3nc(C(C)C)cs3)nc3cc(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropylsulfonylcarbamoyl)-2-vinylcyclopropyl)-4-(2-(4-isopropylthiazol-2-yl)-7-methoxyquinolin-4-yloxy)pyrrolidine-2-carboxamide | *** | | |

| Cpd. | STRUCTURE | Name | EC50 | rt | MS + 1 |
|---|---|---|---|---|---|
| 252. | 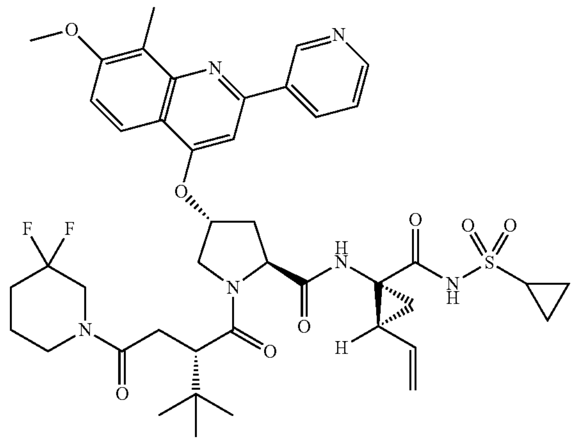 [SMILES: C=C[C@@H]1C[C@]1(NC(=O)[C@@H]1C[C@@H](Oc2cc(-c3cccnc3)nc3c(C)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((2S)-1-(cyclopropyl-sulfonylcarbamoyl)-2-vinylcyclopropyl)-4-(7-methoxy-8-methyl-2-(pyridin-3-yl)quinolin-4-yloxy)pyrrolidine-2-carboxamide | *** | | |
| 253. | 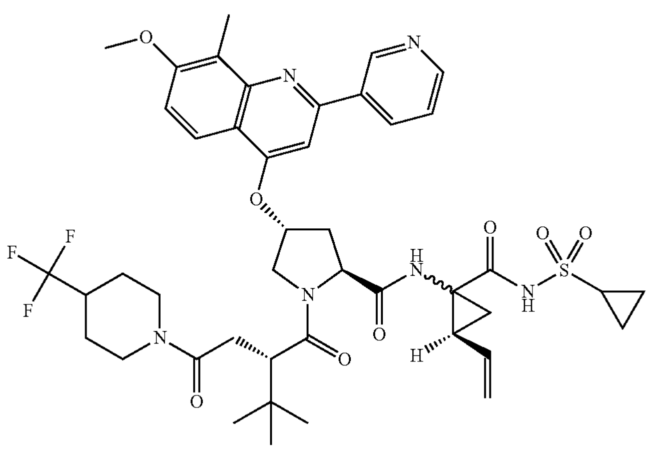 [SMILES: C=C[C@@H]1CC1(NC(=O)[C@@H]1C[C@@H](Oc2cc(-c3cccnc3)nc3c(C)c(OC)ccc23)CN1C(=O)[C@@H](CC(=O)N1CCC(C(F)(F)F)CC1)C(C)(C)C)C(=O)NS(=O)(=O)C1CC1] | (2S,4R)-1-((S)-2-tert-butyl-4-oxo-4-(4-(trifluoro-methyl)piperidin-1-yl)butanoyl)-N-((S)-1-(cyclopropyl-sulfonylcarbamoyl)-2-vinylcyclopropyl)-4-(7-methoxy-8-methyl-2-(pyridin-3-yl)quinolin-4-yloxy)pyrrolidine-2-carboxamide | *** | | |
| 254. | 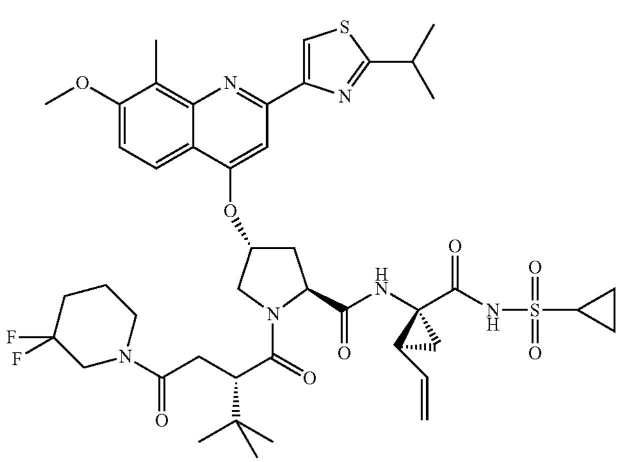 [SMILES: C=C[C@@H]1C[C@]1(NC(=O)[C@@H]1C[C@@H](Oc2cc(-c3csc(C(C)C)n3)nc3c(C)c(OC)ccc23)CN1C(=O)[C@@H](CC(=O)N1CCCC(F)(F)C1)C(C)(C)C)C(=O)NS(=O)(=O)C1CC1] | (2S,4R)-1-((S)-2-tert-butyl-4-(3,3-difluoropiperidin-1-yl)-4-oxobutanoyl)-N-((1R)-1-(cyclopropyl-sulfonylcarbamoyl)-2-vinylcyclopropyl)-4-(2-(2-isopropylthiazol-4-yl)-7-methoxy-8-methylquinolin-4-yloxy)pyrrolidine-2-carboxamide | *** | | |

TABLE I-continued

| Cpd. | STRUCTURE | Name | EC50 | rt | MS + 1 |
|---|---|---|---|---|---|
| 255. | 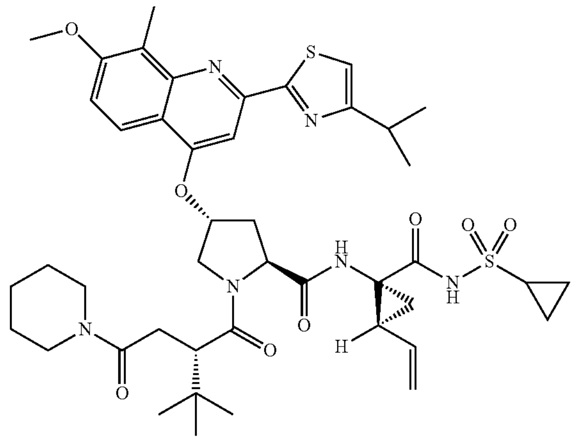 [SMILES: C=C[C@@H]1C[C@]1(NC(=O)[C@@H]1C[C@@H](Oc2cc(-c3nc(C(C)C)cs3)nc3c(C)c(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((2S)-1-(cyclopropyl-sulfonylcarbamoyl)-2-vinylcyclopropyl)-4-(2-(4-isopropylthiazol-2-yl)-7-methoxy-8-methylquinolin-4-yloxy)pyrrolidine-2-carboxamide | *** | | |
| 256. | 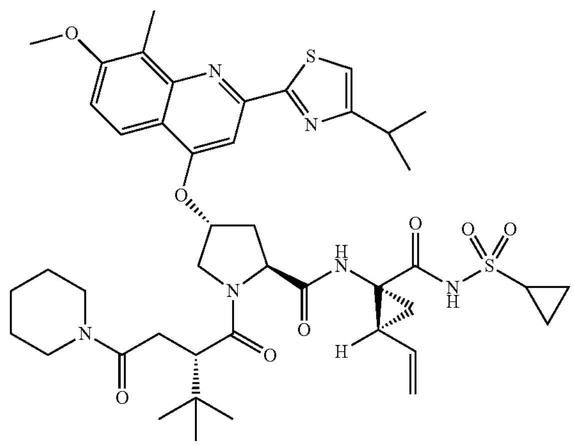 [SMILES: C=C[C@@H]1C[C@]1(NC(=O)[C@@H]1C[C@@H](Oc2cc(-c3nc(C(C)C)cs3)nc3c(C)c(OC)ccc23)CN1C(=O)[C@@H](CC(=O)N1CCCCC1)C(C)(C)C)C(=O)NS(=O)(=O)C1CC1] | (2S,4R)-1-((S)-2-tert-butyl-4-oxo-4-(piperidin-1-yl)butanoyl)-N-((2S)-1-(cyclopropyl-sulfonylcarbamoyl)-2-vinylcyclopropyl)-4-(2-(4-isopropylthiazol-2-yl)-7-methoxy-8-methylquinolin-4-yloxy)pyrrolidine-2-carboxamide | | | |
| 257. | 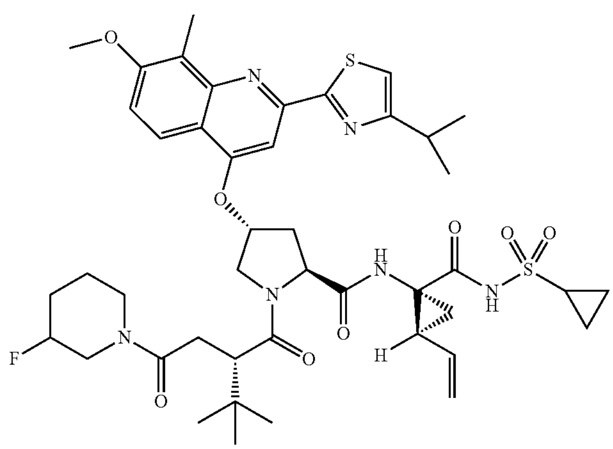 [SMILES: C=C[C@@H]1C[C@]1(NC(=O)[C@@H]1C[C@@H](Oc2cc(-c3nc(C(C)C)cs3)nc3c(C)c(OC)ccc23)CN1C(=O)[C@@H](CC(=O)N1CCCC(F)C1)C(C)(C)C)C(=O)NS(=O)(=O)C1CC1] | (2S,4R)-1-((2S)-2-tert-butyl-4-(3-fluoropiperidin-1-yl)-4-oxobutanoyl)-N-((2S)-1-(cyclopropyl-sulfonylcarbamoyl)-2-vinylcyclopropyl)-4-(2-(4-isopropylthiazol-2-yl)-7-methoxy-8-methylquinolin-4-yloxy)pyrrolidine-2-carboxamide | | | |

* ($EC_{50}$ < 1 micromolar),  ($EC_{50}$ between 1 micromolar and 10 micromolar) and * ($EC_{50}$ greater than 10 micromolar)

Example 3

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

3A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

3B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well ($6-7.5 \times 10^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

3C. Treatment of HCV-Replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 fcells/100 μl/well of 96 well plate ($6-7.5 \times 10^5$ cells/10 ml/plate). Plates are placed into 37° C. 5% $CO_2$ incubator overnight.

3D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

197

When tested in this assay Compounds 11, 16, 25, 33, 38, 39, and 40 exhibit EC50 values of about 10 micromolar or less.

Example 4

Cytotoxicity Assays

To insure that the decrease in replicon replication is due to compound activity against the HCV replicon rather than non-specific toxicity assays are used to quantitate compound cytotoxicity.

4A. Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

4B. MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Albumin and MTS methods for determining cytotoxicity may be obtained as follows: Cells are treated with different concentrations of test compound or Helioxanthin for a three day-period. Prior to lysis for detection albumin as described above, the MTS reagent is added according to manufacturer's instruction to each well and incubate at 37° C. and read at OD 490 nm. The cellular albumin quantitation is then performed as described above.

198

What is claimed is:

1. A compound or pharmaceutically acceptable salt thereof, wherein the compound is chosen from

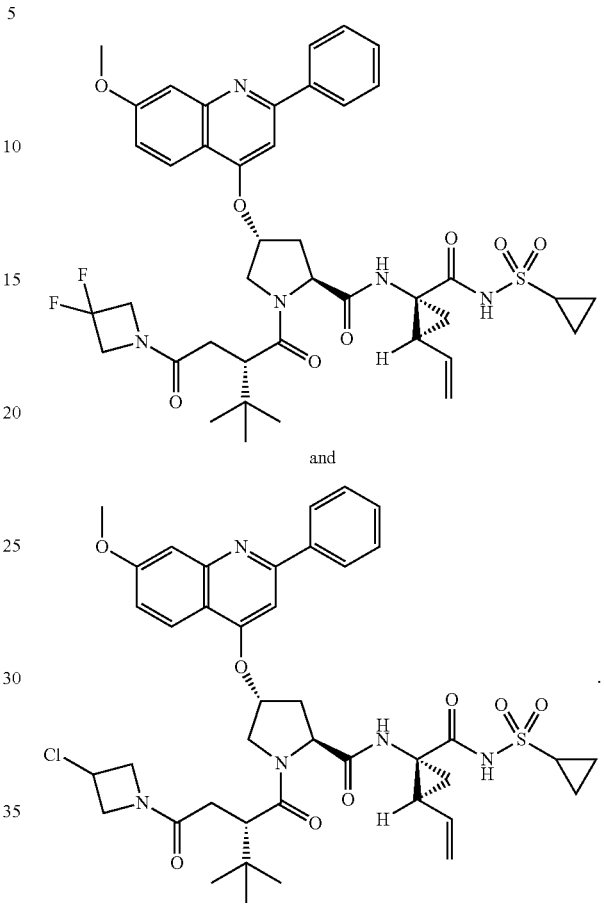

and

2. A pharmaceutical composition comprising a therapeutically effective amount of one or more compounds or salts of claim 1 and at least one pharmaceutically acceptable carrier.

3. A method of treating a hepatitis C infection in a patient, comprising providing a therapeutically effective amount of one or more compounds of claim 1 to the patient.

4. The method of claim 3 wherein the therapeutically effective amount is an amount sufficient to significantly decrease the number of HCV antibodies in the patient's blood or serum.

* * * * *